United States Patent
Li et al.

(10) Patent No.: US 10,793,546 B2
(45) Date of Patent: Oct. 6, 2020

(54) NON-PLATINUM METAL COMPLEXES FOR EXCIMER BASED SINGLE DOPANT WHITE ORGANIC LIGHT EMITTING DIODES

(71) Applicant: Arizona Board of Regents on behalf of Arizona State University

(72) Inventors: Jian Li, Tempe, AZ (US); Liang Huang, Mesa, AZ (US); Tyler Fleetham, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/503,690

(22) PCT Filed: Aug. 14, 2015

(86) PCT No.: PCT/US2015/045416
§ 371 (c)(1),
(2) Date: Feb. 13, 2017

(87) PCT Pub. No.: WO2016/025921
PCT Pub. Date: Feb. 18, 2016

(65) Prior Publication Data
US 2017/0305881 A1 Oct. 26, 2017

Related U.S. Application Data

(60) Provisional application No. 62/037,802, filed on Aug. 15, 2014.

(51) Int. Cl.
| | | |
|---|---|---|
| C07D 401/14 | (2006.01) | |
| C09K 11/06 | (2006.01) | |
| C07F 15/00 | (2006.01) | |
| C07F 1/12 | (2006.01) | |
| H01L 51/00 | (2006.01) | |
| C07F 9/50 | (2006.01) | |
| C07F 7/08 | (2006.01) | |
| H01L 51/50 | (2006.01) | |

(52) U.S. Cl.
CPC ............ *C07D 401/14* (2013.01); *C07F 1/12* (2013.01); *C07F 7/0803* (2013.01); *C07F 9/5045* (2013.01); *C07F 15/006* (2013.01); *C07F 15/0033* (2013.01); *C07F 15/0073* (2013.01); *C09K 11/06* (2013.01); *H01L 51/0067* (2013.01); *H01L 51/0084* (2013.01); *H01L 51/50* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1074* (2013.01); *C09K 2211/1096* (2013.01); *C09K 2211/18* (2013.01); *C09K 2211/185* (2013.01); *H01L 51/0081* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,707,745 A | 1/1998 | Forrest et al. |
| 5,844,363 A | 12/1998 | Gu et al. |
| 6,200,695 B1 | 3/2001 | Arai |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks et al. |
| 9,318,725 B2 | 4/2016 | Li |
| 9,324,957 B2 | 4/2016 | Li et al. |
| 9,382,273 B2 | 7/2016 | Li |
| 9,385,329 B2 | 7/2016 | Li et al. |
| 9,425,415 B2 | 8/2016 | Li et al. |
| 9,461,254 B2 | 10/2016 | Tsai |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Authorized Officer Younjoo Lee, International Search Report and Written Opinion for PCT/US2015/045416 dated Oct. 27, 2015, 20 pages.

(Continued)

*Primary Examiner* — Clinton A Brooks
(74) *Attorney, Agent, or Firm* — Riverside Law LLP

(57) ABSTRACT

Complexes and devices, such as organic light emitting devices and full color displays, including a compound of the formula wherein: M is $Pd^{2+}$, $Ir^+$, $Rh^+$, or $Au^{3+}$; each of $V^1$, $V^2$, $V^3$, and $V^4$ is coordinated to M and is independently N, C, P, B, or Si; each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR, where each R is independently substituted or unsubstituted C1-C4 alkyl or substituted or unsubstituted aryl.

18 Claims, 12 Drawing Sheets

(56) References Cited

U.S. PATENT DOCUMENTS

| | | |
|---|---|---|
| 9,550,801 B2 | 1/2017 | Li et al. |
| 9,617,291 B2 | 4/2017 | Li et al. |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 9,879,039 B2 | 1/2018 | Li |
| 9,882,150 B2 | 1/2018 | Li |
| 9,899,614 B2 | 2/2018 | Li |
| 9,920,242 B2 | 3/2018 | Li |
| 9,923,155 B2 | 3/2018 | Li et al. |
| 9,941,479 B2 | 4/2018 | Li |
| 9,947,881 B2 | 4/2018 | Li |
| 10,020,455 B2 | 7/2018 | Li |
| 10,033,003 B2 | 7/2018 | Li |
| 10,056,564 B2 | 8/2018 | Li |
| 10,056,567 B2 | 8/2018 | Li |
| 2002/0068190 A1 | 6/2002 | Tsuboyama et al. |
| 2003/0062519 A1 | 4/2003 | Yamazaki et al. |
| 2003/0186077 A1 | 10/2003 | Chen |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0094875 A1 | 5/2006 | Itoh et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0255721 A1 | 11/2006 | Igarashi et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1* | 2/2009 | Igarashi ............. C09K 11/02 313/504 |
| 2009/0079340 A1 | 3/2009 | Kinoshita et al. |
| 2009/0128008 A1 | 5/2009 | Ise et al. |
| 2009/0153045 A1 | 6/2009 | Kinoshita et al. |
| 2009/0218561 A1 | 9/2009 | Kitamura et al. |
| 2009/0261721 A1 | 10/2009 | Murakanni et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2010/0171418 A1 | 7/2010 | Kinoshita et al. |
| 2011/0049496 A1 | 3/2011 | Fukuzaki |
| 2011/0227058 A1 | 9/2011 | Masui et al. |
| 2012/0095232 A1 | 4/2012 | Li et al. |
| 2012/0181528 A1 | 7/2012 | Takada et al. |
| 2012/0202997 A1 | 8/2012 | Parham et al. |
| 2012/0215001 A1 | 8/2012 | Li et al. |
| 2012/0223634 A1 | 9/2012 | Xia et al. |
| 2012/0273736 A1 | 11/2012 | James et al. |
| 2012/0302753 A1 | 11/2012 | Li |
| 2013/0048963 A1 | 2/2013 | Beers et al. |
| 2013/0082245 A1 | 4/2013 | Kottas et al. |
| 2013/0168656 A1 | 7/2013 | Tsai et al. |
| 2013/0172561 A1 | 7/2013 | Tsai et al. |
| 2013/0203996 A1* | 8/2013 | Li .................... C07D 213/643 546/4 |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0207086 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197285 A1 | 7/2016 | Zeng et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li |
| 2017/0005278 A1 | 1/2017 | Li et al. |
| 2017/0012224 A1 | 1/2017 | Li et al. |
| 2017/0047533 A1 | 2/2017 | Li et al. |
| 2017/0066792 A1 | 3/2017 | Li et al. |
| 2017/0069855 A1 | 3/2017 | Li et al. |
| 2017/0267923 A1 | 9/2017 | Li |
| 2017/0271611 A1 | 9/2017 | Li et al. |
| 2017/0301871 A1 | 10/2017 | Li |
| 2017/0305881 A1 | 10/2017 | Li et al. |
| 2017/0331056 A1 | 11/2017 | Li et al. |
| 2017/0373260 A1 | 12/2017 | Li |
| 2018/0006246 A1 | 1/2018 | Li |
| 2018/0053904 A1 | 2/2018 | Li |
| 2018/0130960 A1 | 5/2018 | Li |
| 2018/0148464 A1 | 5/2018 | Li |
| 2018/0166655 A1 | 6/2018 | Li et al. |
| 2018/0175329 A1 | 6/2018 | Li |
| 2018/0194790 A1 | 7/2018 | Li |
| 2018/0219161 A1 | 8/2018 | Li |
| 2018/0226592 A1 | 8/2018 | Li |
| 2018/0226593 A1 | 8/2018 | Li |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 103102372 | 5/2013 |
| CN | 104232076 | 12/2014 |
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |

(56) References Cited

FOREIGN PATENT DOCUMENTS

| | | |
|---|---|---|
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007042875 | 2/2007 |
| JP | 2007051243 | 3/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007519614 | 7/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 A | 4/2009 |
| JP | 2009161524 | 7/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2010171205 | 8/2010 |
| JP | 2011071452 | 4/2011 |
| JP | 2012079895 | 4/2012 |
| JP | 2012079898 | 4/2012 |
| JP | 2012222255 | 11/2012 |
| JP | 2012231135 | 11/2012 |
| JP | 2013023500 | 2/2013 |
| JP | 2013048256 | 3/2013 |
| JP | 2013525436 | 6/2013 |
| JP | 2014019701 | 2/2014 |
| JP | 2014058504 | 4/2014 |
| JP | 5604505 | 10/2014 |
| JP | 2014221807 | 11/2014 |
| JP | 2014239225 | 12/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 | 3/2017 |
| WO | WO2000070655 | 11/2000 |
| WO | WO2004003108 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012116231 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 | 1/2014 |
| WO | WO2014031019 | 2/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029137 | 2/2016 |
| WO | WO2016029186 | 2/2016 |
| WO | WO2016197019 | 12/2016 |
| WO | WO2018071697 | 4/2018 |
| WO | WO2018140765 | 8/2018 |

OTHER PUBLICATIONS

Authorized Officer Younjoo Lee, International Preliminary Report on Patentability for PCT/US2015/045416 dated Mar. 2, 2017, 15 pages.
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Barry O'Brien et al.: White organic light emitting diodes using Pt-based red, green and blue phosphorescent dopants. Proc. SPIE, vol. 8829, pp. 1-6, Aug. 25, 2013.

(56) References Cited

OTHER PUBLICATIONS

Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate OΛNΛCΛN Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate OΛNΛCΛN ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.

Barry O'Brien et al., "High efficiency white organic light emitting diodes employing blue and red platinum emitters," Journal of Photonics for Energy, vol. 4, 2014, pp. 043597-1-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient 'pure' blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Murakami; JP 2007258550, English machine translation from EPO, Oct. 4, 2007. 80 pages.
Murakami; JP 2007324309, English machine translation from EPO, Dec. 13, 2007, 89 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligands," Helvetica Chimica Acta, vol. 71, Issue 5, Aug. 10, 1988, pp. 1053-1059.
U.S. Appl. No. 61/945,940, filed Feb. 28, 2014, Chiral Metal Complexes as Emitters for Organic Polarized Electroluminescent Devices, Jian Li.
U.S. Appl. No. 15/119,961, filed Aug. 18, 2016, Chiral Metal Complexes as Emitters for Organic Polarized Electroluminescent Devices, Jian Li.
U.S. Appl. No. 62/037,802, filed Aug. 15, 2014, Non-Platinum Metal Complexes for Excimer Based Single Dopant White Organic Light Emitting Diodes, Jian Li, Liang Huang, Tyler Fleetham.
U.S. Appl. No. 62/040,470, filed Aug. 22, 2014, Organic Light-Emitting Diodes With Fluorescent and Phosphorescent Emitters, Jian Li, Tyler Fleetham.
U.S. Appl. No. 15/505,527, filed Feb. 21, 2017, Organic Light-Emitting Diodes With Fluorescent and Phosphorescent Emitters, Jian Li, Tyler Fleetham.
U.S. Appl. No. 62/040,727, filed Aug. 22, 2014, Metal-Assisted Delayed Fluorescent Materials as Co-Host Materials for Fluorescent OLEDs, Jian Li.
U.S. Appl. No. 15/505,544, filed Feb. 21, 2017, Metal-Assisted Delayed Fluorescent Materials as Co-Host Materials for Fluorescent OLEDs, Jian Li.
U.S. Appl. No. 62/050,243, filed Sep. 15, 2014, Ionic Liquid Catholyte, C. Austen Angell, Leigang Xue.
U.S. Appl. No. 62/138,710, filed Mar. 26, 2015, Ionic Liquid Catholytes and Electrochemical Devices Containing Same, Charles Austen Angell, Leigang Xue.
U.S. Appl. No. 15/508,032, filed Mar. 1, 2017, Ionic Liquid Catholytes and Electrochemical Devices Containing Same, Charles Austen Angell, Leigang Xue.
U.S. Appl. No. 62/170,809, filed Jun. 4, 2015, Transparent Electroluminescent Devices With Controlled One-Side Emissive Displays, Jian Li.
U.S. Appl. No. 15/577,655, filed Nov. 28, 2017, Transparent Electroluminescent Devices With Controlled One-Side Emissive Displays, Jian Li.
U.S. Appl. No. 62/323,383, filed Apr. 15, 2016, OLED With Doped Electron Blocking Layer, Jian Li.
U.S. Appl. No. 62/377,747, filed Aug. 22, 2016, OLED With Multi-Emissive Material Layer, Jian Li.
U.S. Appl. No. 62/407,020, filed Oct. 12, 2016, Narrow Band Red Phosphorescent Tetradentate Platinum (II) Complexes, Jian Li, Qunbo Mei.
U.S. Appl. No. 62/435,455, filed Dec. 16, 2016, Organic Light Emitting Diode With Split Emissive Layer, Jian Li, Kody George Klimes.

(56) References Cited

OTHER PUBLICATIONS

U.S. Appl. No. 14/437,963, filed Apr. 23, 2015 Metal Complexes, Methods, and Uses Thereof, Eric Turner, Jian Li.
U.S. Appl. No. 15/905,385, filed Feb. 26, 2018, Metal Complexes, Methods, and Uses Thereof, Eric Turner, Jian Li.
U.S. Appl. No. 61/166,901, filed Apr. 6, 2009, Synthesis of Four Coordinated Platinum Complexes and Their Applications in Light Emitting Devices Thereof, Eric Turner, Jian Li, Zixing Wang.
U.S. Appl. No. 13/263,096, filed Jan. 3, 2014, Synthesis of Four Coordinated Platinum Complexes and Their Applications in Light Emitting Devices Thereof, Eric Turner, Jian Li, Zixing Wang.
U.S. Appl. No. 14/611,654, filed Feb. 2, 2015, Synthesis of Four Coordinated Platinum Complexes and Their Applications in Light Emitting Devices Thereof, Eric Turner, Jian Li, Zixing Wang.
U.S. Appl. No. 61/329,687, filed Apr. 30, 2010, Synthesis of Four Coordinated Gold Complexes and Their Applications in Light Emitting Devices Thereof, Eric Turner, Jian Li.
U.S. Appl. No. 13/695,338, filed May 16, 2013, Synthesis of Four Coordinated Gold Complexes and Their Applications in Light Emitting Devices Thereof, Eric Turner, Jian Li.
U.S. Appl. No. 61/913,552, filed Dec. 9, 2013, Stable Emitters, Jian Li, Guijie Li.
U.S. Appl. No. 61/969,729, filed Mar. 24, 2014, Efficient Pure Blue OLEDs Employing Tetradentate Pt Complexes with Narrow Spectral Bandwidth, Jian Li, Guijie Li.
U.S. Appl. No. 62/021,488, filed Jul. 7, 2014, Stable and Efficient Platinum Complexes as Red Phosphorescent Emitters, Jian Li, Guijie Li.
U.S. Appl. No. 14/562,195, filed Dec. 5, 2014, Stable Emitters, Jian Li, Guijie Li.
U.S. Appl. No. 61/329,684, filed Apr. 30, 2010, Synthesis of Four Coordinated Palladium Complexes and Their Applications in Light Emitting Devices Thereof, Eric Turner, Jian Li.
U.S. Appl. No. 13/695,337, filed Mar. 13, 2013, Synthesis of Four Coordinated Palladium Complexes and Their Applications in Light Emitting Devices Thereof, Eric Turner, Jian Li.
U.S. Appl. No. 14/145,461, filed Dec. 31, 2013, Synthesis of Four Coordinated Palladium Complexes and Their Applications in Light Emitting Devices Thereof, Eric Turner, Jian Li.
U.S. Appl. No. 15/202,058, filed Jul. 5, 2016, Synthesis of Four Coordinated Palladium Complexes and Their Applications in Light Emitting Devices Thereof, Eric Turner, Jian Li.
U.S. Appl. No. 15/692,660, filed Aug. 31, 2017, Synthesis of Four Coordinated Palladium Complexes and Their Applications in Light Emitting Devices Thereof, Eric Turner, Jian Li.
U.S. Appl. No. 61/444,387, filed Feb. 18, 2011, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 13/399,252, filed Feb. 17, 2012, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 14/332,610, filed Jul. 16, 2014, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 14/589,599, filed Jan. 5, 2015, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 15/243,801, filed Aug. 22, 2016, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 61/490,111, filed May 26, 2011, Synthesis of Platinum and Palladium Complexes as Narrow-Band Phosphorescent Emitters for Full Color Displays, Eric Turner, Jian Li.
U.S. Appl. No. 13/479,921, filed May 24, 2012, Synthesis of Platinum and Palladium Complexes as Narrow-Band Phosphorescent Emitters for Full Color Displays, Eric Turner, Jian Li.
U.S. Appl. No. 14/996,522, filed Jan. 15, 2016, Synthesis of Platinum and Palladium Complexes as Narrow-Band Phosphorescent Emitters for Full Color Displays, Eric Turner, Jian Li.
U.S. Appl. No. 15/640,686, filed Jul. 3, 2017, Synthesis of Platinum and Palladium Complexes as Narrow-Band Phosphorescent Emitters for Full Color Displays, Eric Turner, Jian Li.
U.S. Appl. No. 61/704,880, filed Sep. 24, 2012, Tetradentate Cyclometalated Metal Complexes, Guijie Li, Jian Li.
U.S. Appl. No. 14/430,454, filed Mar. 23, 2015, Metal Compounds, Methods, and Uses Thereof, Guijie Li, Jian Li.
U.S. Appl. No. 15/882,358, filed Jan. 29, 2018, Metal Compounds, Methods, and Uses Thereof, Guijie Li, Jian Li.
U.S. Appl. No. 61/833,091, filed Jun. 10, 2013, Phosphorescent Tetradentate Metal Complexes Having Modified Emission Spectra, Guijie Li, Jason Brooks, Jian Li.
U.S. Appl. No. 61/868,411, filed Aug. 21, 2013, Highly Efficient Organic Electrophosphorescent Devices With "Quantum Dot" Like Emission, Jian Li.
U.S. Appl. No. 14/913,306, filed Feb. 19, 2016, Phosphorescent Tetradentate Metal Complexes Having Modified Emission Spectra, Guijie Li, Jason Brooks, Jian Li.
U.S. Appl. No. 14/513,506, filed Oct. 14, 2014, Platinum Complexes and Devices, Guijie Li, Jason Brooks, Jian Li.
U.S. Appl. No. 15/202,111, filed Jul. 5, 2016, Platinum Complexes and Devices, Guijie Li, Jason Brooks, Jian Li.
U.S. Appl. No. 15/615,566, filed Jun. 6, 2017, Phosphorescent Tetradentate Metal Complexes Having Modified Emission Spectra, Guijie Li, Jason Brooks, Jian Li, Jason Brooks.
U.S. Appl. No. 15/900,260, filed Feb. 20, 2018, Phosphorescent Tetradentate Metal Complexes Having Modified Emission Spectra, Guijie Li, Jason Brooks, Jian Li, Jason Brooks.
U.S. Appl. No. 61/890,545, filed Oct. 14, 2013, Platinum Complexes, Devices, and Uses Thereof, Guijie Li, Jason Brooks, Jian Li.
U.S. Appl. No. 61/890,580, filed Oct. 14, 2013, Platinum Complexes, Devices, and Uses Thereof, Guijie Li, Jason Brooks, Jian Li.
U.S. Appl. No. 61/924,462, filed Jan. 7, 2014, Delayed Fluorescent Emitters Containing Phenyl-Pyrazole and Its Analogues, Guijie Li, Jian Li.
U.S. Appl. No. 14/591,188, filed Jan. 7, 2015, Tetradentate Plantinum and Palladium Complex Emitters Containing Phenyl-Pyrazole and Its Analogues, Guijie Li, Jian Li.
U.S. Appl. No. 61/897,065, filed Oct. 29, 2013, Efficient and Stable Blue and White Organic Light Emitting Diodes, Guijie Li, Jian Li.
U.S. Appl. No. 62/006,509, filed Jun. 2, 2014, Tetradentate Cyclometalated Platinum Complexes Containing 9, 10-Dihydroacridine and Its Analogues, Guijie Li, Jian Li, Zhi-Qiang Zhu.
U.S. Appl. No. 14/728,848, filed Jun. 2, 2015, Tetradentate Cyclometalated Platinum Complexes Containing 9, 10-Dihydroacridine and Its Analogues, Guijie Li, Jian Li, Zhi-Qiang Zhu.
U.S. Appl. No. 62/030,235, filed Jul. 29, 2014, Metal-Assisted Delayed Fluorescent Emitters Containing Tridentated Ligands, Guijie Li, Jian Li.
U.S. Appl. No. 14/809,981, filed Jul. 27, 2015, Metal-Assisted Delayed Fluorescent Emitters Containing Tridentated Ligands, Guijie Li, Jian Li.
U.S. Appl. No. 15/711,525, filed Sep. 21, 2017, Metal-Assisted Delayed Fluorescent Emitters Containing Tridentate Ligands, Guijie Li, Jian Li.
U.S. Appl. No. 62/028,562, filed Jul. 24, 2014, Tetradentate Platinum (II) Complexes Cyclometalated With Functionalized Phenyl Carbene Ligands and Their Analogues, Jian Li, Zhi-Qiang Zhu.
U.S. Appl. No. 14/805,691, filed Jul. 22, 2015 Tetradentate Platinum (II) Complexes Cyclometalated With Functionalized Phenyl Carbene Ligands and Their Analogues, Jian Li, Zhi-Qiang Zhu.
U.S. Appl. No. 62/040,133, filed Aug. 21, 2014, Efficient Cyclometalated Platinum Complexes for Displays and Lighting Applications, Jian Li.
U.S. Appl. No. 62/077,431, filed Nov. 10, 2014, Tetradentate Metal Complexes With Carbon Group Bridging Ligands, Guijie Li, Jian Li.

(56) References Cited

OTHER PUBLICATIONS

U.S. Appl. No. 14/937,318, filed Nov. 10, 2015, Tetradentate Metal Complexes With Carbon Group Bridging Ligands, Guijie Li, Jian Li.

U.S. Appl. No. 62/170,283, filed Jun. 3, 2015, Tetradentate Metal Complexes Containing Napthyridinocarbazole and Its Analogues, Guijie Li, Jian Li.

U.S. Appl. No. 62/254,011, filed Nov. 11, 2015, Tetradentate and Octahedral Metal Complexes Containing Naphthyridinocarbazole and Its Analogues, Guijie Li, Jian Li.

U.S. Appl. No. 15/168,942, filed May 31, 2016, Tetradentate and Octahedral Metal Complexes Containing Naphthyridinocarbazole and Its Analogues, Guijie Li, Jian Li.

U.S. Appl. No. 15/354,280, filed Nov. 17, 2016, Tetradentate and Octahedral Metal Complexes Containing Naphthyridinocarbazole and Its Analogues, Guijie Li, Jian Li.

U.S. Appl. No. 15/882,267, filed Jan. 29, 2018, Tetradentate and Octahedral Metal Complexes Containing Naphthyridinocarbazole and Its Analogues, Guijie Li, Jian Li.

U.S. Appl. No. 62/170,049, filed Jun. 2, 2015, Tetradentate Metal Complexes Containing Indoloacridine and Its Analogues, Jian Li.

U.S. Appl. No. 62/274,456, filed Jan. 4, 2016, Tetradentate Metal Complexes Containing Indoloacridine and Its Analogues, Jian Li.

U.S. Appl. No. 15/168,910, filed May 31, 2016, Tetradentate Metal Complexes Containing Indoloacridine and Its Analogues, Jian Li.

U.S. Appl. No. 15/651,972, filed Jul. 17, 2017 Tetradentate Metal Complexes Containing Indoloacridine and Its Analogues, Jian Li.

U.S. Appl. No. 62/200,960, filed Aug. 4, 2015, Novel Cyclic Tetradentate Platinum (II) and Palladium (II) Complexes, Jian Li, Zhi-Qiang Zhu.

U.S. Appl. No. 15/228,401, filed Aug. 4, 2016 Tetradentate Platinum (II) and Palladium (II) Complexes, Devices, and Uses Thereof, Jian Li, Zhi-Qiang Zhu.

U.S. Appl. No. 62/377,883, filed Aug. 22, 2016, Octahedral Iridium (III) Complexes Employing Azepine Functional Group and Their Analogues, Jian Li, Zhi-Qiang Zhu.

U.S. Appl. No. 15/625,082, filed Jun. 16, 2017, Tetradentate Platinum (II) and Palladium (II) Complexes and Octahedral Iridium Complexes Employing Azepine Functional Groups and Their Analogues, Jian Li, Zhi-Qiang Zhu.

U.S. Appl. No. 62/377,884, filed Aug. 22, 2016, Tetradentate Platinum (II) and Palladium (II) Complexes Employing Azepine Functional Group and Their Analogues, Jian Li, Zhi-Qiang Zhu.

U.S. Appl. No. 62/451,574, filed Jan. 27, 2017, Metal-Assisted Delayed Fluorescent Emitters Employing Pyrido-Pyrrolo-Acridine and Analogues, Jian Li, Yunlong Ji.

U.S. Appl. No. 15/487,476, filed Apr. 14, 2017, OLED With Multi-Emissive Material Layer, Jian Li.

U.S. Appl. No. 62/508,560, filed May 19, 2017, Metal-Assisted Delayed Fluorescent Emitters Employing Benzo-Imidazo-Phenanthridine and Analogues, Jian Li, Yunlong Ji.

U.S. Appl. No. 62/508,849, filed May 19, 2017, Tetradentate Platinum and Palladium Complexes Based on Biscarbazole and Analogues, Jian Li, Zhiqiang Zhu.

U.S. Appl. No. 62/573,596, filed Oct. 17, 2017, Hole-Blocking Materials for Organic Light Emitting Diodes, Jian Li.

U.S. Appl. No. 62/573,472, filed Oct. 17, 2017, Phosphorescent Excimers With Preferred Molecular Orientation as Monochromatic Emitters for Display and Lighting Applications, Jian Li.

U.S. Appl. No. 62/573,639, filed Oct. 17, 2017, Phosphorescent Excimers With Preferred Molecular Orientation as Monochromatic Emitters for Display and Lighting Applications, Jian Li.

U.S. Appl. No. 62/573,462, filed Oct. 17, 2017, Single-Doped White OLED With Extraction Layer Doped With Down-Conversion Red Phosphors, Jian Li.

U.S. Appl. No. 15/845,575, filed Dec. 18, 2017 Organic Light Emitting Diode With Split Emissive Layer, Jian Li, Kody George Klimes.

Zhi-Qiang Zhu et.al., "Harvesting All Electrogenerated Excitons through Metal Assisted Delayed Fluorescent Materials," Adv. Mater. 27 (2015) 2533-2537.

Pui-Keong Chow et al., "Highly luminescent palladium(II) complexes with sub-millisecond blue to green phosphorescent excited states. Photocatalysis and highly efficient PSF-OLEDs," Chem. Sci., 2016, 7, 6083-6098.

Pui Keong Chow et al., "Strongly Phosphorescent Palladium(II) Complexes of Tetradentate Ligands with Mixed Oxygen, Carbon, and Nitrogen Donor Atoms: Photophysics, Photochemistry, and Applications," Angew. Chem. Int. Ed. 2013, 52, 11775-11779.

U.S. Appl. No. 15/947,273, filed Apr. 6, 2018, Platinum Complexes and Devices, Guijie Li, Jason Brooks, Jian Li.

U.S. Appl. No. 16/031,517, filed Jul. 10, 2018, Tetradentate Plantinum and Palladium Complex Emitters Containing Phenyl-Pyrazole and Its Analogues, Guijie Li, Jian Li.

U.S. Appl. No. 15/947,092, filed Apr. 6, 2018, Tetradentate Cyclometalated Platinum Complexes Containing 9, 10-Dihydroacridine and Its Analogues, Guijie Li, Jian Li, Zhi-Qiang Zhu.

U.S. Appl. No. 15/925,084, filed Mar. 19, 2018, US-2018-0219161, Tetradentate Platinum (II) Complexes Cyclometalated With Functionalized Phenyl Carbene Ligands and Their Analogues, Jian Li, Zhi-Qiang Zhu.

U.S. Appl. No. 16/043,908, filed Jul. 24, 2018, Tetradentate Metal Complexes With Carbon Group Bridging Ligands, Guijie Li, Jian Li.

U.S. Appl. No. 15/983,680, filed Aug. 18, 2018, Metal-Assisted Delayed Fluorescent Emitters Employing Benzo-Imidazo-Phenanthridine and Analogues, Jian Li, Yunlong Ji, Linyu Cao.

U.S. Appl. No. 15/984,036, filed May 18, 2018, Tetradentate Platinum and Palladium Complexes Based on Biscarbazole and Analogues, Jian Li, Zhigiang Zhu.

\* cited by examiner

NON-PLATINUM METAL COMPLEXES FOR EXCIMER BASED SINGLE DOPANT WHITE ORGANIC LIGHT EMITTING DIODES

CROSS-REFERENCE TO RELATED APPLICATIONS

This application is a U.S. National Phase Application of International Patent Application No. PCT/US2015/045416 filed on Aug. 14, 2015, which claims the benefit of U.S. Provisional Application Ser. No. 62/037,802 entitled "NON-PLATINUM METAL COMPLEXES FOR EXCIMER BASED SINGLE DOPANT WHITE ORGANIC LIGHT EMITTING DIODES" and filed on Aug. 15, 2014, the contents of both of which are incorporated herein by reference in their entirety.

STATEMENT OF GOVERNMENT INTEREST

This invention was made with government support under DE-EE0005075 awarded by the Department of Energy. The government has certain rights in the invention.

TECHNICAL FIELD

This disclosure relates to non-platinum metal complexes for excimer based single dopant white organic light emitting diodes (OLEDs).

BACKGROUND

Cyclometalated metal complexes can be used for many applications including the development of efficient and high quality organic white lighting devices. One route for achieving organic white lighting devices is development of singly doped white OLEDs by utilizing the excimer properties. Typically the metal complexes used as emissive materials are square-planar platinum complexes.

White organic light emitting diodes (WOLEDs) have shown promise as a potential replacement for existing lighting technologies due to their efficiencies exceeding 100 Lm/W, potential for low cost and scalable production, and compatibility with flexible substrates. Through continuous improvements in device designs and by employing phosphorescent iridium or platinum emitters, WOLEDs with high efficiencies and high color quality have been achieved.

Nevertheless, major challenges still remain, including the deficiency of an efficient and stable phosphorescent blue emitter and the cost prohibitive nature of typical multilayer WOLED structures. The low stability of these devices may be related to the use of blue phosphorescent materials which frequently adopt molecular structures including fluorine groups or 5-membered heterocycles. Complexes cyclometalated with these type of ligands have typically been less stable than iridium complexes cyclometalated with phenyl-pyridine and their analogs, which are known stable and efficient green and red phosphorescent emitters and have been incorporated into commercially viable device settings. Furthermore, the relatively complex multilayer structure typically used in high performance WOLEDs may complicate the goal of low cost fabrication. White devices employing a single emissive platinum complex can achieve emission spanning the visible spectrum while also achieving high efficiencies by utilizing phosphorescent excimers. However, these devices face the same operational lifetime challenges as blue phosphorescent emitters, and platinum and iridium complexes have been unable to yield a WOLED fabricated using a single emissive material with sufficient blue emission, efficient excimer emission, and a molecular design aligned with known stable emitters. For example, while symmetric platinum complexes offer both the rigidity and planar geometry typically necessary for white emission, low operational lifetimes can result from phenyl-azole cyclometalating ligands (e.g., phenyl-azole) and unsuitable device architecture. Moreover, palladium complexes have typically been non emissive or weakly emissive due to at least in part to their low radiative decay rates and low lying metal-centered states providing non-radiative decay pathways, and have not demonstrated efficient excimer emission.

SUMMARY

This disclosure describes the use of non-platinum metal complexes (e.g., palladium, gold, iridium, and rhodium complexes) with efficient excimer emission to provide emitters for white light emitting device applications. The molecular structure of four-coordinating ligands afford the electrochemical and photophysical stability of metal complexes.

In one aspect, disclosed herein is a compound of General Formula I:

General Formula I

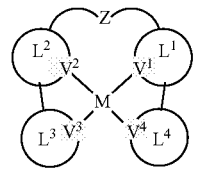

wherein:

M is $Pd^{2+}$, $Ir^+$, $Rh^+$, or $Au^{3+}$;

each of $V^1$, $V^2$, $V^3$, and $V^4$ is coordinated to M and is independently N, C, P, B, or Si;

each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR,

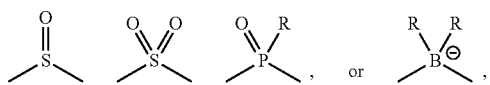

where each R is independently substituted or unsubstituted $C_1$-$C_4$ alkyl or substituted or unsubstituted aryl.

In some implementations, at least one of $V^1$, $V^2$, $V^3$, and $V^4$ is C.

Particular embodiments are described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

Figure 1:
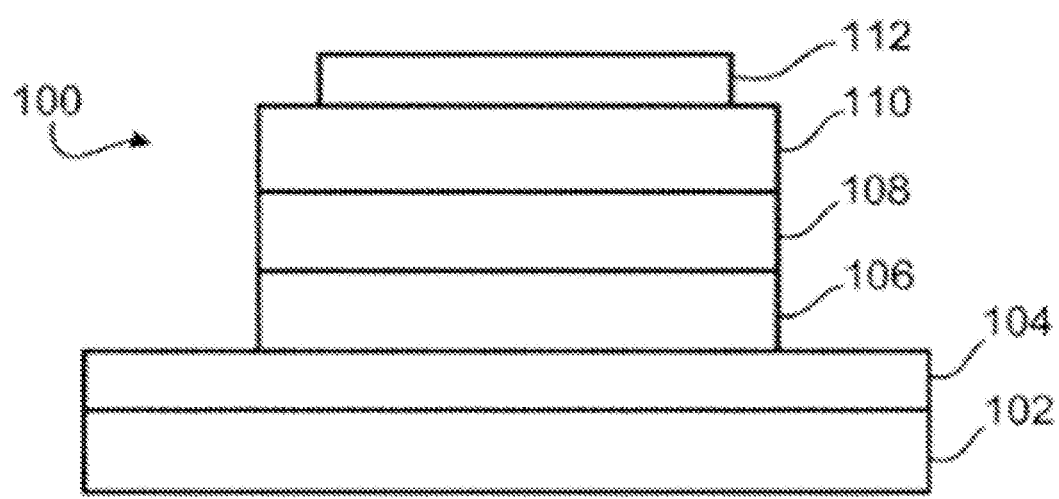
FIG. 1 depicts a cross-sectional view of an exemplary organic light emitting device (OLED).

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of compounds of the present disclosure, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of this disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods described herein.

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus.

Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]n-CH$_3$, —[CH$_2$CH(COOCH$_3$)]n-CH$_3$, —[CH$_2$CH(COO CH$_2$CH$_3$)]n-CH$_3$, and —[CH$_2$CH (COO$^t$Bu)]n-CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

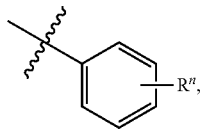

which is understood to be equivalent to a formula:

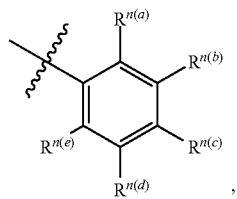

wherein n is typically an integer. That is, $R^n$ is understood to represent up to five independent non-hydrogen substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

In one aspect, disclosed herein is a compound of General Formula I:

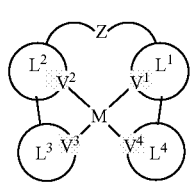

General Formula I wherein:

M is $Pd^{2+}$, $Ir^+$, $Rh^+$, or $Au^{3+}$;

each of $V^1$, $V^2$, $V^3$, and $V^4$ is coordinated to M and is independently N, C, P, B, or Si;

each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR,

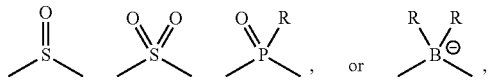

where each R is independently substituted or unsubstituted $C_1$-$C_4$ alkyl or substituted or unsubstituted aryl.

In some implementations, at least one of $V^1$, $V^2$, $V^3$, and $V^4$ is C.

As described herein, General Formula I includes Formulas A1-A20, B1-B8, and C1-C20. For each of these Formulas, unless otherwise noted, when present, M, $V^1$, $V^2$, $V^3$, $V^4$, and Z are as defined above with respect to General Formula I;

each $R^1$, $R^2$, $R^3$, and $R^4$ present represents a non-hydrogen substituent and is independently substituted or unsubstituted $C_1$-$C_4$ alkyl or substituted or unsubstituted aryl; each n is independently an integer of 0 to the maximum value permitted by valency (e.g., 3, 4, 5);

each Y present (e.g, $Y^{1a}$, $Y^{2a}$, $Y^{1b}$, $Y^{2b}$, $Y^{3a}$, $Y^{3b}$, $Y^{4a}$, and $Y^{4b}$) is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl;

U is O, S, NR, PR, AsR, $CR_2$, $SiR_2$, or BR, where each R is hydrogen, halogen, alkyl, alkenyl, alkynyl, and aryl; and X indicates the larger ring structure.

For compounds of Formulas A1-A20, M is $Pd^{2+}$. For compounds of Formulas A13-A20, Z is

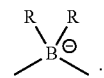

Compounds of Formula A1 have the following structure:

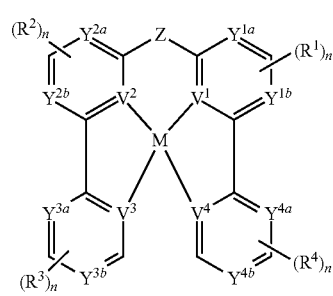

Formula A1

Compounds of Formula A2 have the following structure:

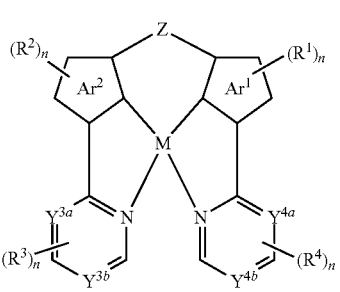

Formula A2 wherein:
each

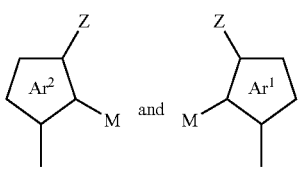

is independently selected from the group consisting of:

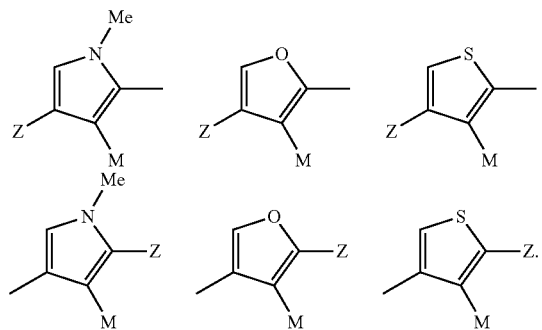

Compounds of Formula A3 have the following structure:

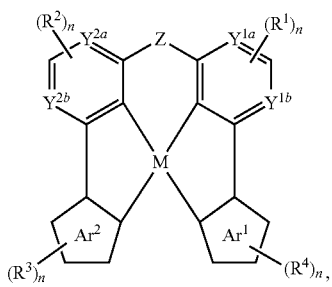

Formula A3 wherein each

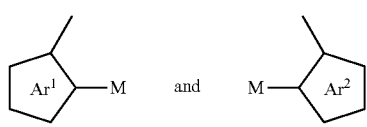

is independently selected from the group consisting of

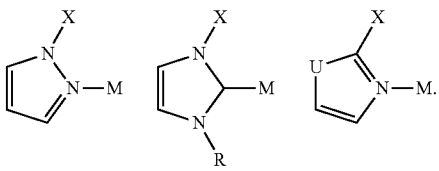

Compounds of Formulas A4-A6 have the following structures:

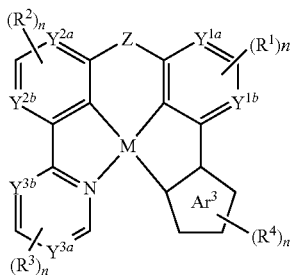

Formula A4

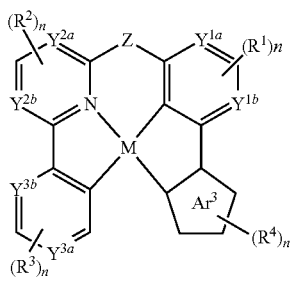

Formula A5

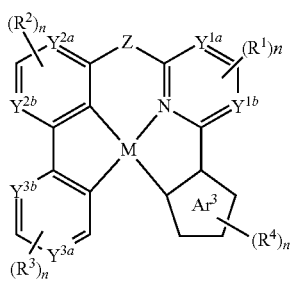

Formula A6 wherein

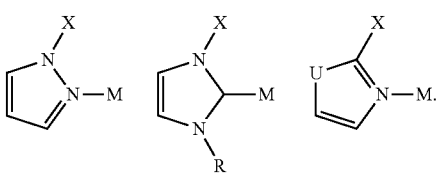

is selected from the group consisting of

Compounds of Formulas A7-A8 have the following structures:
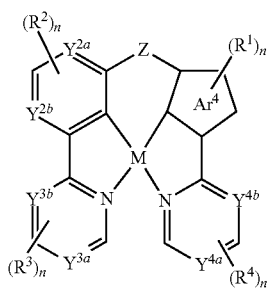
Formula A7
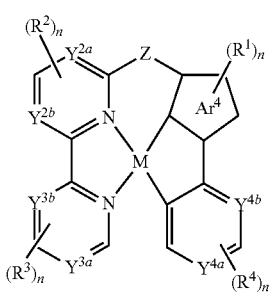
Formula A8
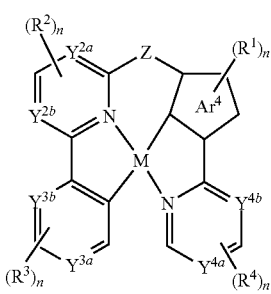
Formula A9
wherein
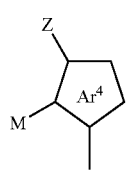
is selected from the group consisting of
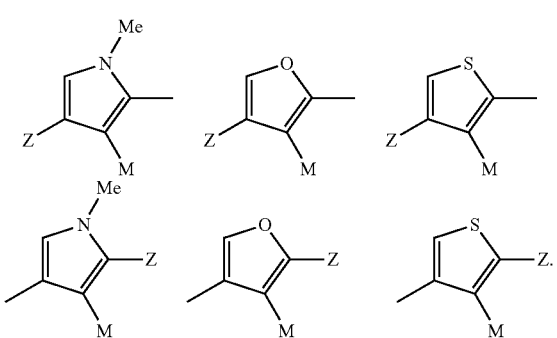
Compounds of Formulas A10 and A11 have the following structures:
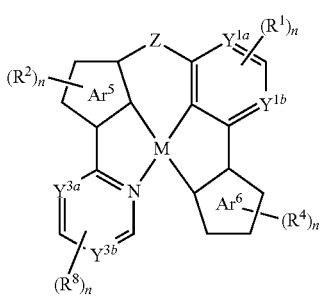
Formula A10
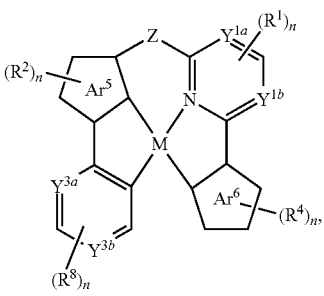
Formula A11
wherein
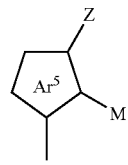
is selected from the group consisting of
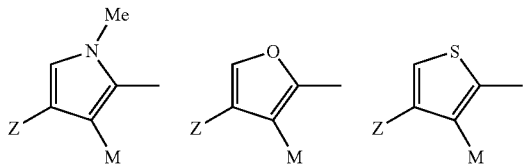
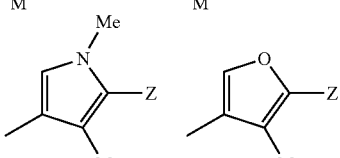
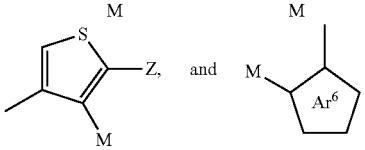
is selected from the group consisting of
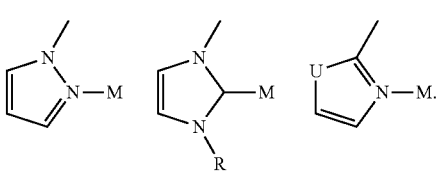

Compounds of Formula A12 have the following structure:
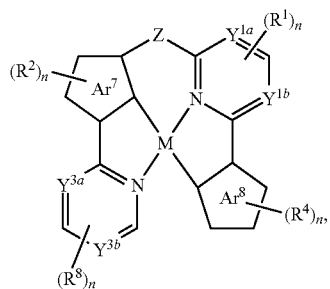
Formula A12
wherein
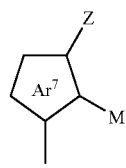
is selected from the group consisting of
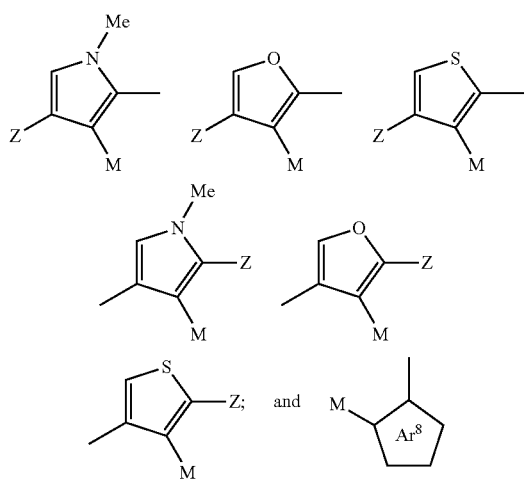
and
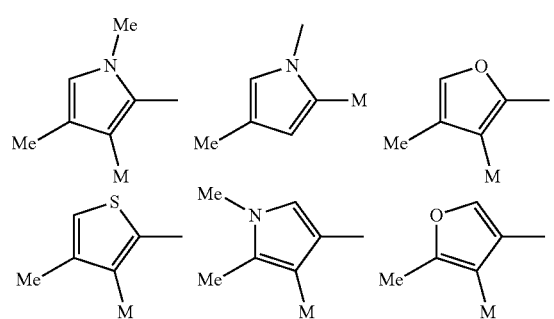
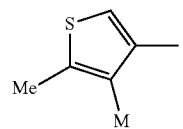
As noted above, for Formulas A13-A20, Z is
Compounds of Formula A13 have the following structure:
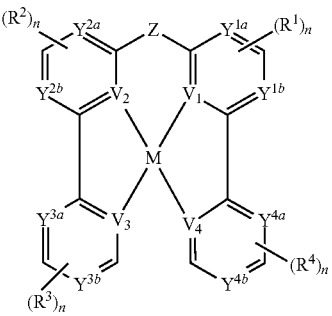
Formula A13
Compounds of Formula A14 have the following structure:
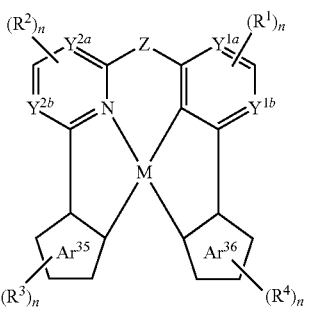
Formula A14
wherein each
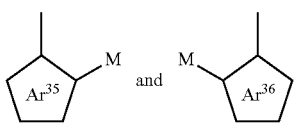
is independently selected from the group consisting of
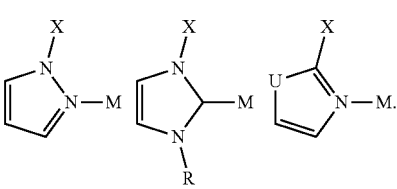

Compounds of Formulas A15-A17 have the following structures:
Formula A15
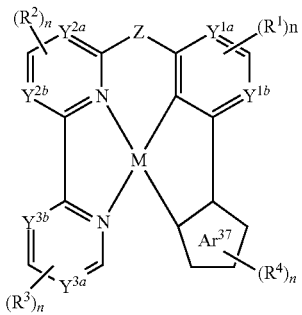
Formula A16
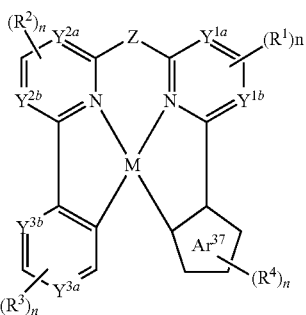
Formula A17
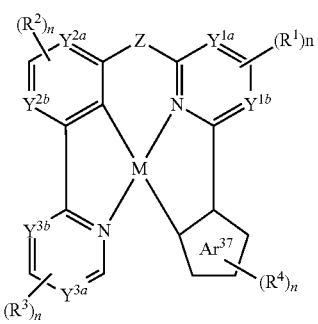
wherein
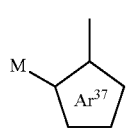
is selected from the group consisting of
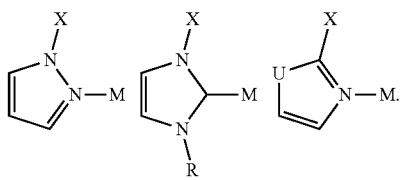
Compounds of Formula A18 have the following structure:
Formula A18
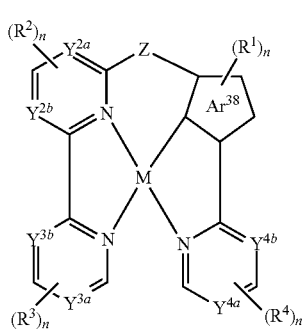
wherein
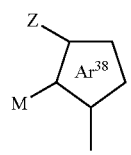
is selected from the group consisting of
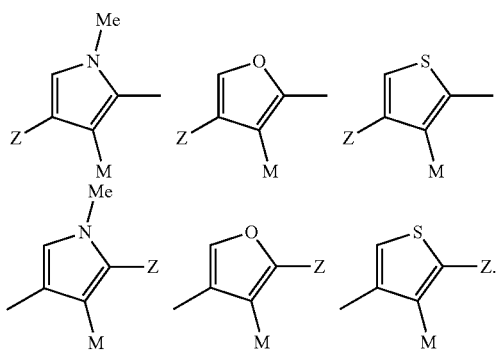
Compounds of Formula A19 have the following structure:
Formula A19
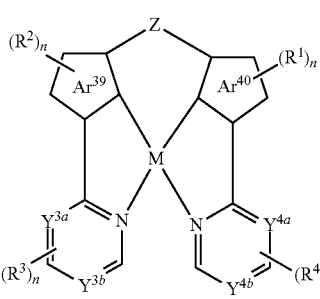
wherein
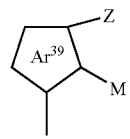

is selected from the group consisting of

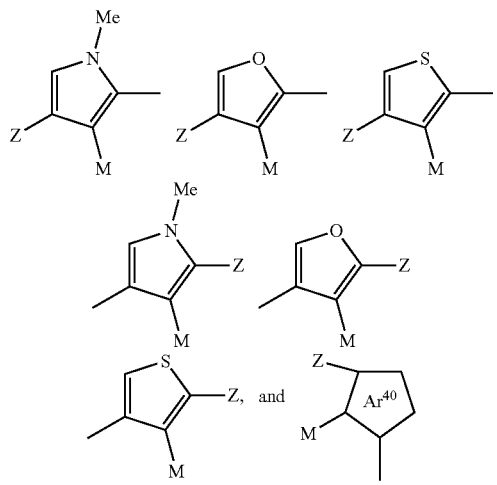

is selected from the group consisting of

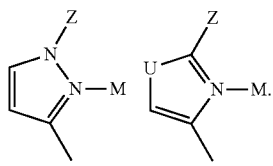

Compounds of Formula A20 have the following structure:

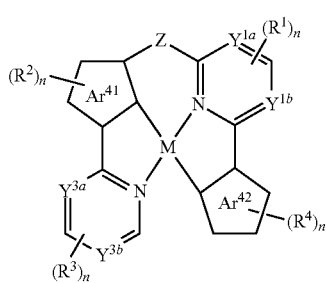

Formula A20 wherein

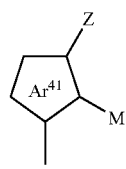

is selected from the group consisting of

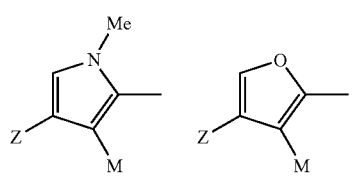

-continued

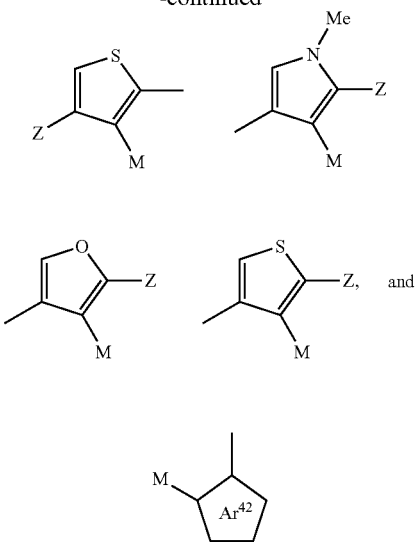

is selected from the group consisting of

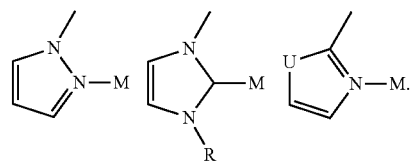

In compounds of Formulas B1-B8, M is $Ir^+$ or $Rh^+$.

Compounds of Formula B1 have the following structure:

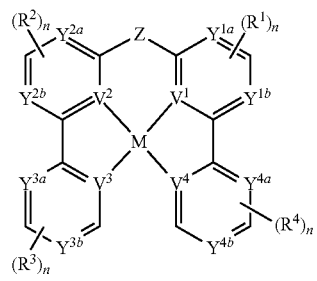

Formula B1

Compounds of Formulas B2-B4 have the following structures:

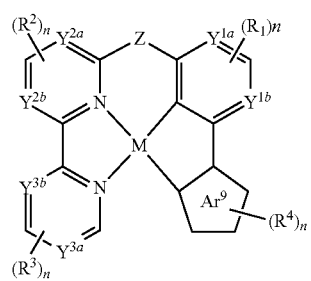

Formula B2

-continued

Formula B3
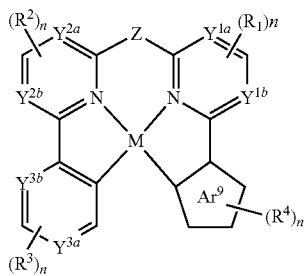

Formula B4
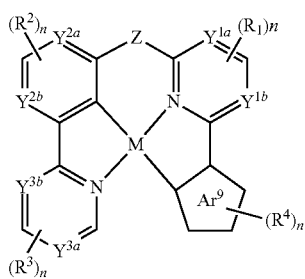

wherein

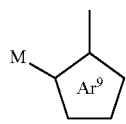

is selected from the group consisting of

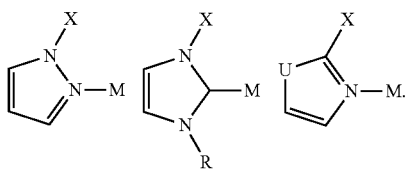

Compounds of Formula B5 have the following structure:

Formula B5
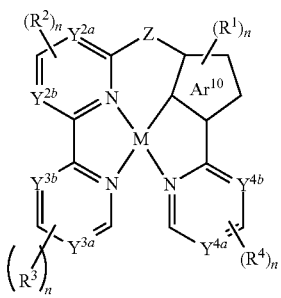

wherein

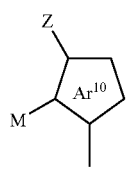

is selected from the group consisting of

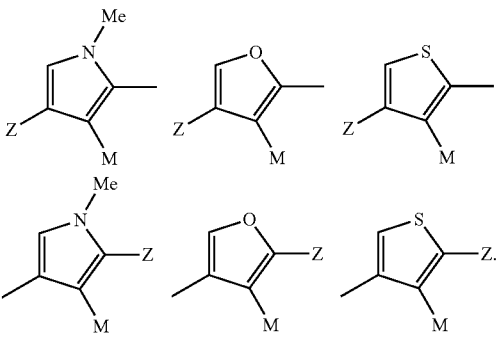

Compounds of Formula B6 have the following structure:

Formula B6
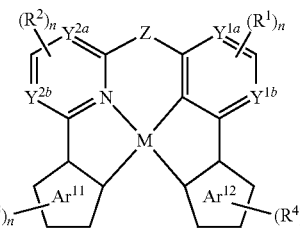

wherein each

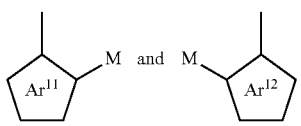

is independently selected from the group consisting of

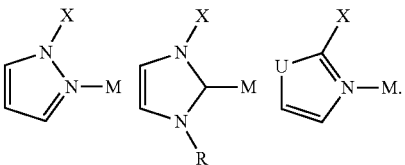

Compounds of Formula B7 have the following structure:

Formula B7
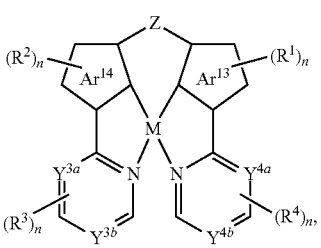

wherein

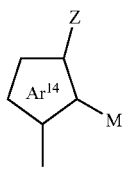

is selected from the group consisting of

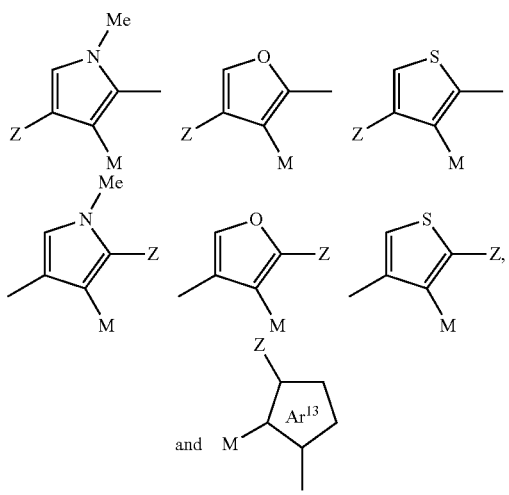

is selected from the group consisting of

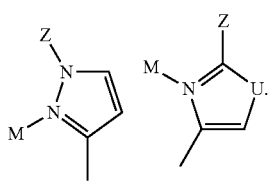

Compounds of Formula B8 have the following structure:

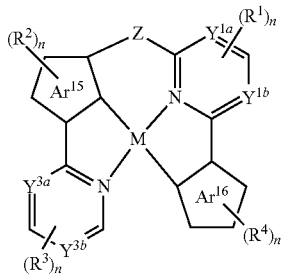

Formula B8 wherein

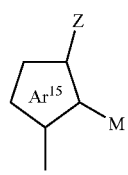

is selected from the group consisting of:

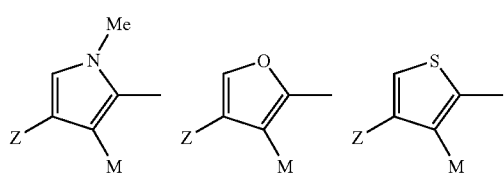

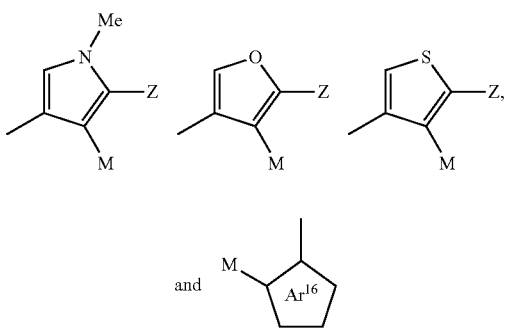

is selected from the group consisting of:

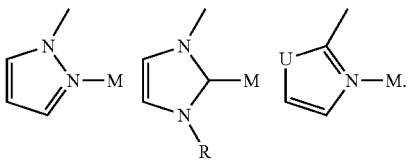

In compounds of Formulas C1-C20, M is Au$^{3+}$. For Formulas C9-C20, Z is

Compounds of Formula C1 have the following structure:

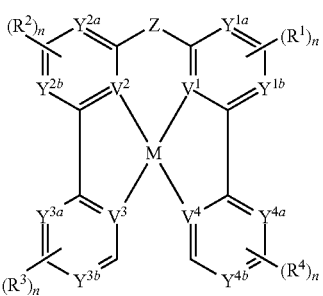

Formula C1

Compounds of Formula C2 have the following structure:

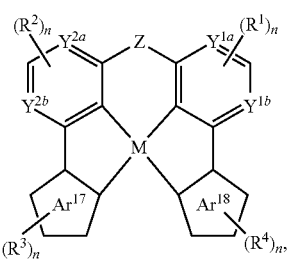

Formula C2 wherein
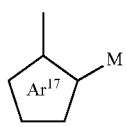
is selected from the group consisting of:
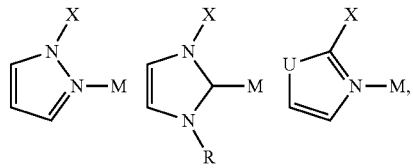
wherein
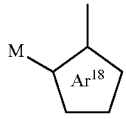
is selected from the group consisting of:
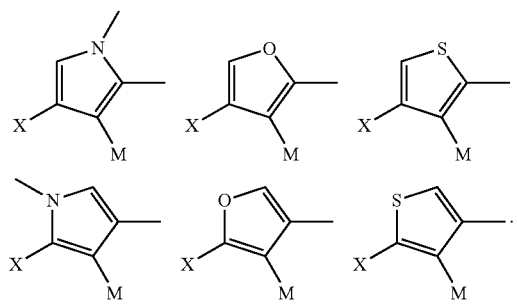
Compounds of Formula C3 have the following structure:
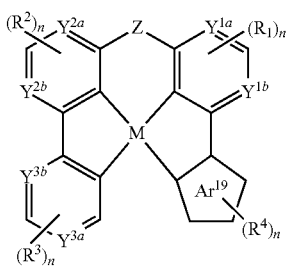
Formula C3
wherein
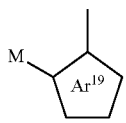
is selected from the group consisting of
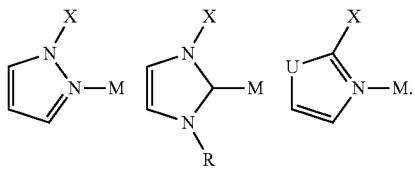
Compounds of Formulas C4-C6 have the following structures:
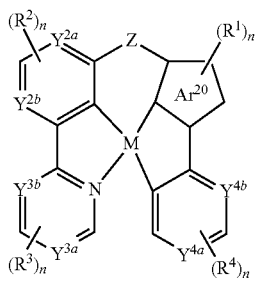
Formula C4
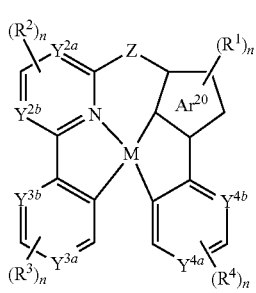
Formula C5
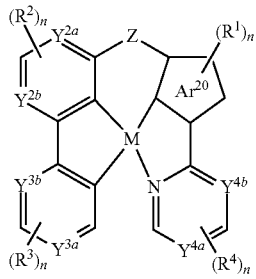
Formula C6
wherein
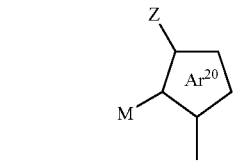
is selected from the group consisting of
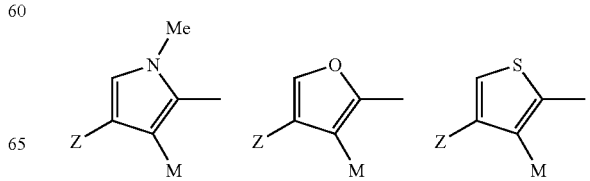

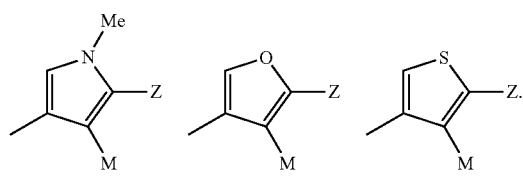
Compounds of Formula C7 have the following structure:
Formula C7
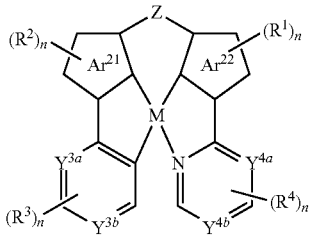
wherein each of
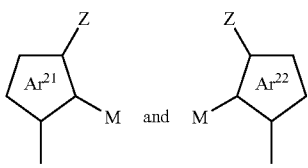
is independently selected from the group consisting of
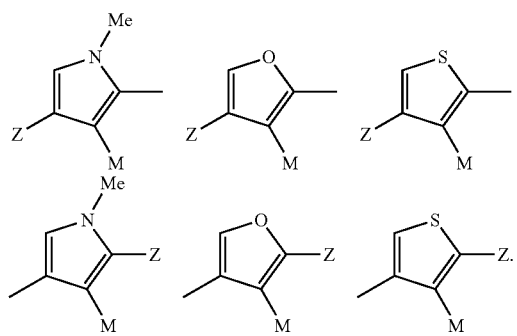
Compounds of Formula C8 have the following structure:
Formula C8
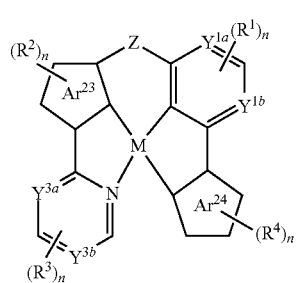
wherein
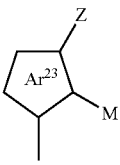
is selected from the group consisting of
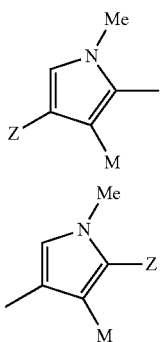
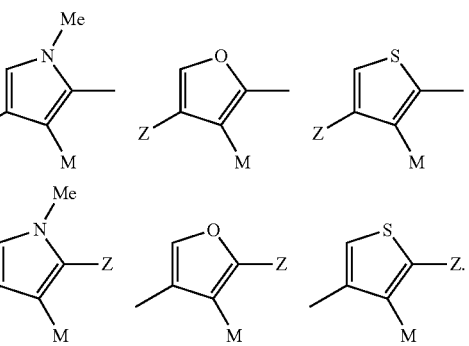
wherein
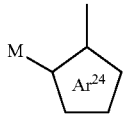
is selected from the group consisting of
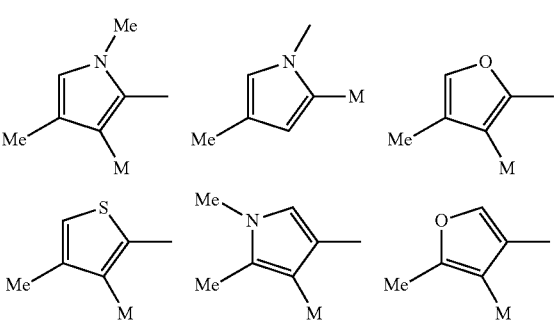
As noted above, for Formulas C9-C20, Z is
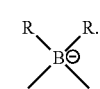

Compounds of Formula C9 have the following structure:

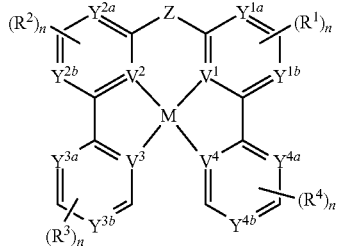

Formula C9

Compounds of Formula C10 have the following structure:

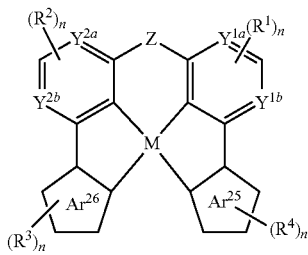

Compound C10 wherein each

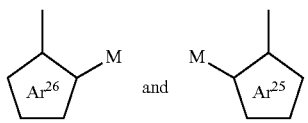

is independently selected from the group consisting of

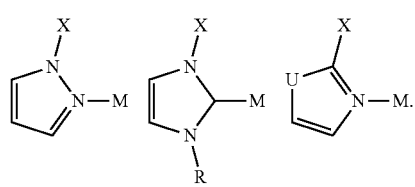

Compounds of Formulas C11-C13 have the following structures:

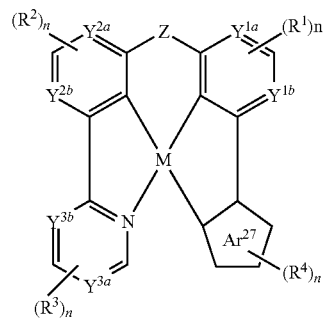

Formula C11

-continued

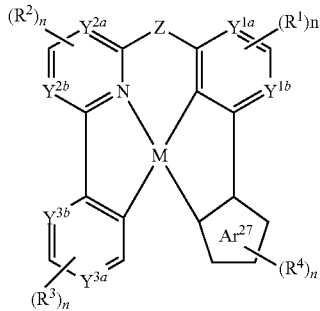

Formula C12

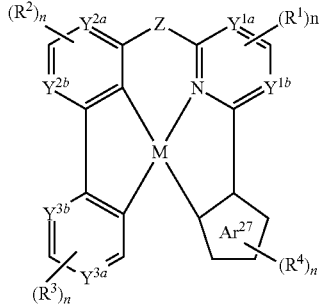

Formula C13 wherein is selected from the group consisting of

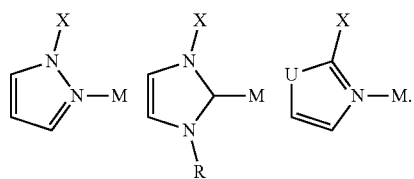

Compounds of Formulas C13-C15 have the following structures:

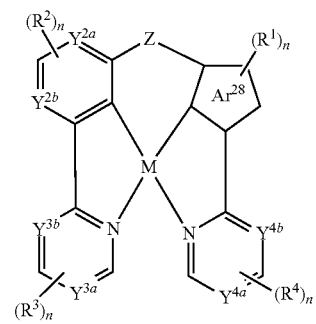

Formula C13

Formula C14
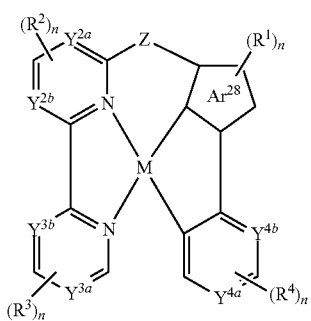
Formula C15
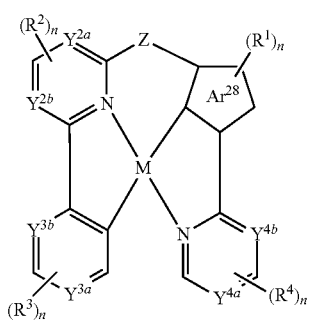
wherein
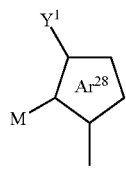
is selected from the group consisting of
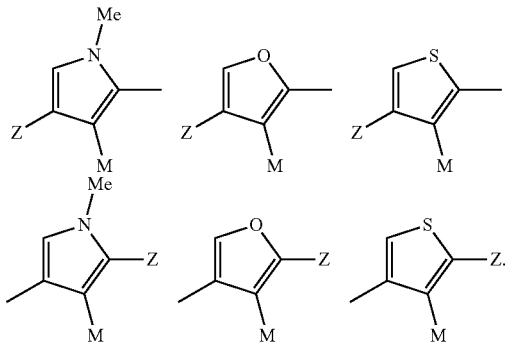
Compounds of Formula C16 have the following structure:
Formula C16
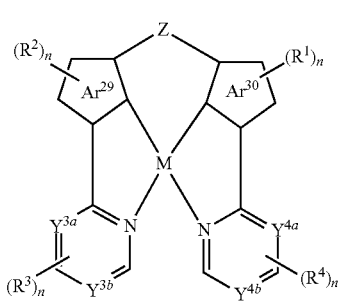
wherein each
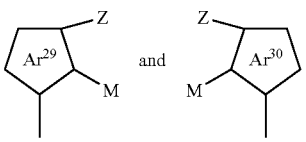
is independently selected from the group consisting of
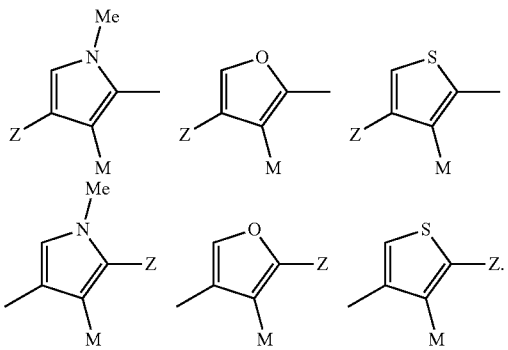
Compounds of Formulas C17 and C18 have the following structures:
Formula C17
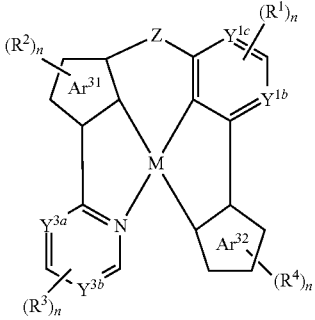
Formula C18
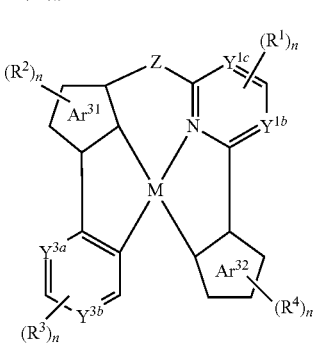
wherein
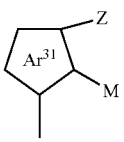

is selected from the group consisting of
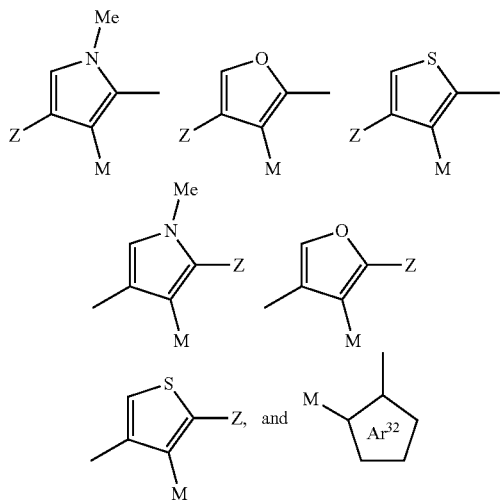
is selected from the group consisting of
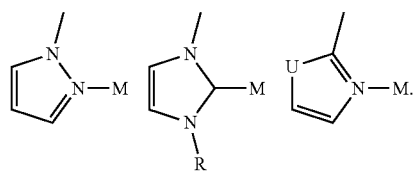
Compounds of Formula C19 have the following structure:
Formula C19
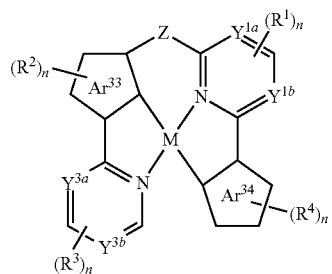
wherein
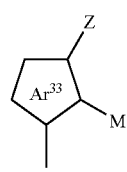
is selected from the group consisting of
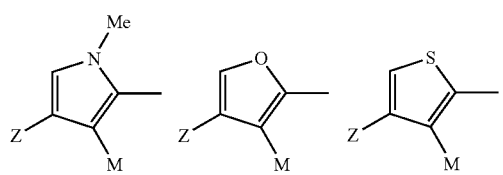
is selected from the group consisting of
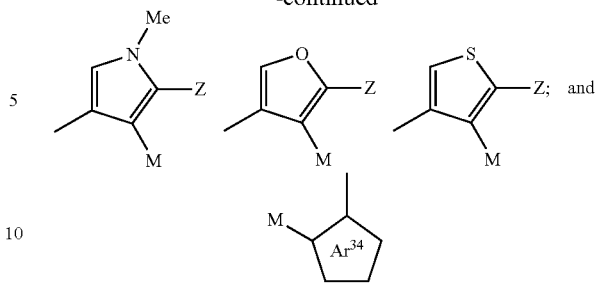
is selected from the group consisting of
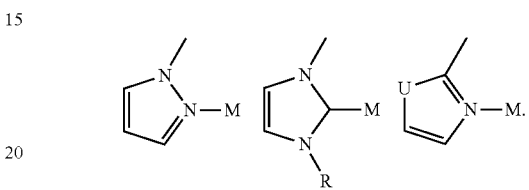
A compound of General Formula I may have one of the following structures:
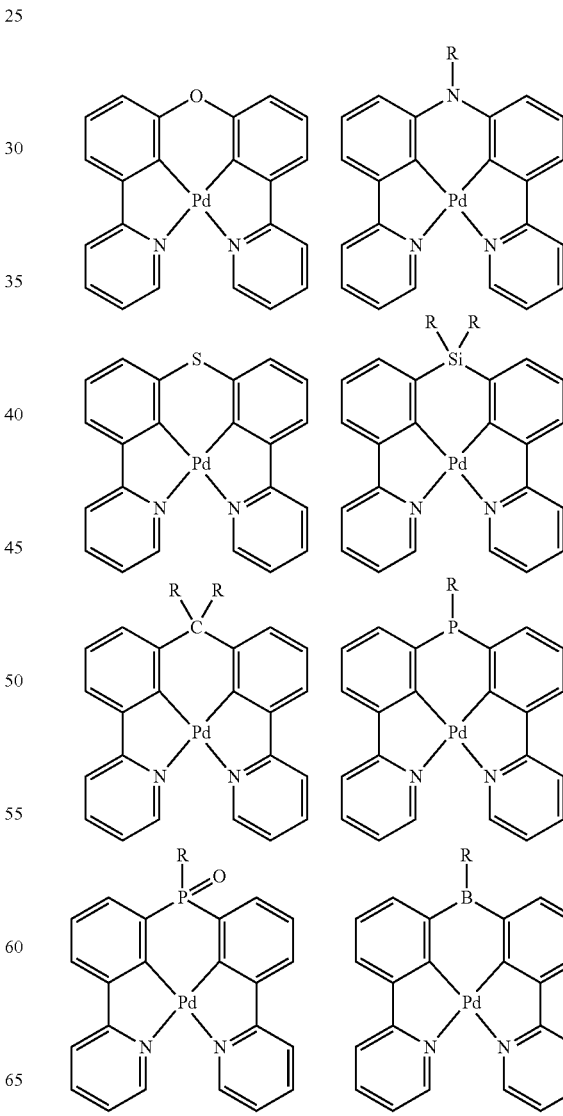

35
-continued
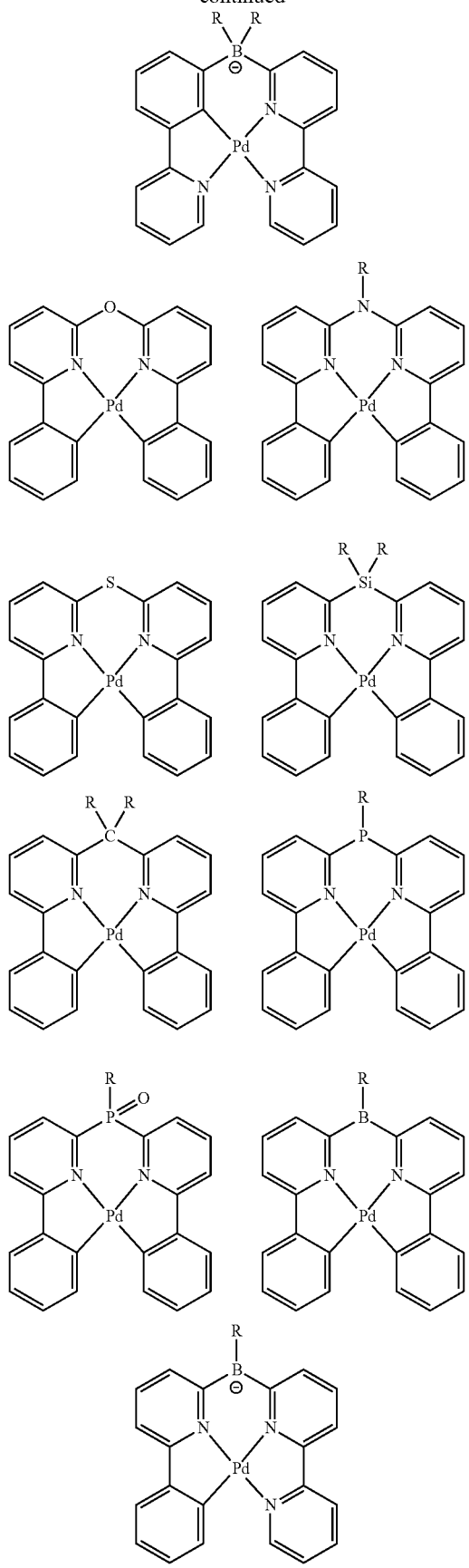
36
-continued
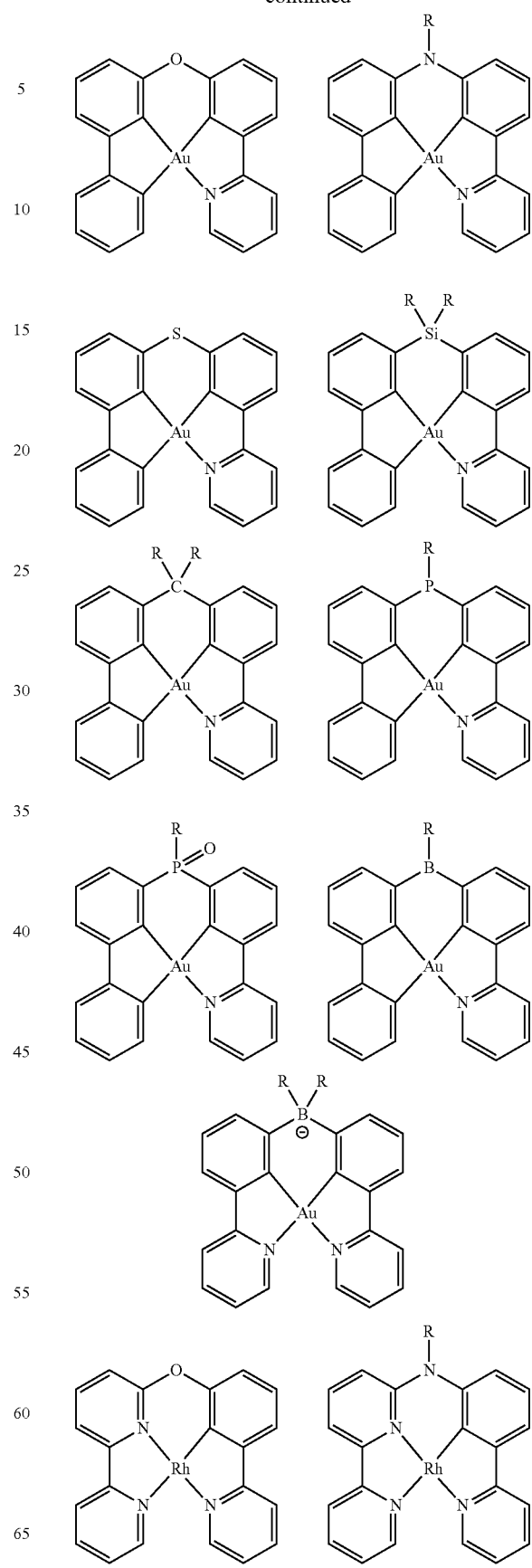

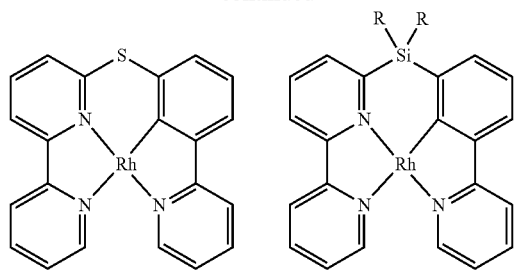
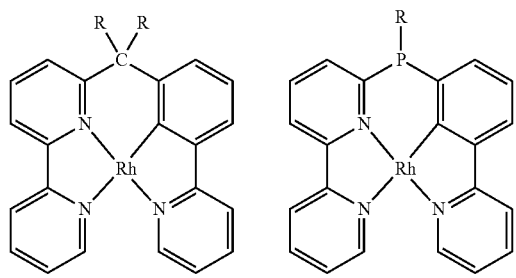
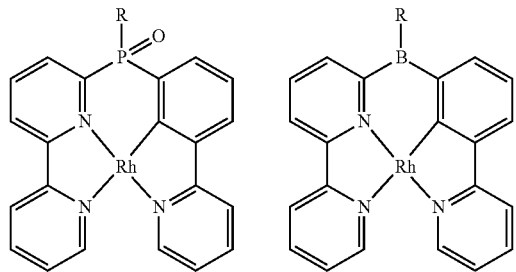
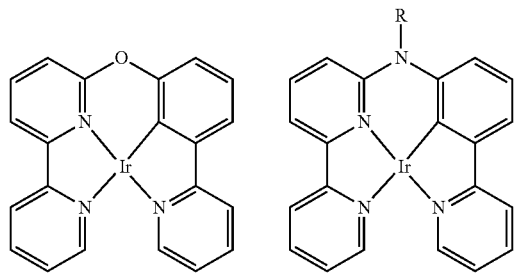
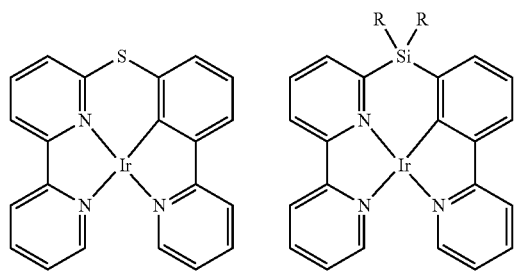
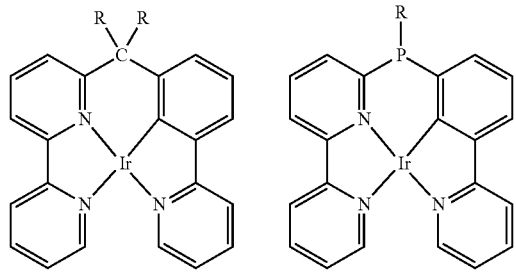
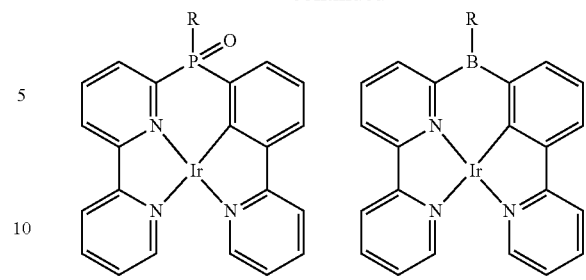
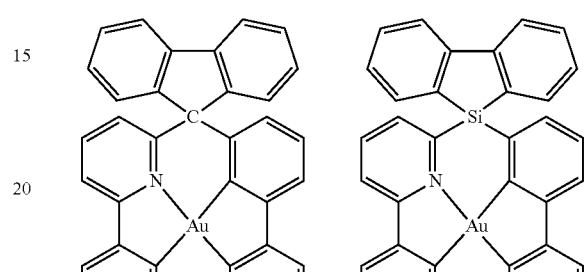
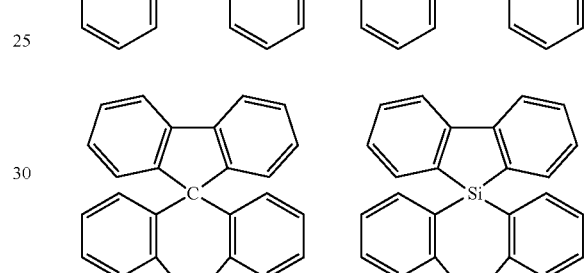
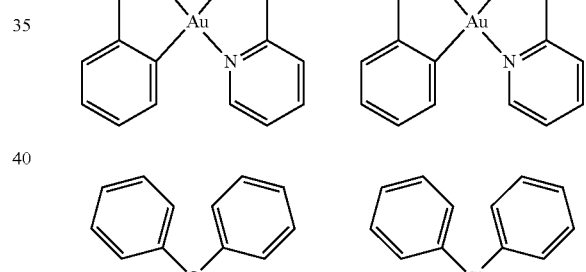
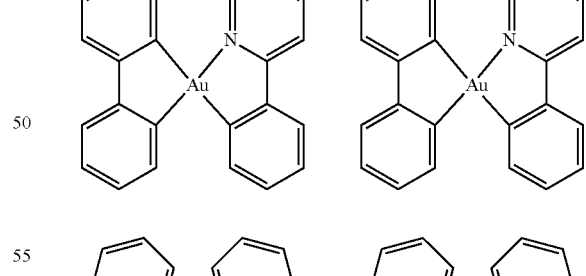
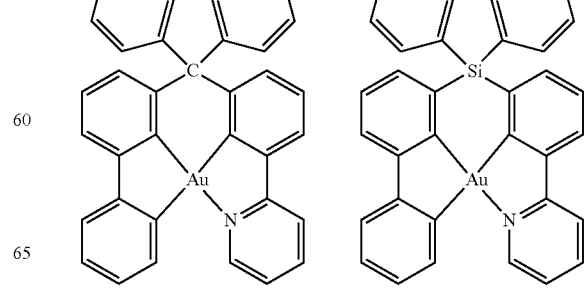

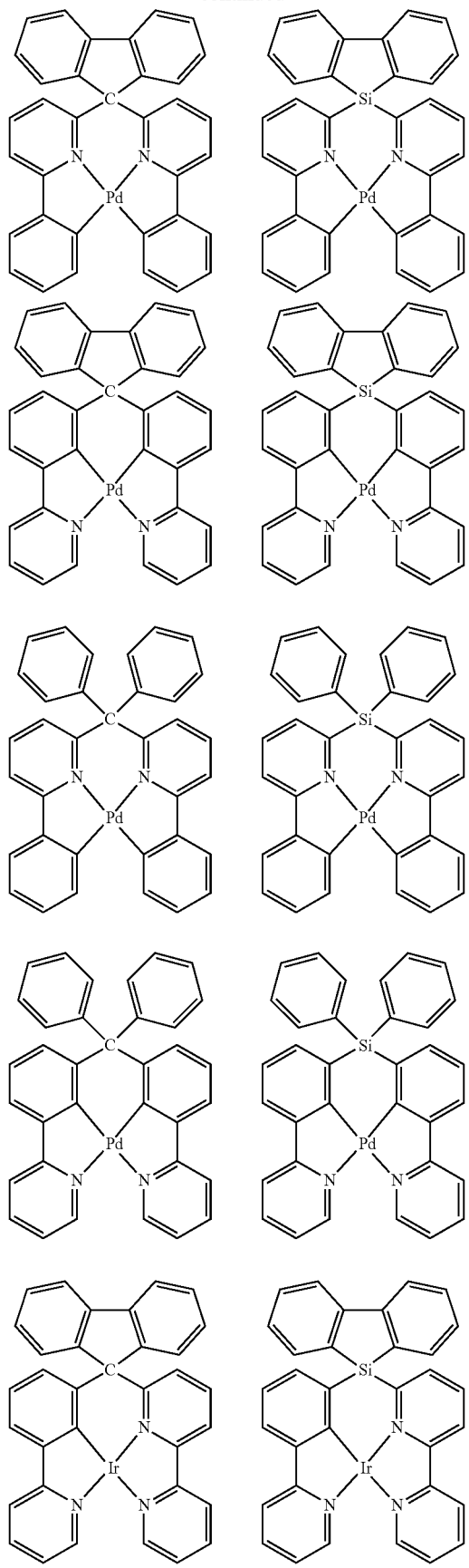
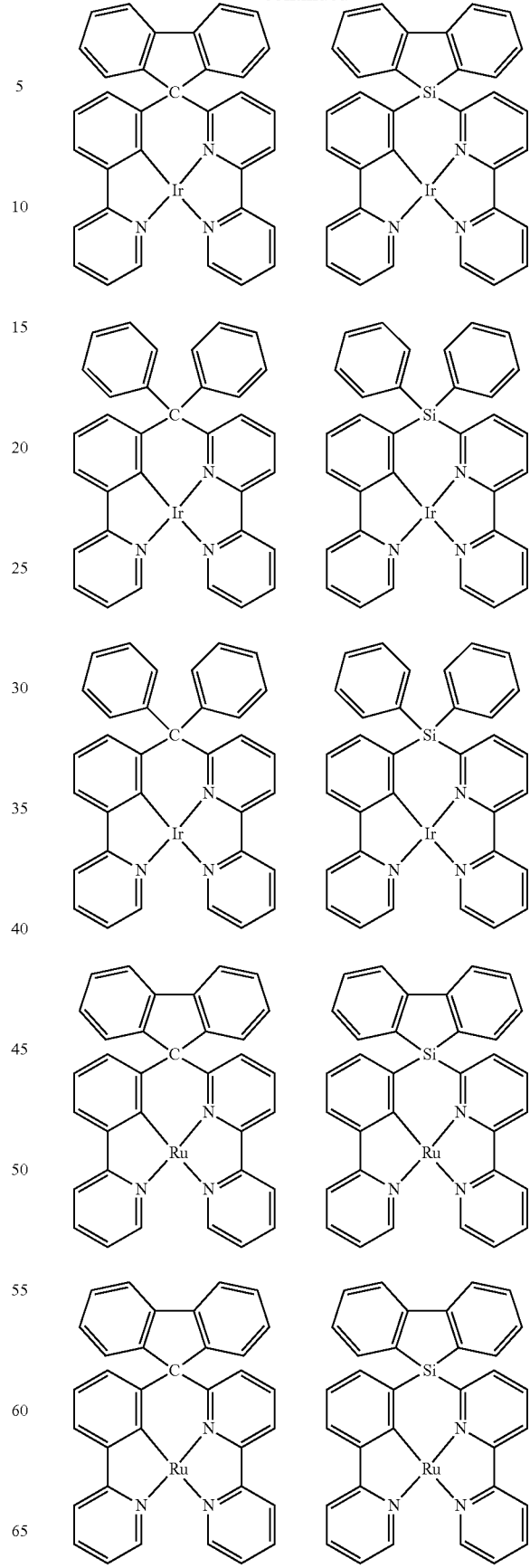

-continued

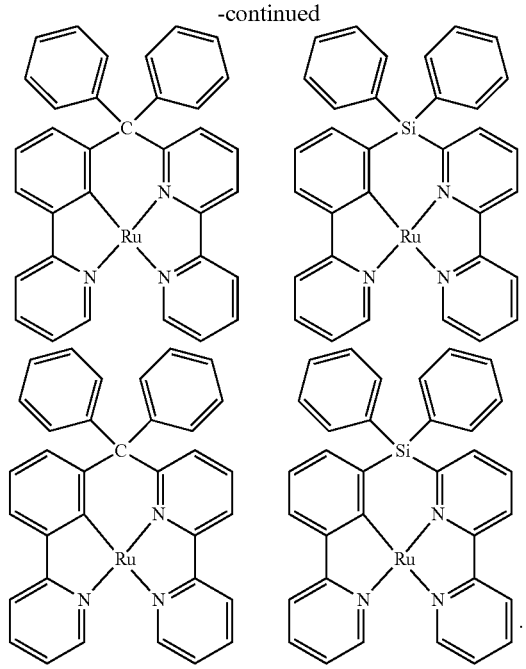

As described herein, General Formula I includes General Formulas 1-5. For each of these General Formulas, unless otherwise noted, when present, M, $V^1$, $V^2$, $V^3$, $V^4$, and Z are as defined above with respect to General Formula I;

each $R^1$, $R^2$, $R^3$, and $R^4$ present represents a non-hydrogen substituent and is independently substituted or unsubstituted $C_1$-$C_4$ alkyl or substituted or unsubstituted aryl;

each n is independently an integer of 0 to the maximum value permitted by valency (e.g., 3, 4, 5); and each Y present (e.g., $Y^{1a}$, $Y^{2a}$, $Y^{1b}$, $Y^{2b}$, $Y^{3a}$, $Y^{3b}$, $Y^{4a}$, $Y^{4b}$, etc.) is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl.

Compounds of General Formula 1 have the following structure:

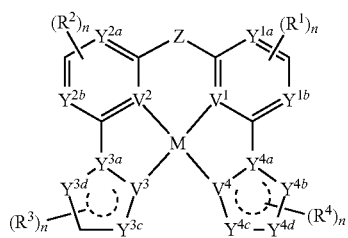

General Formula 1 wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 3, valency permitting; and each of $Y^{1a}$, $Y^{2a}$, $Y^{1b}$, $Y^{2b}$, $Y^{3a}$, $Y^{3c}$, $Y^{3d}$, $Y^{4a}$, $Y^{4b}$, $Y^{4c}$, $Y^{4d}$ is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl.

A compound of General Formula 1 may have one of the following structures:

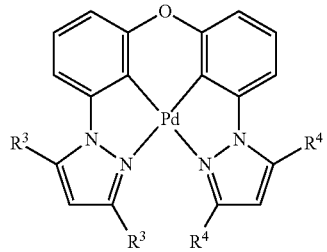

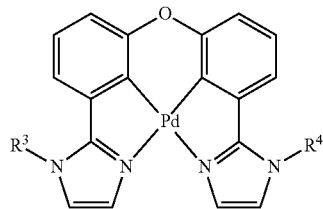

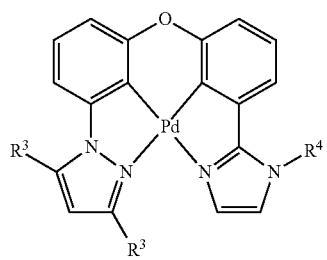

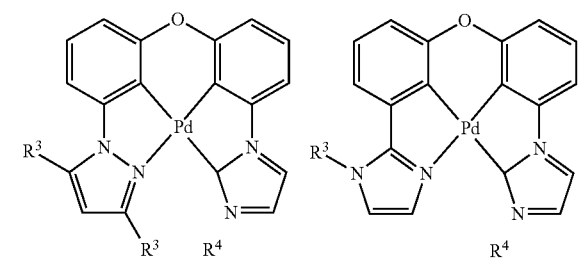

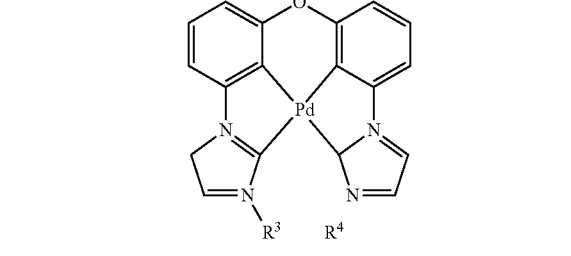

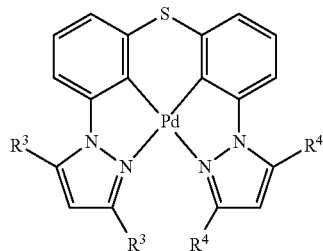

-continued
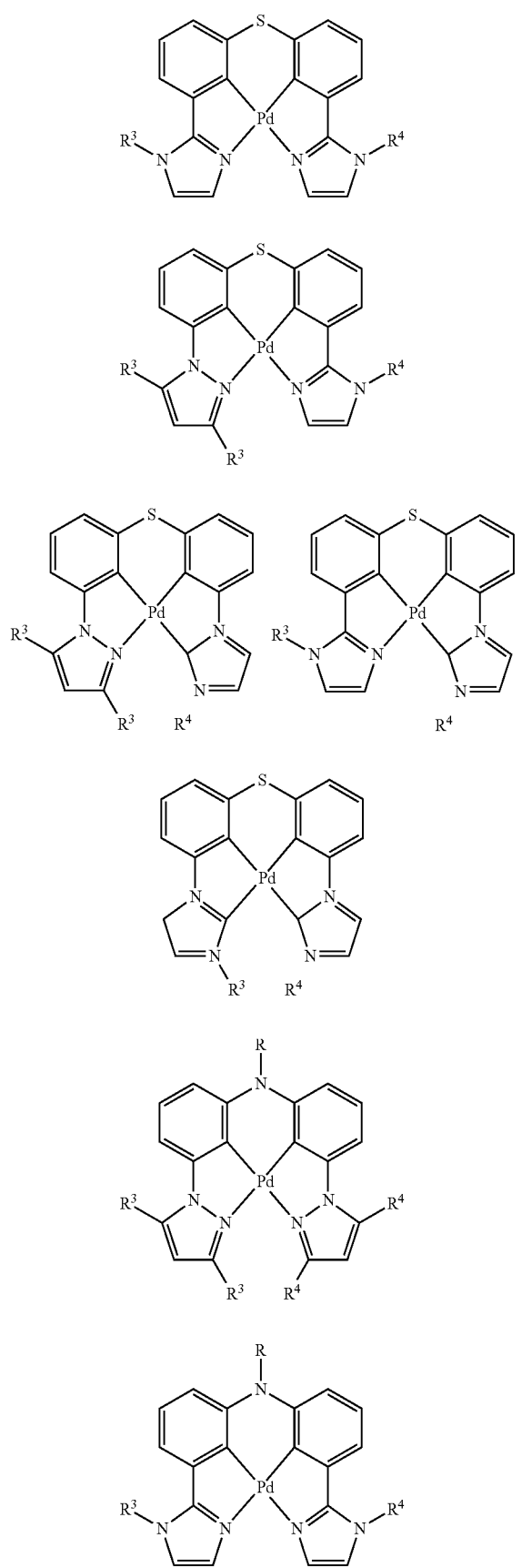
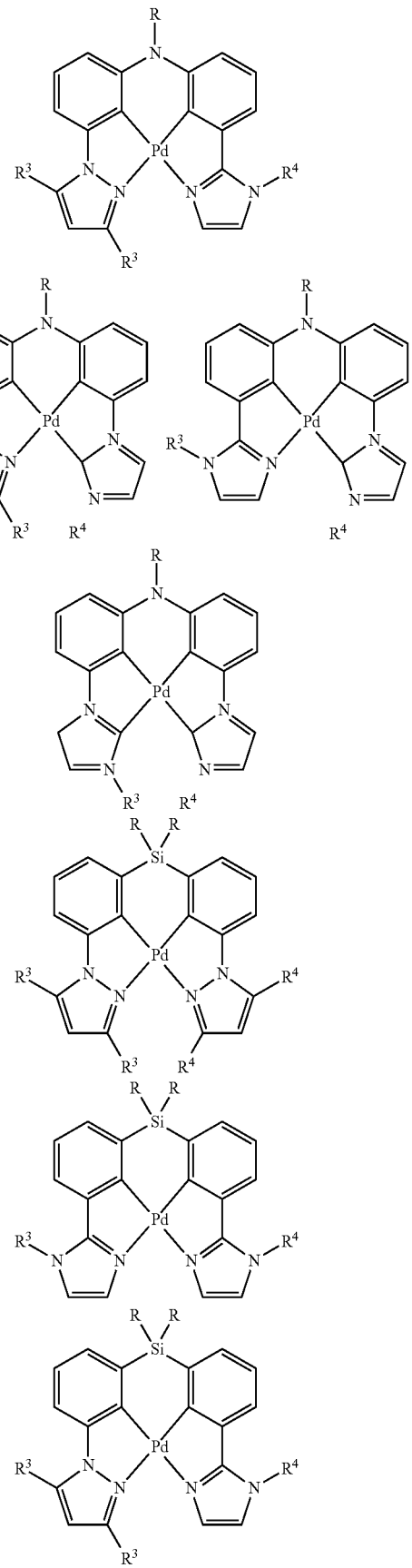

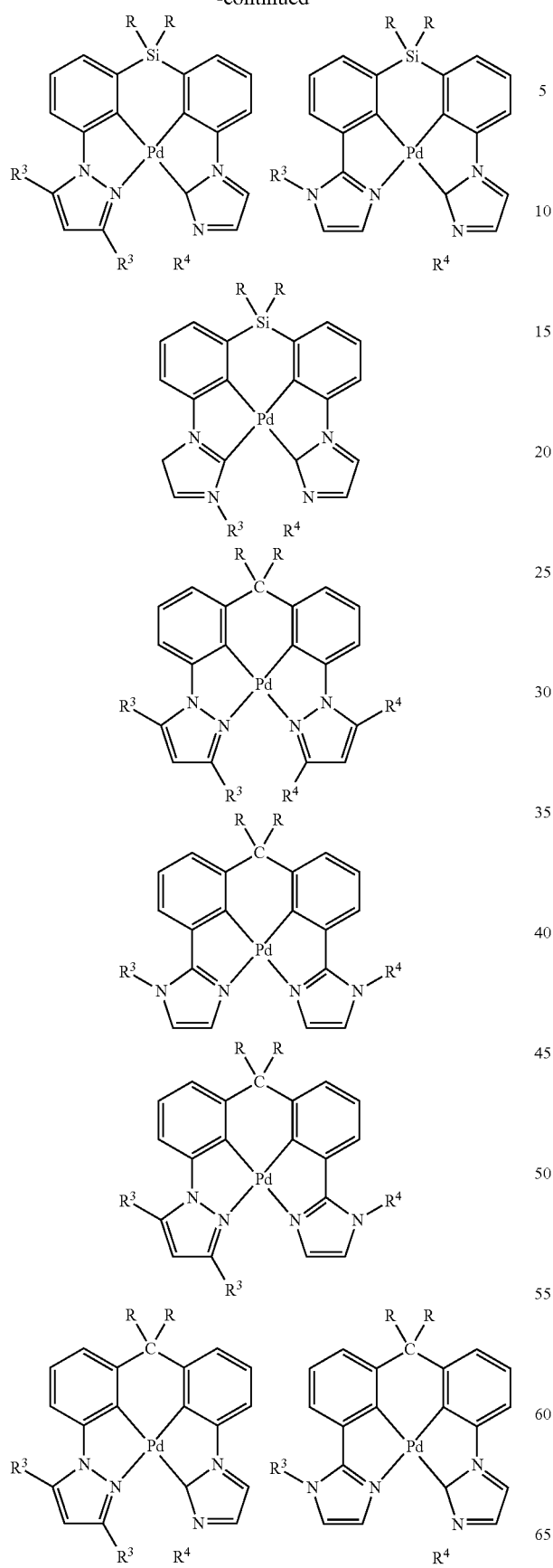
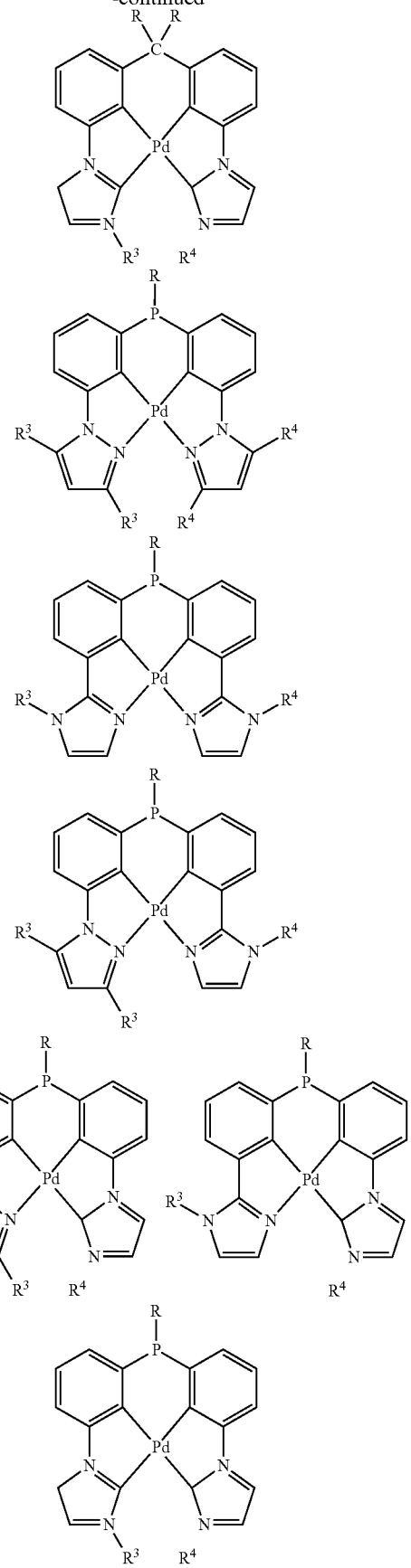

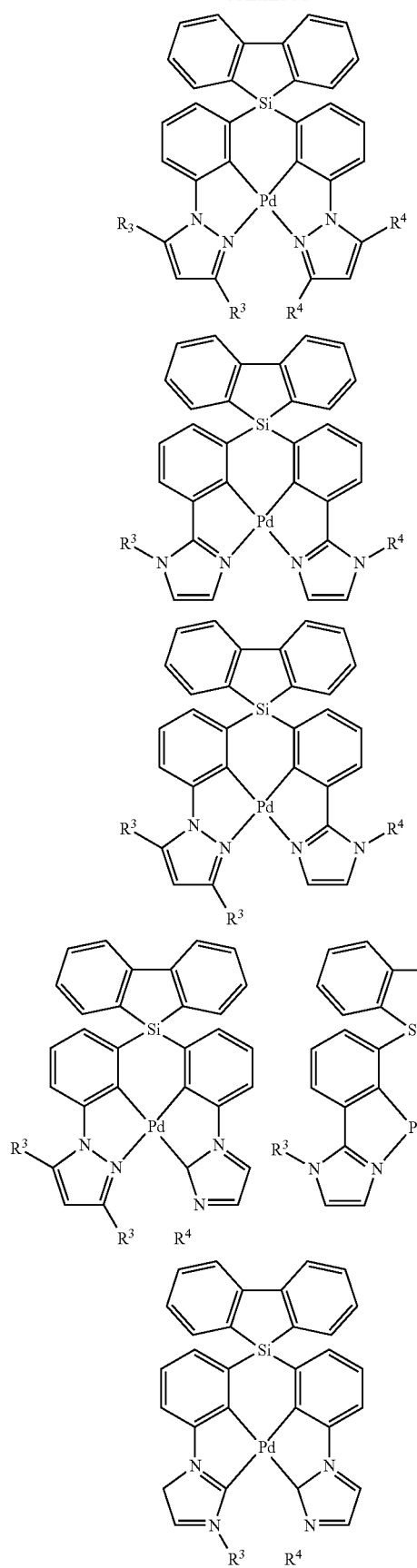
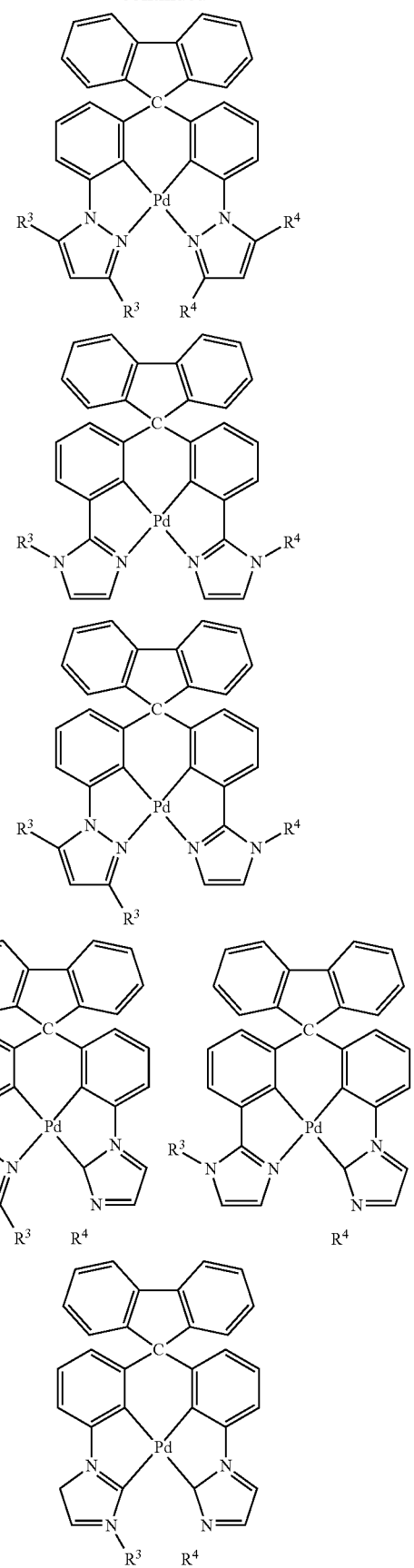

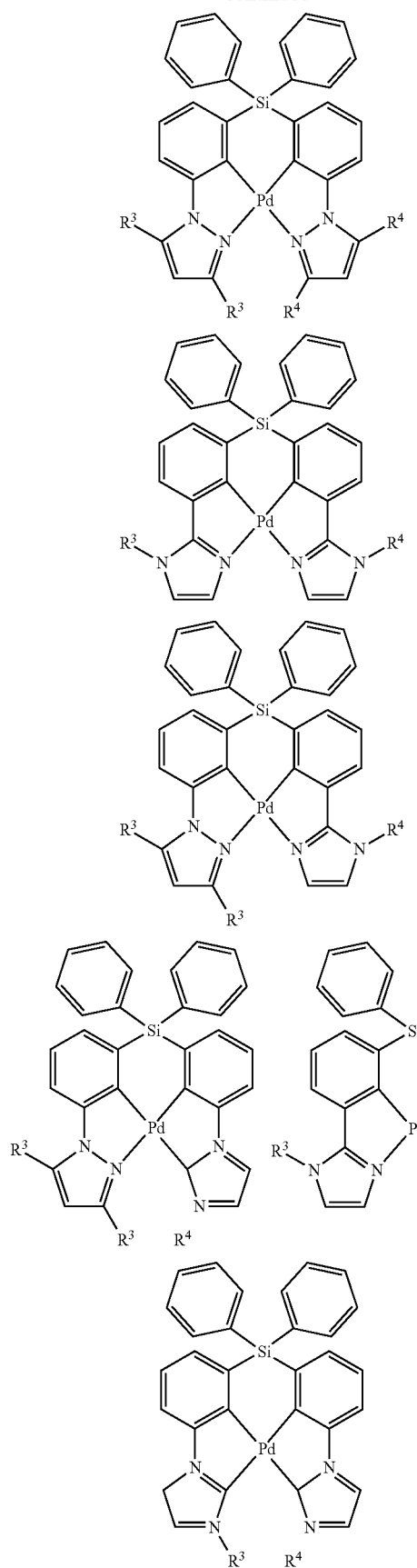
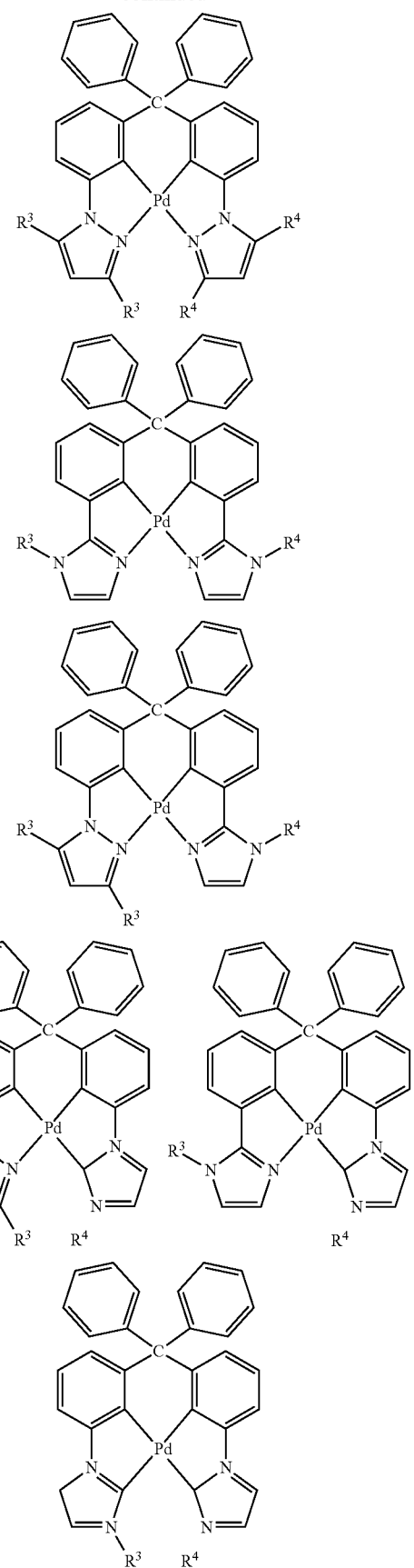

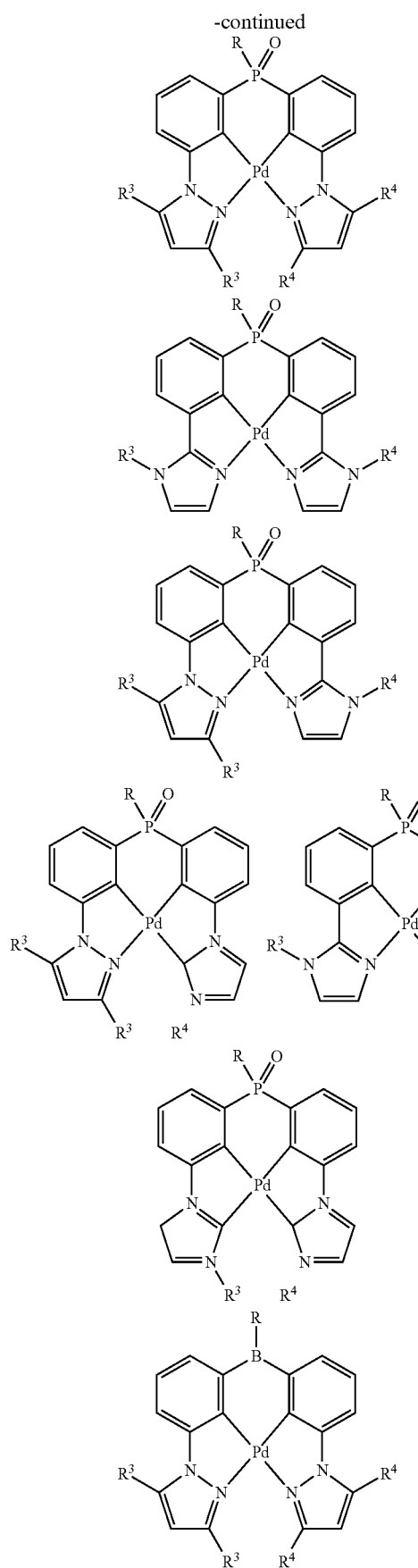
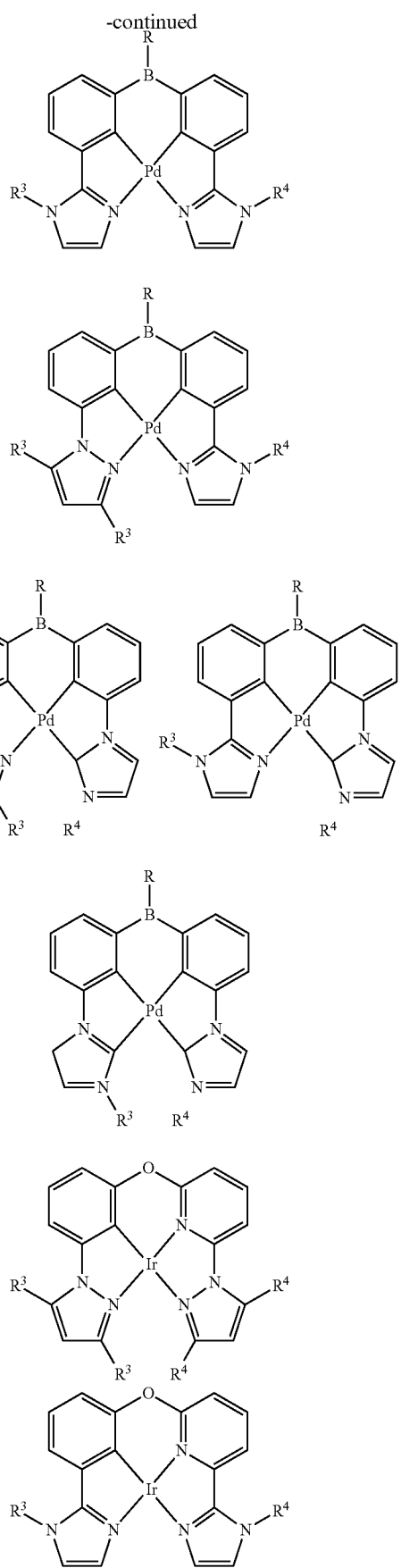

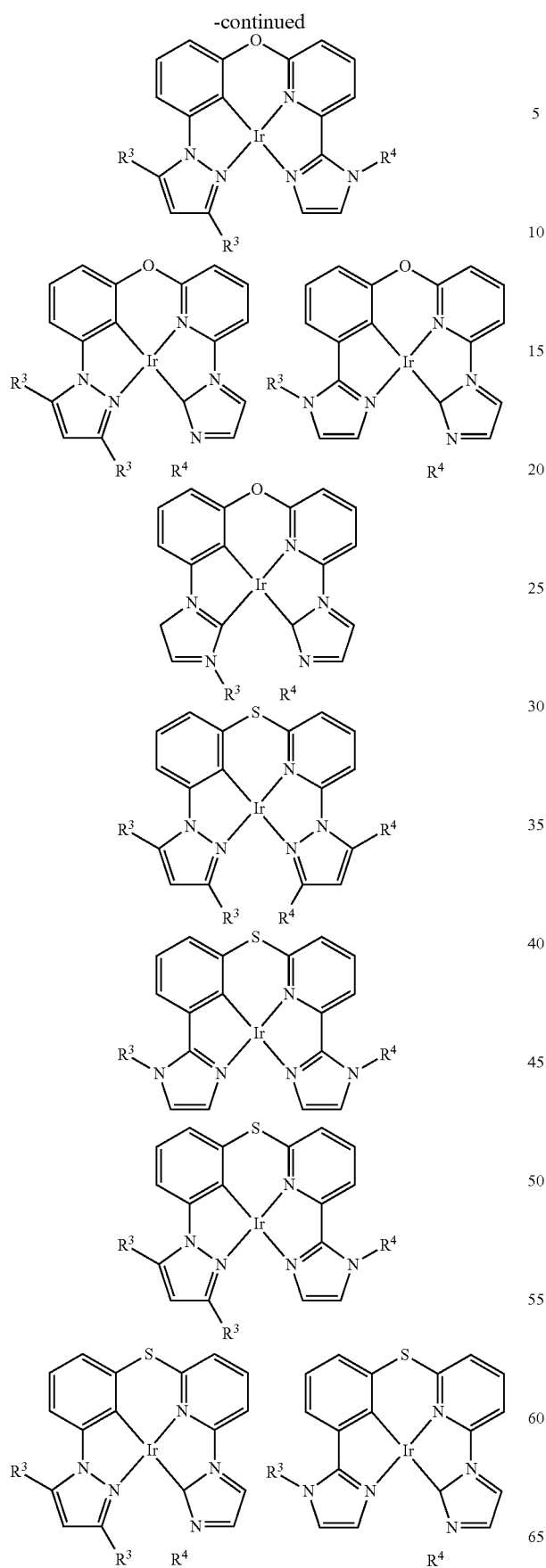
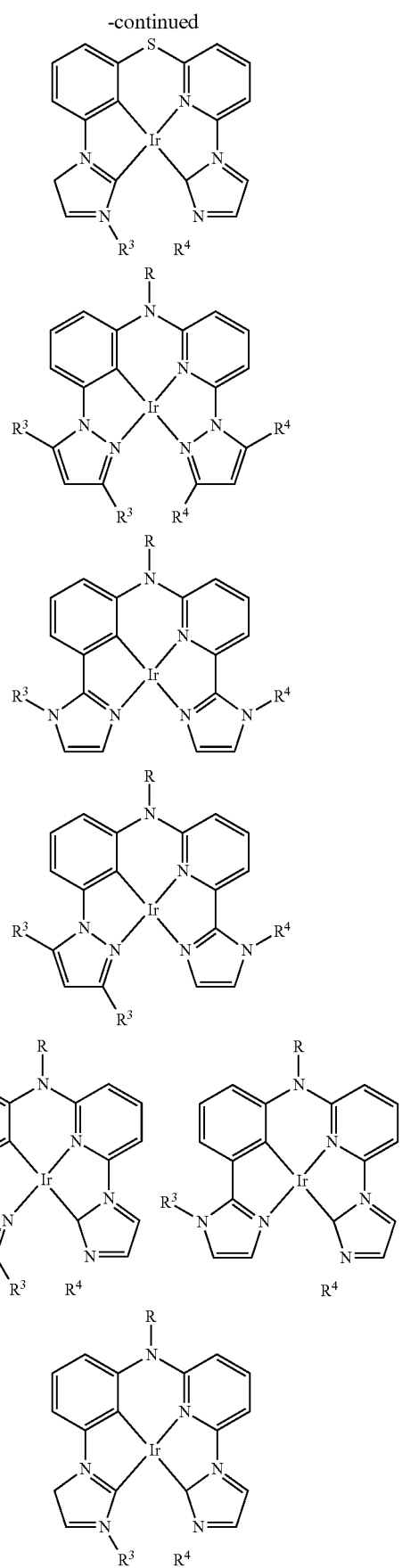

-continued
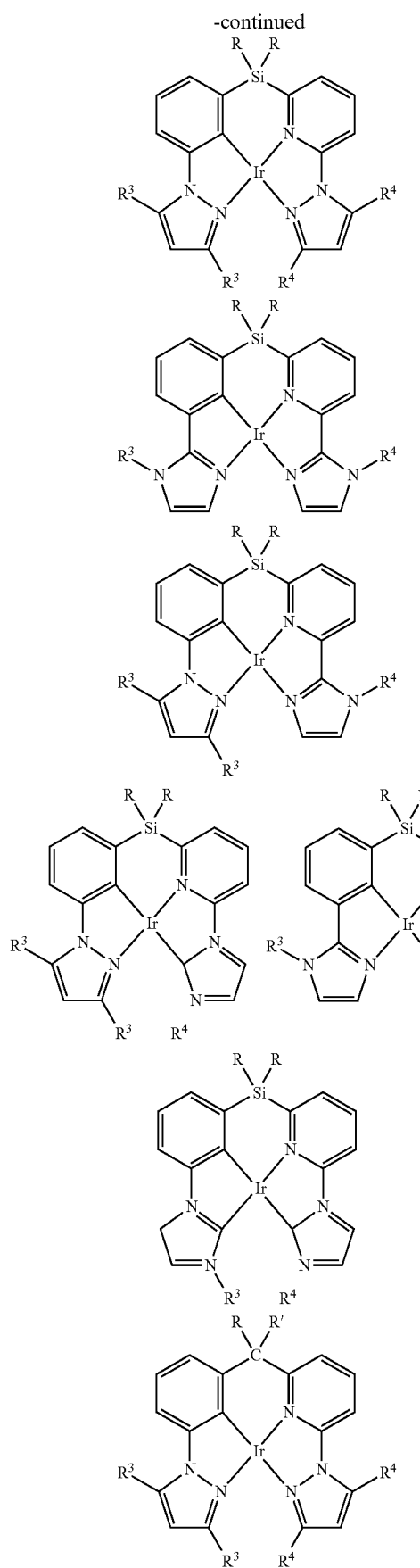
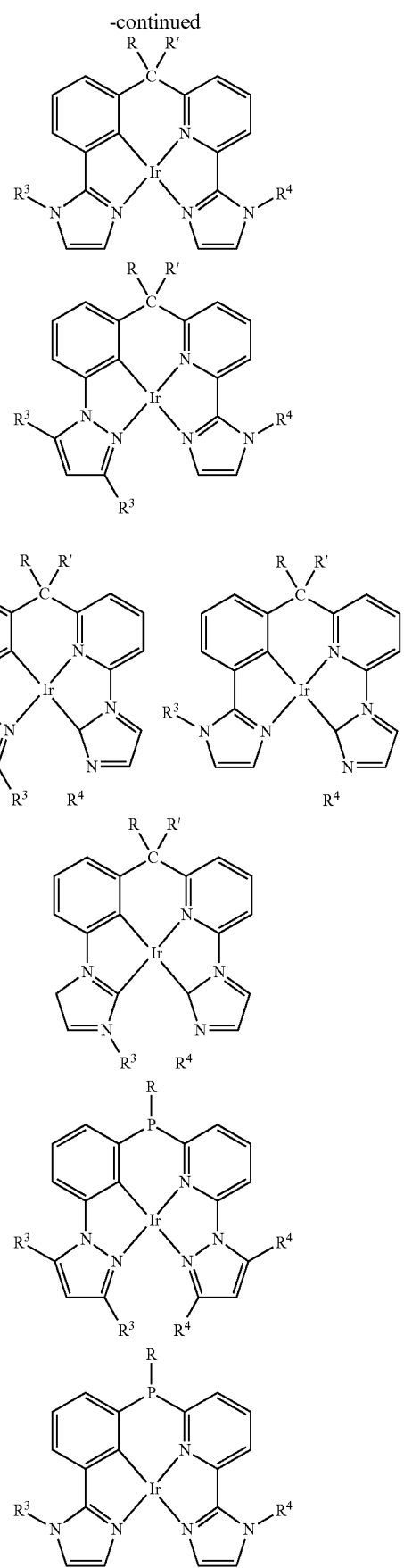

-continued
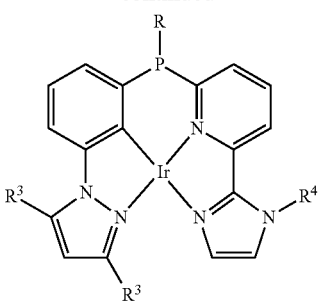
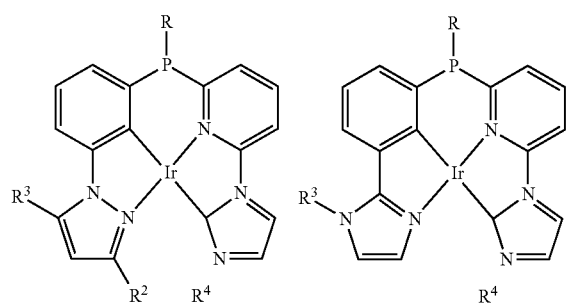
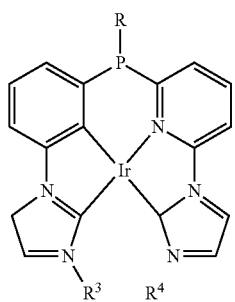
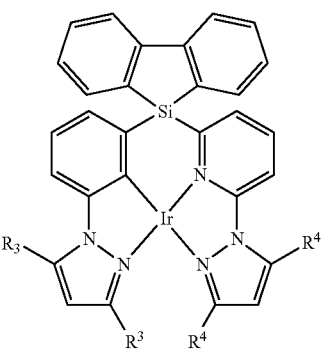
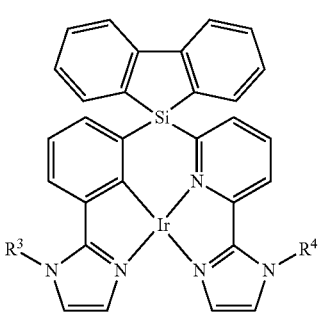
-continued
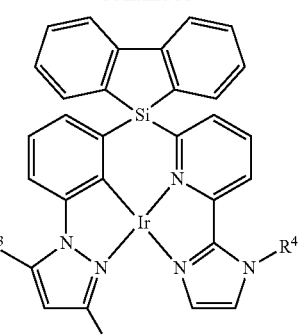
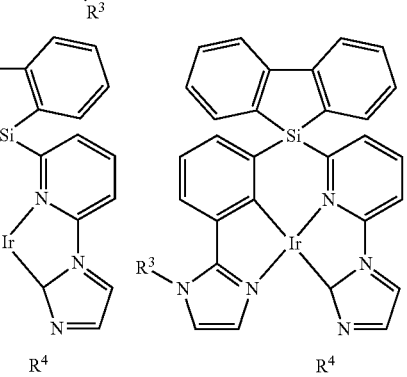
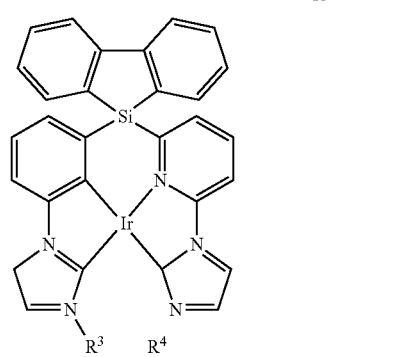
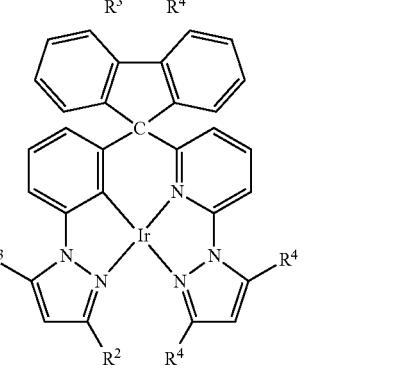
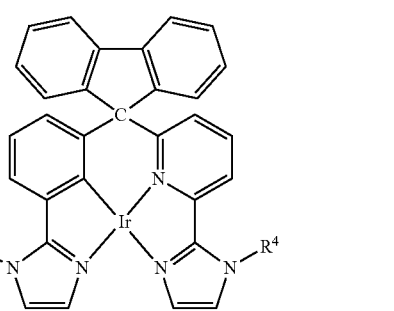

-continued
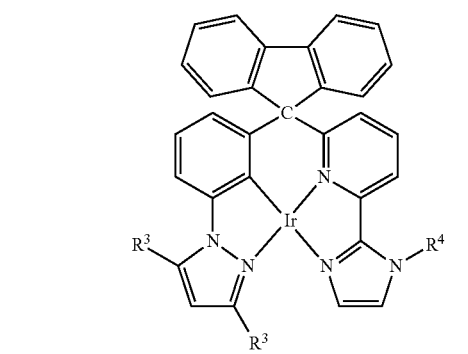
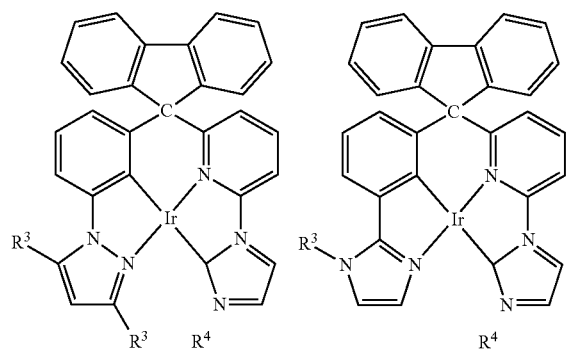
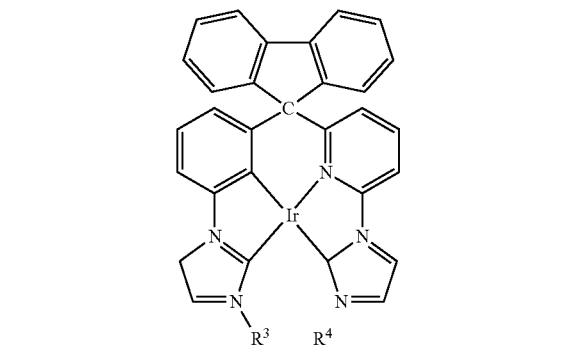
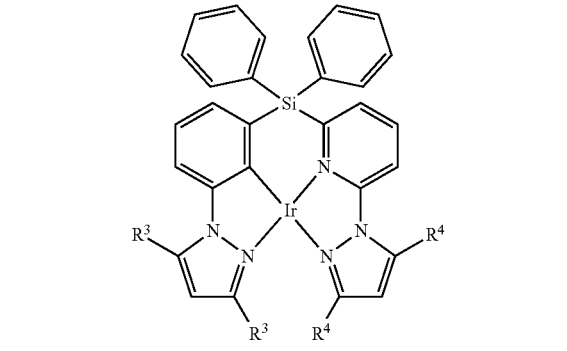
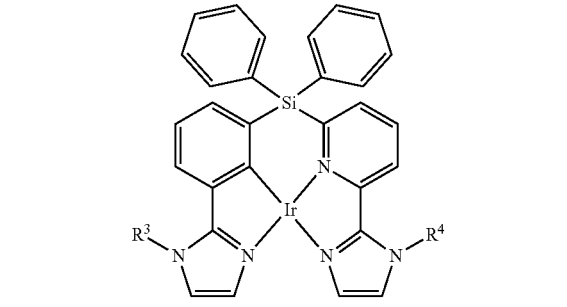
-continued
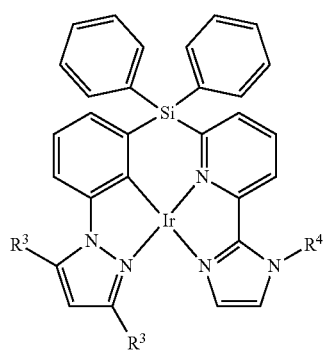
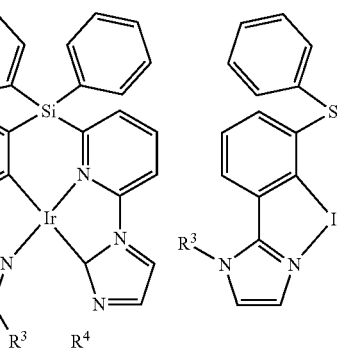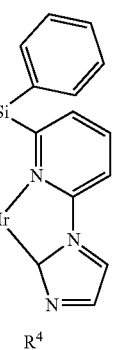
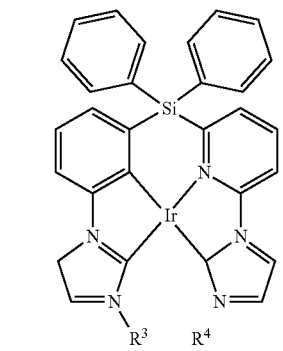
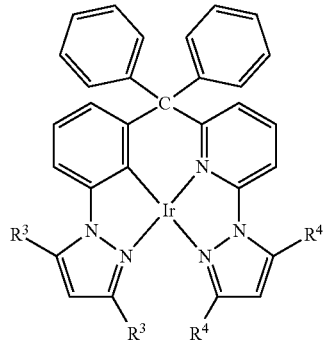
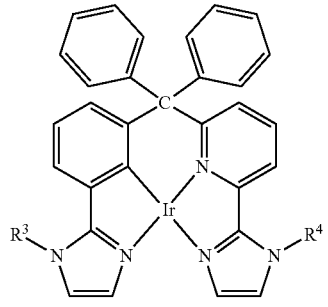

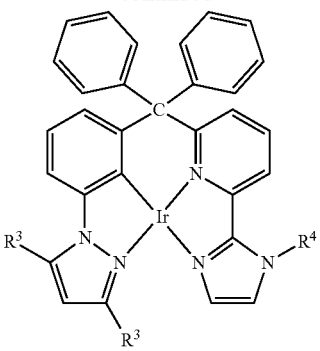
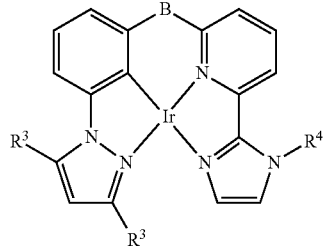
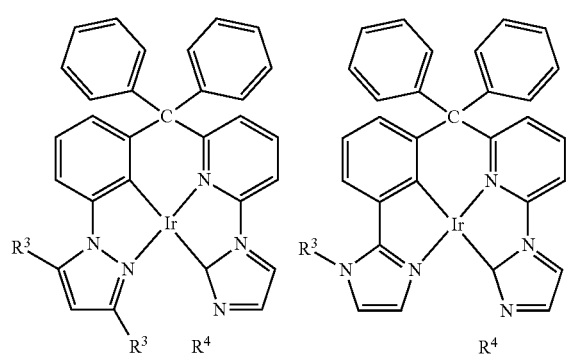
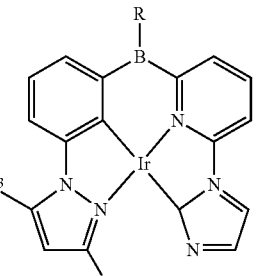
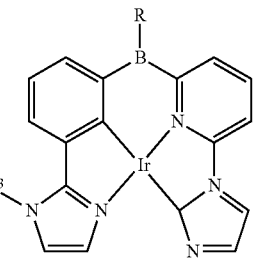
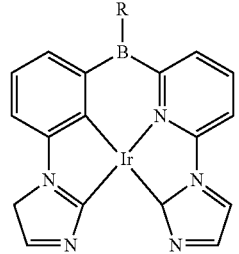
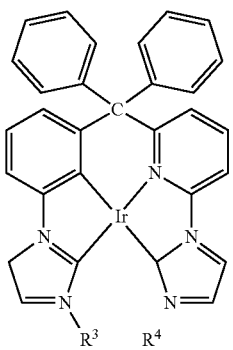
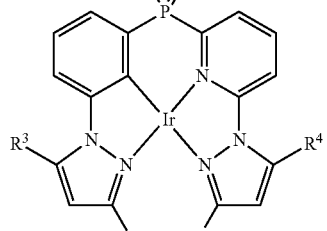
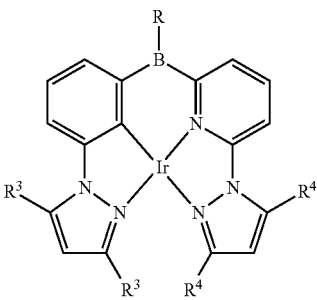
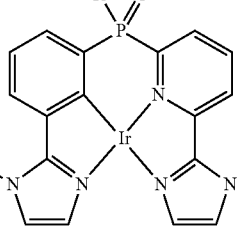
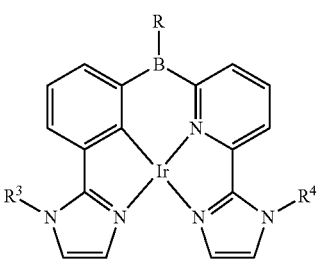
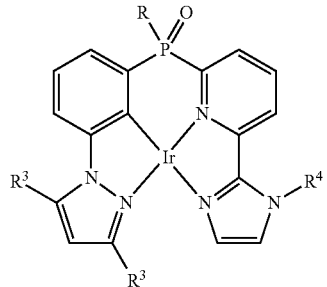

Compounds of General Formula 2 have the following structure:

$$\text{General Formula 2}$$

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y1^b$, $Y^{1c}$, $Y^{2a}$, $Y^{2b}$, $Y^{2c}$, $Y^{3a}$, $Y^{3b}$, $Y^{4a}$, $Y^{4b}$ is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, substituted or unsubstituted aryl.

A compound of General Formula 2 may have one of the following structures:

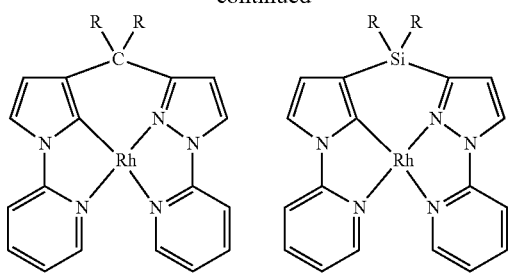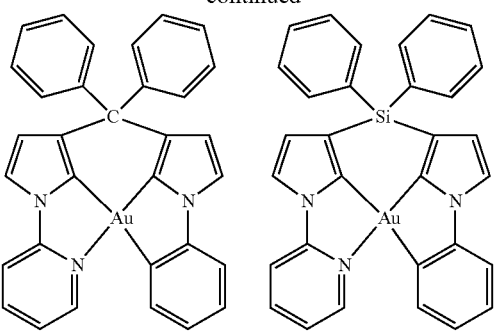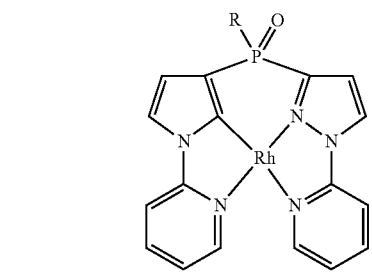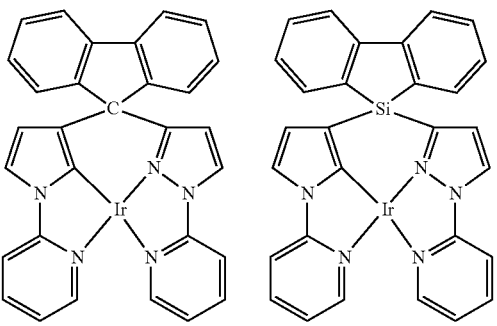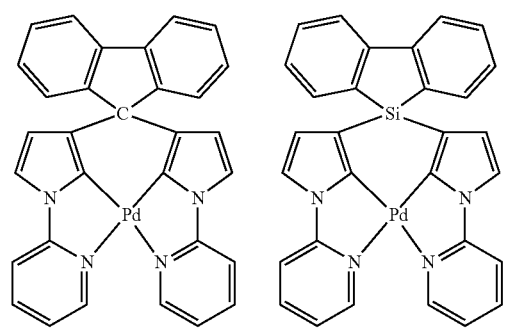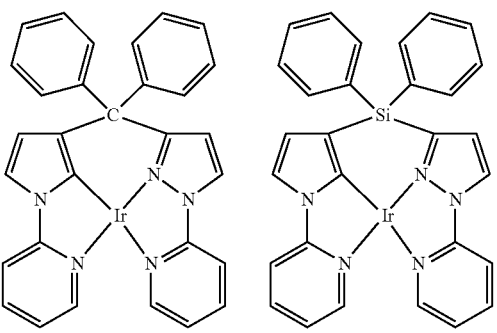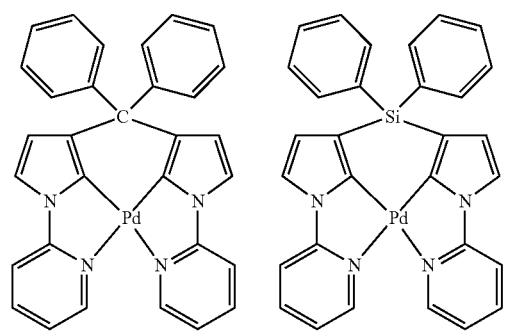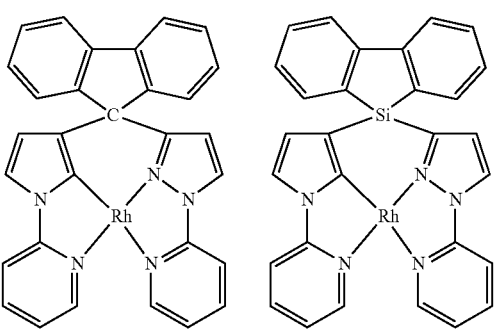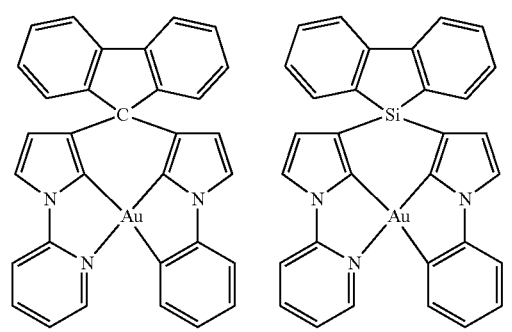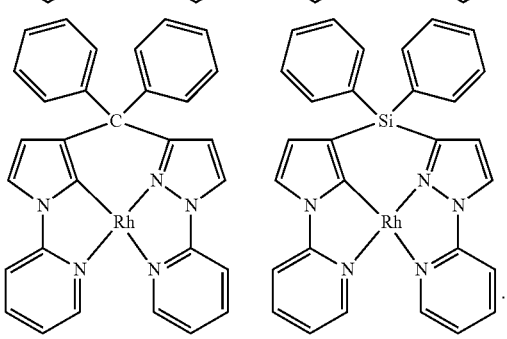
Compounds of General Formula 3 have the following structure:

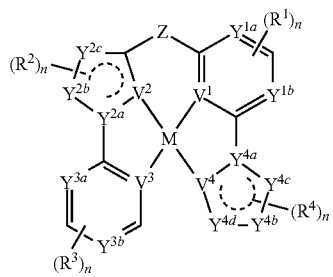

General Formula 3 wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{2c}$, $Y^{3a}$, $Y^{3b}$, $Y^{4a}$, $Y^{4b}$, $Y^{4c}$, and $Y^{4d}$ is independently N, $NR^{4a}$, or $CR^{4b}$, wherein each $R^{4a}$ and $R^{4b}$ is independently hydrogen, hydroxyl, amino, nitro, thiol, or substituted or unsubstituted $C_1$-$C_4$ alkyl, alkoxy, or aryl, hydroxyl, amino, nitro, or thiol.

A compound of General Formula 3 may have one of the following structures:

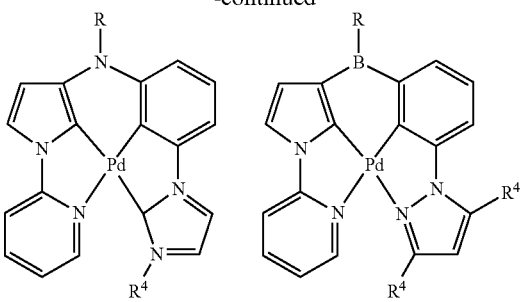

-continued

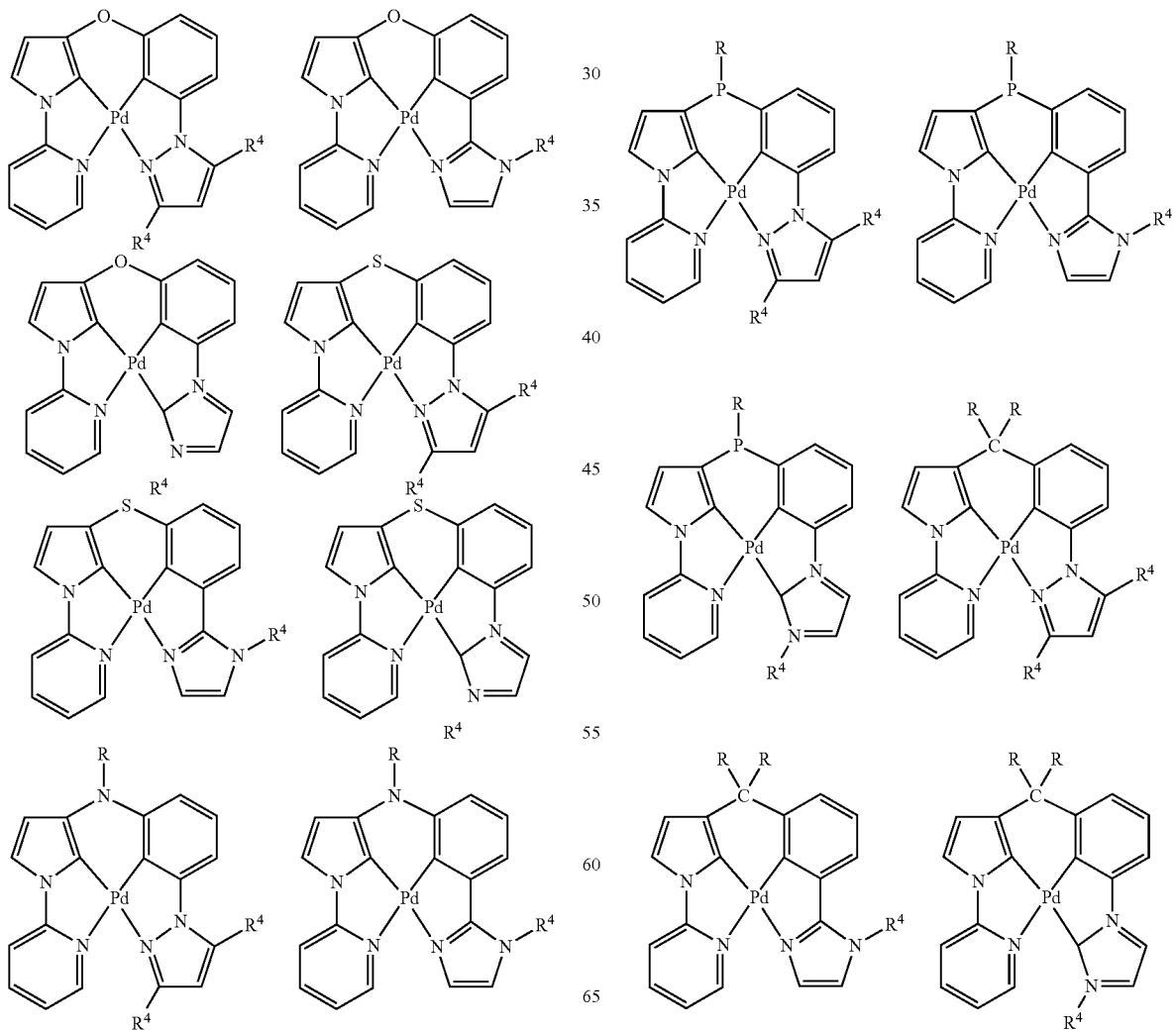

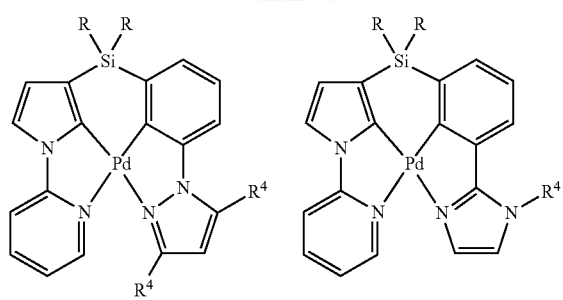
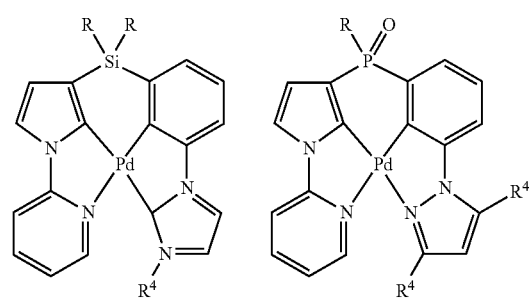
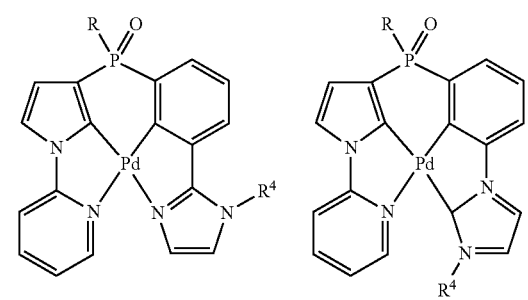
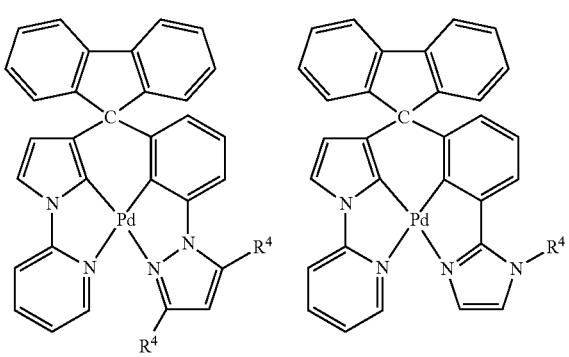
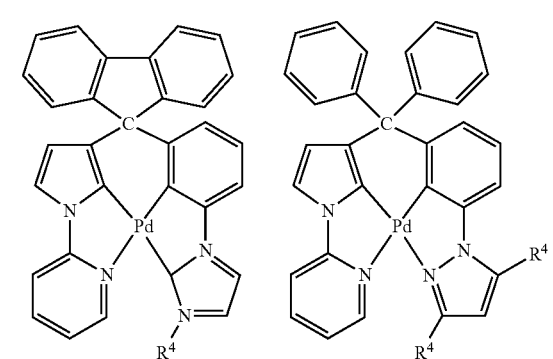
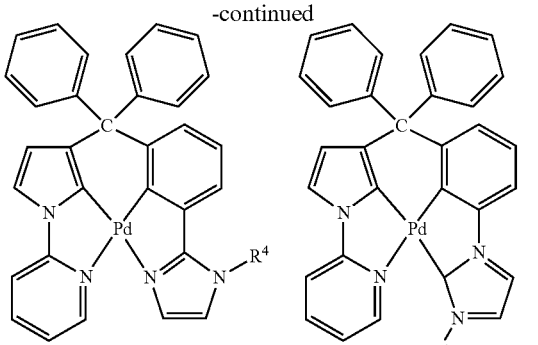
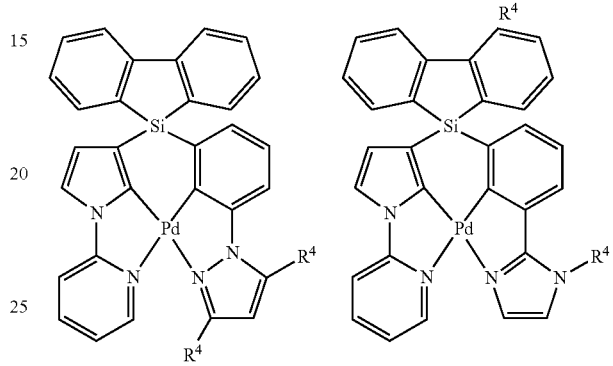
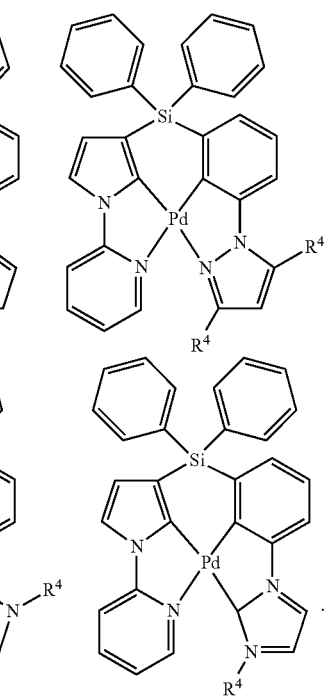
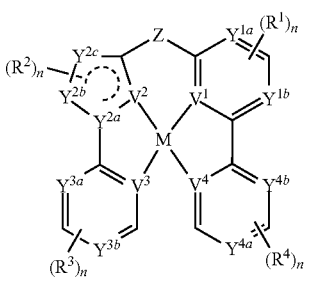
Compounds of General Formula 4 have the following structure:
General Formula 4 wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{2c}$, $Y^{3a}$, $Y^{3b}$, $Y^{4a}$, $Y^{4b}$, is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, or aryl.

A compound of General Formula 4 may have one of the following structures:

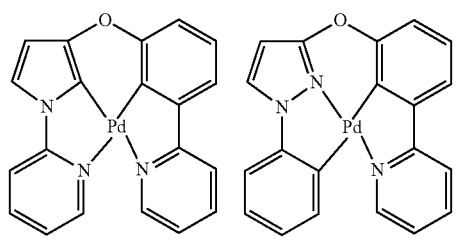
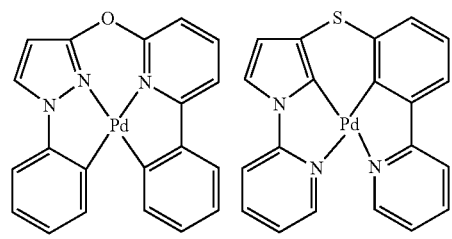
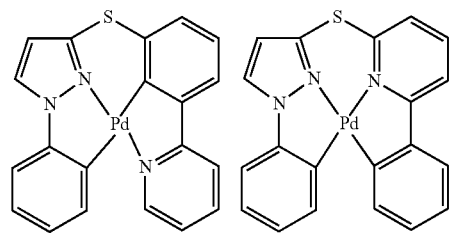
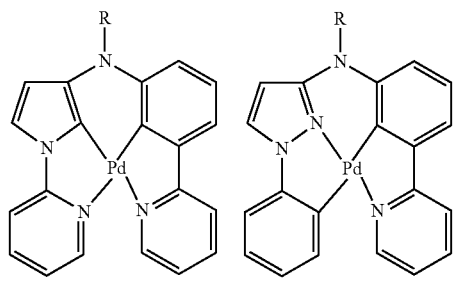
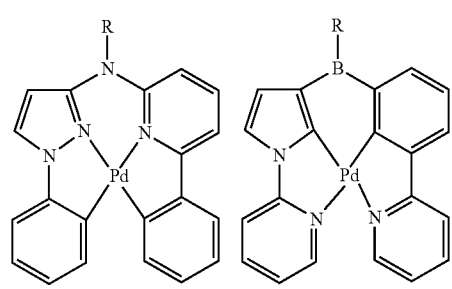
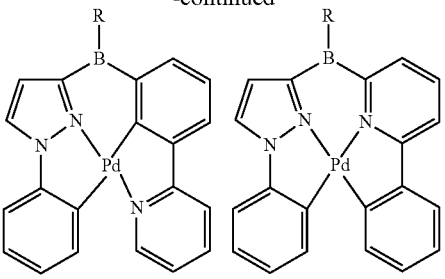
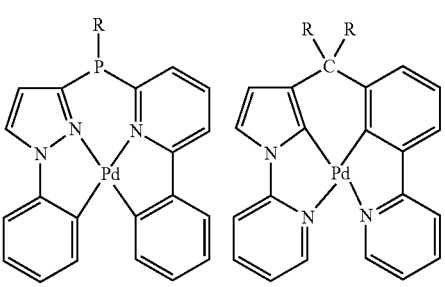
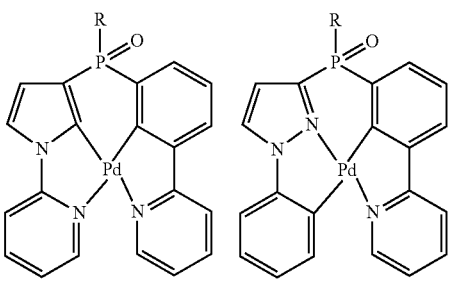
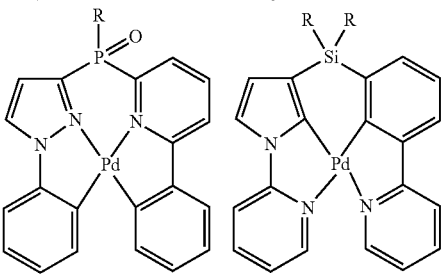

75
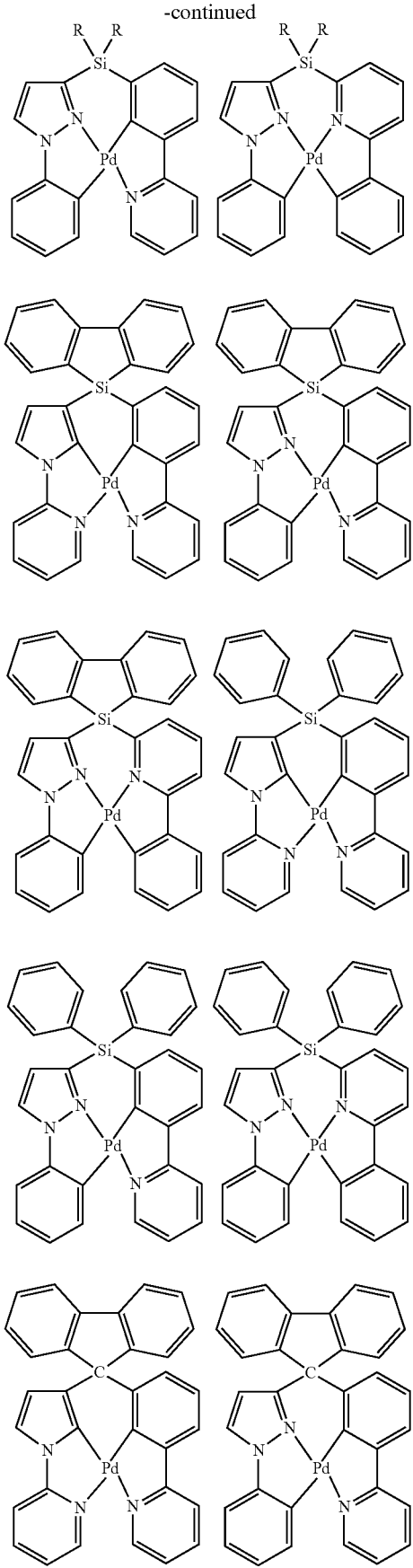
76
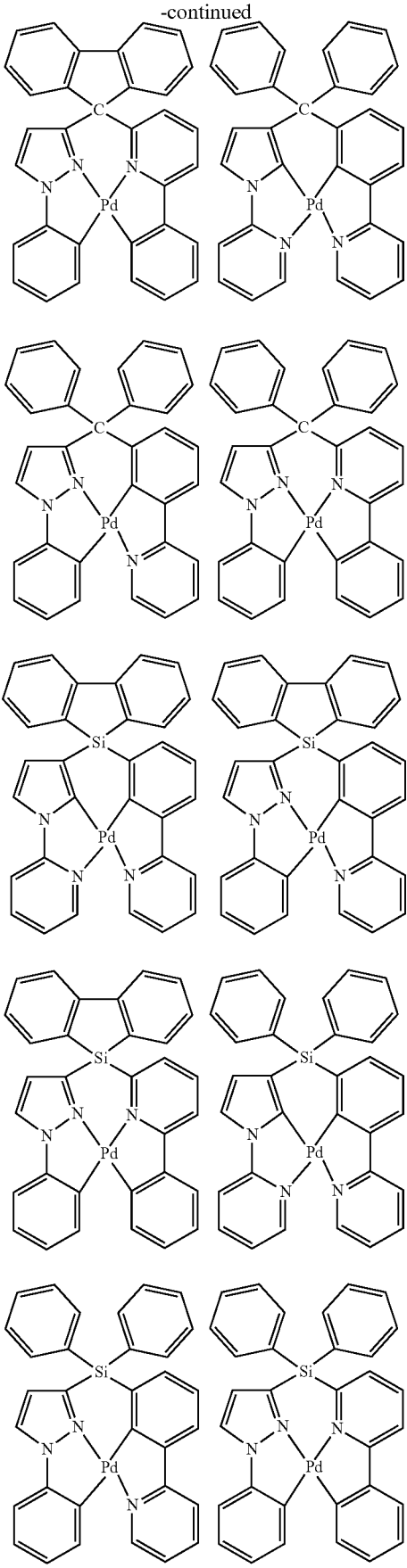

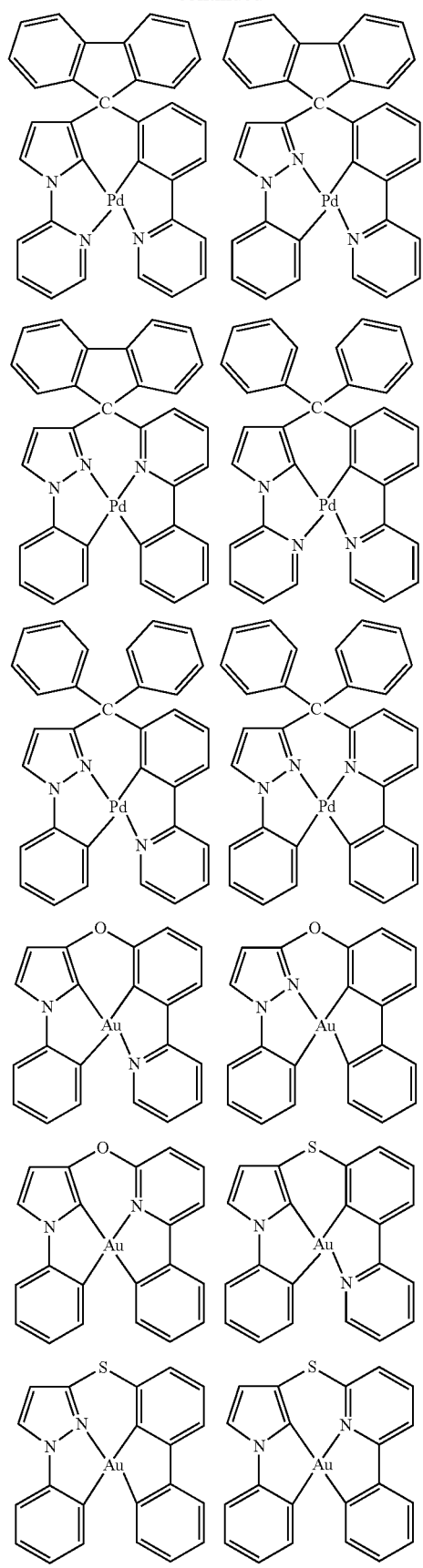
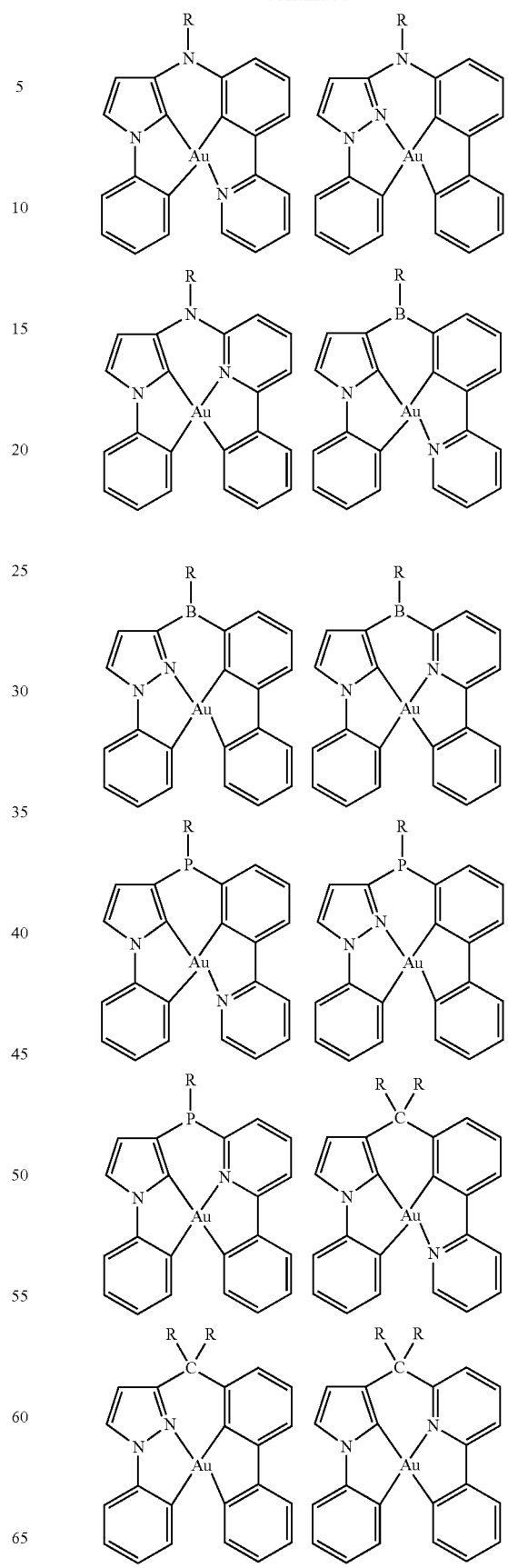

-continued
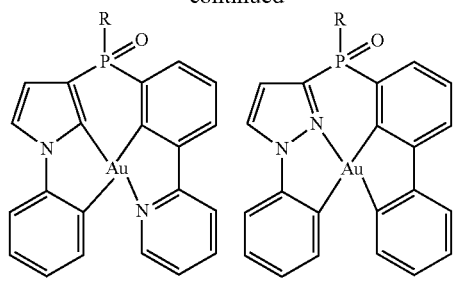
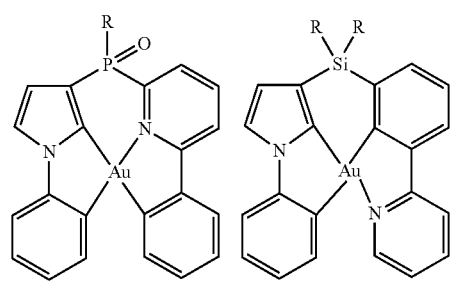
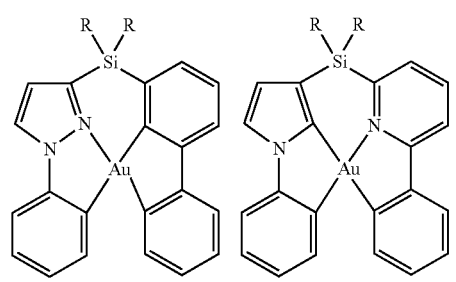
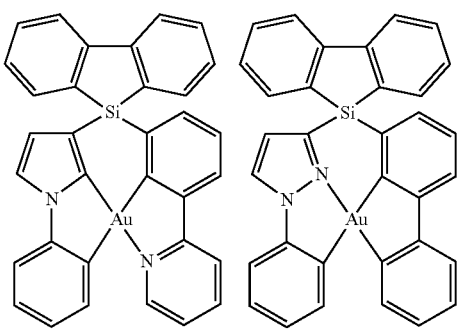
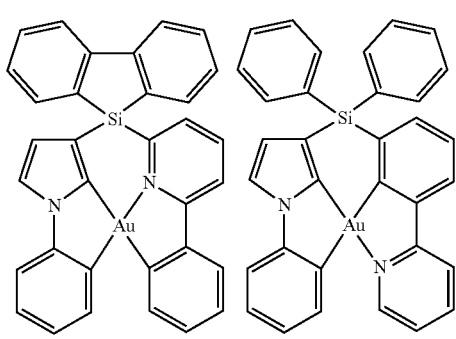
-continued
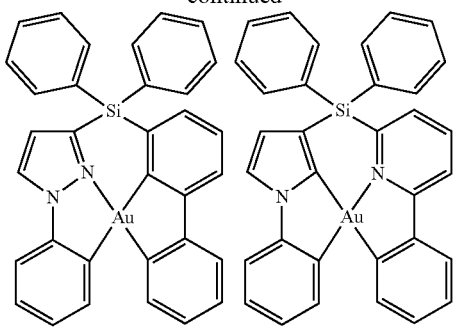
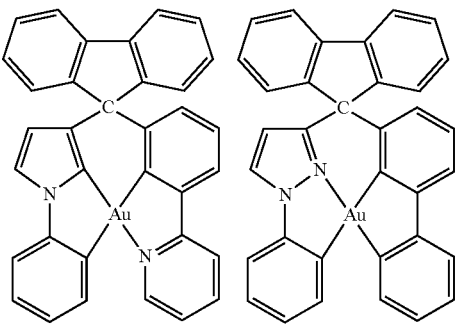
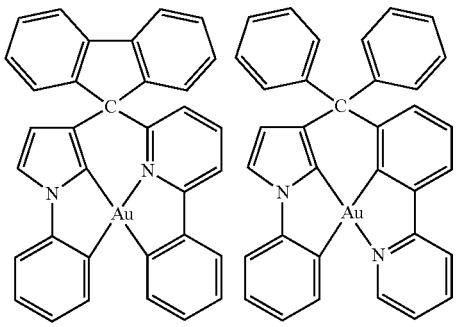
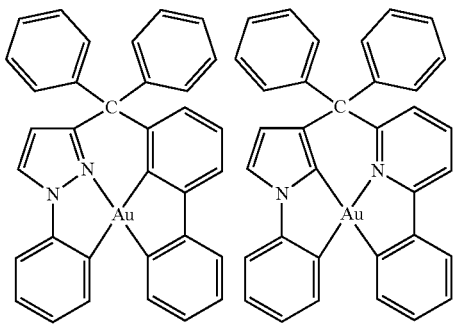
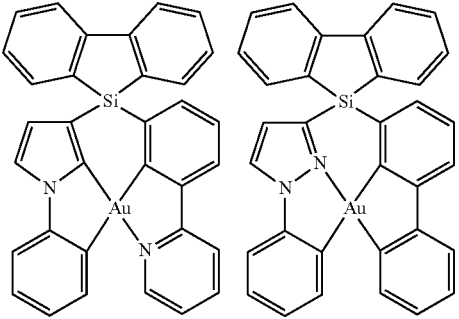

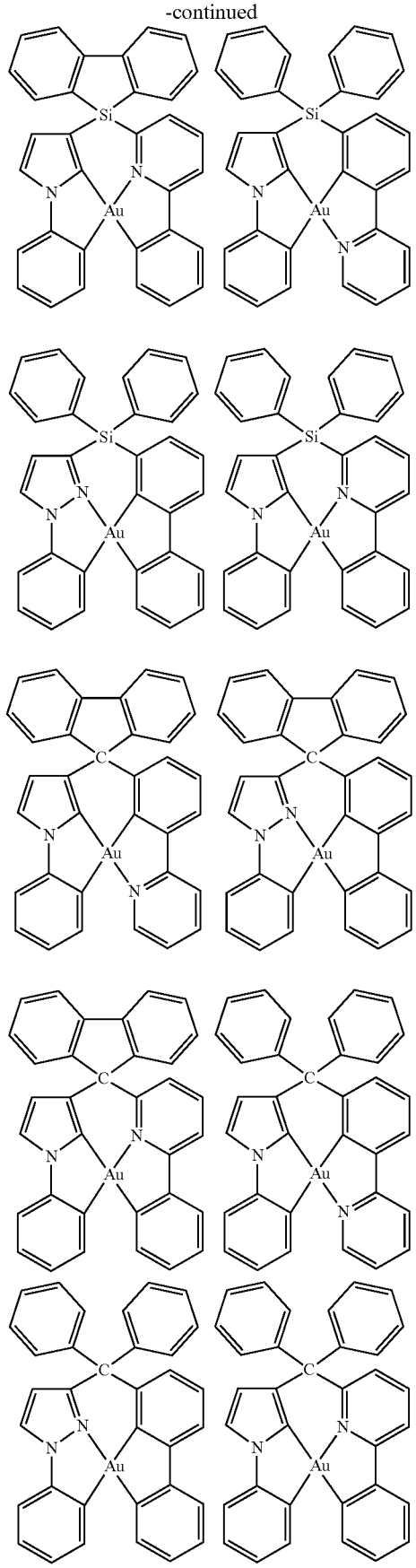
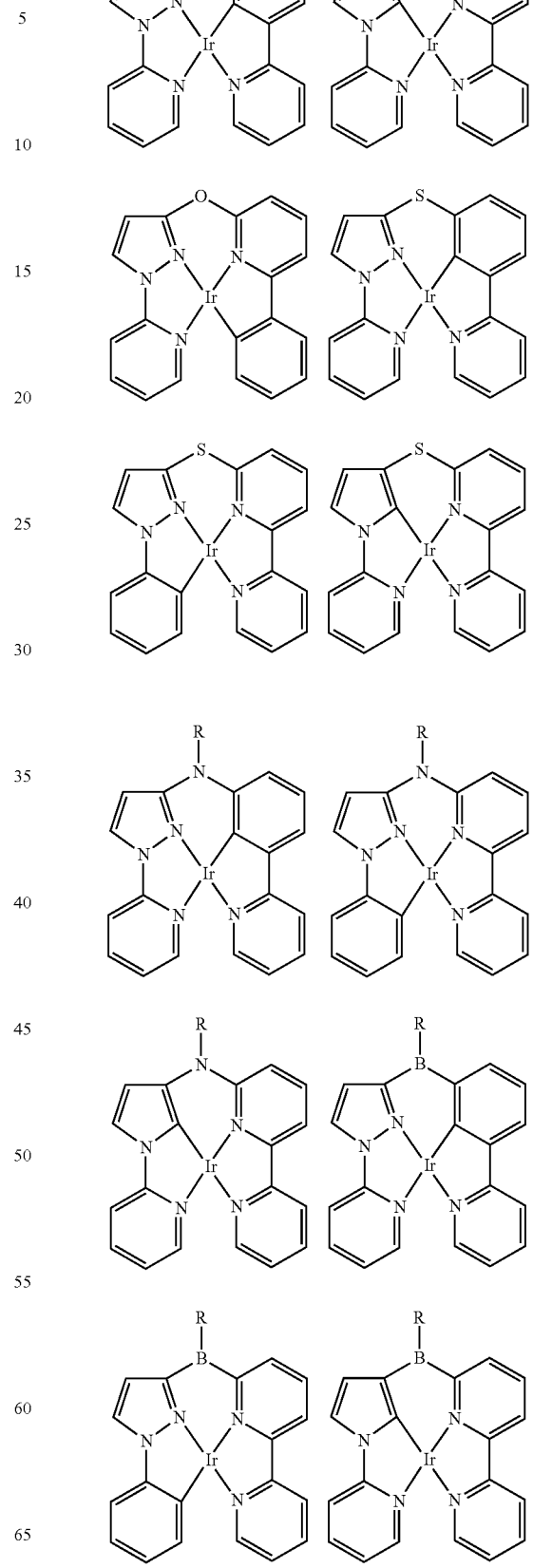

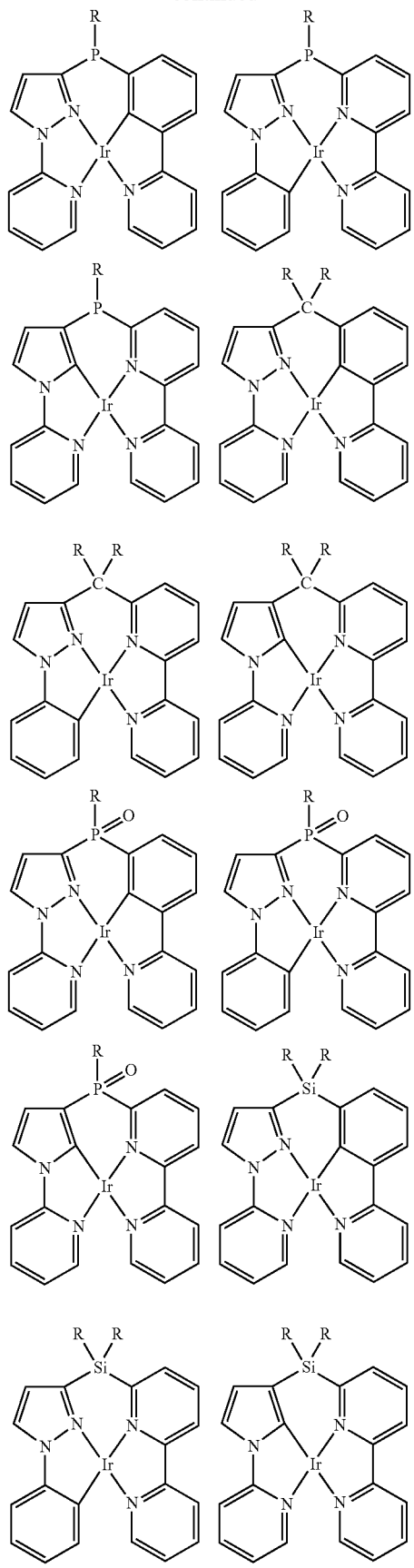

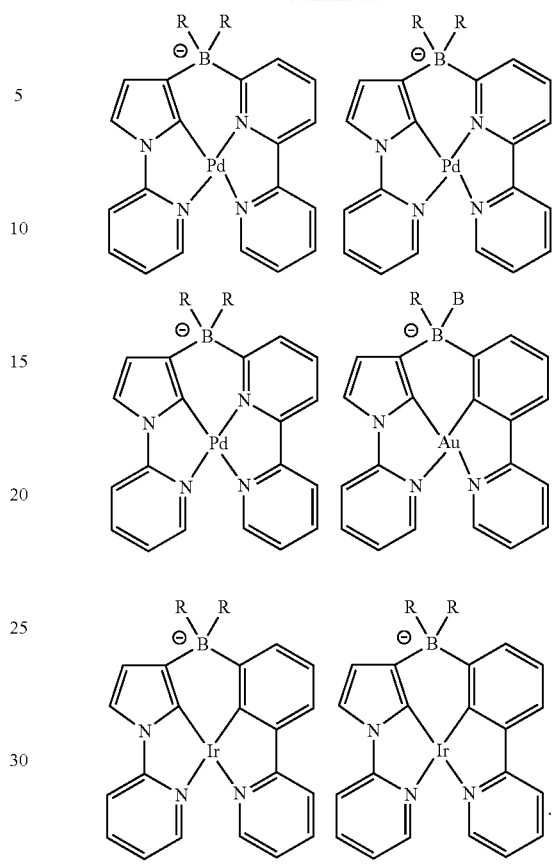

Compounds of General Formula 5 have the following structure:

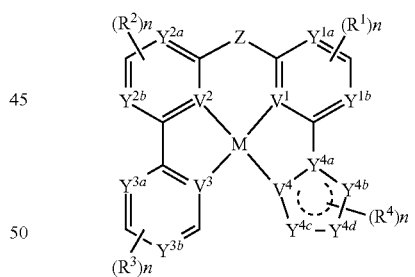

General Formula 5 wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{3a}$, $Y^{4a}$, $Y^{4b}$, $Y^{4c}$, and $Y^{4d}$ is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, or aryl.

A compound of General Formula 5 may have one of the following structures:

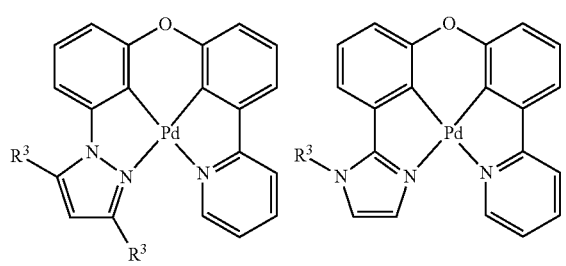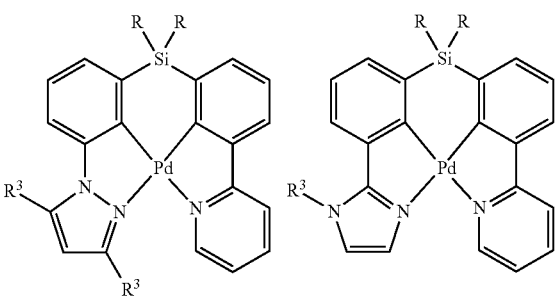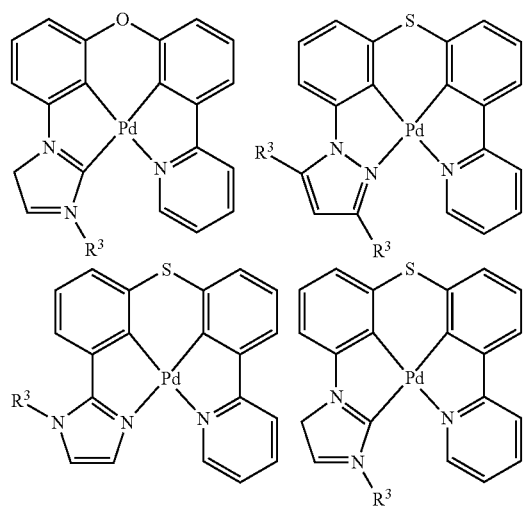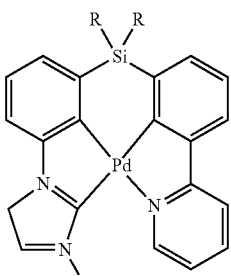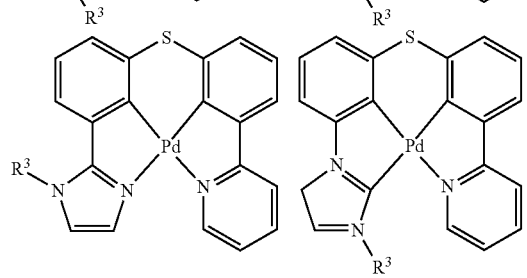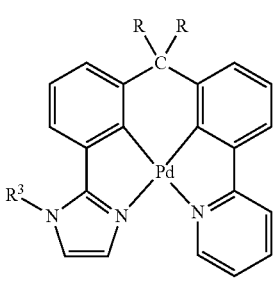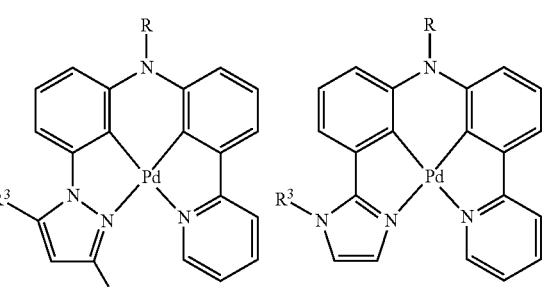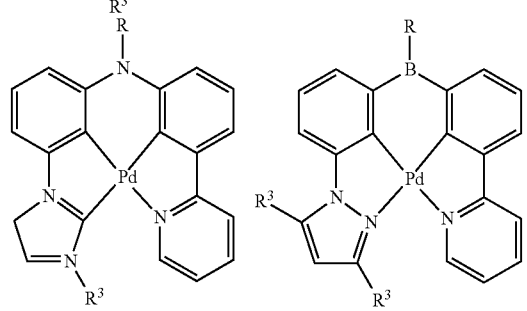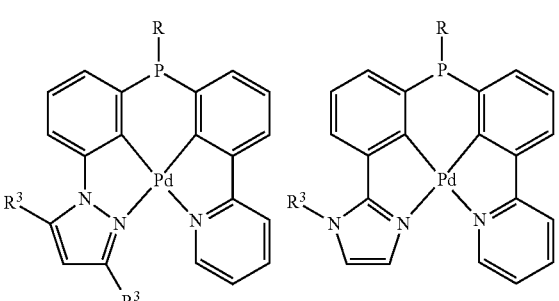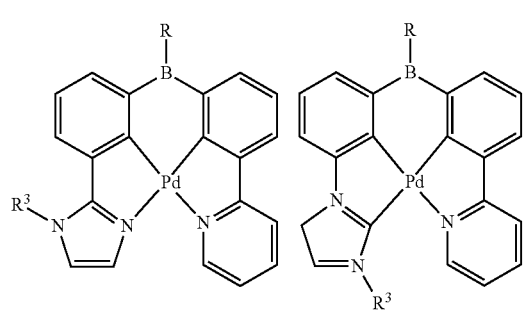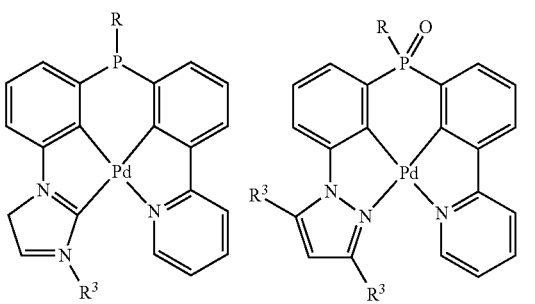

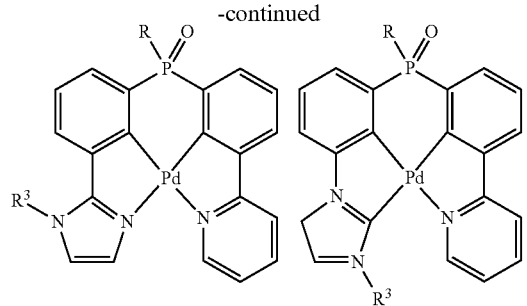
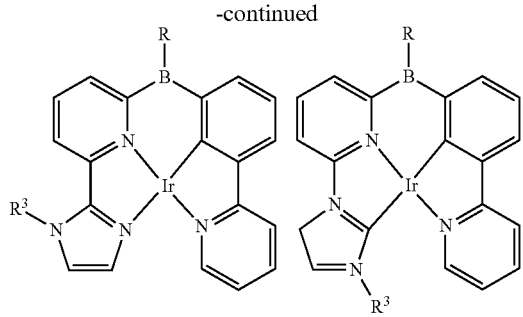
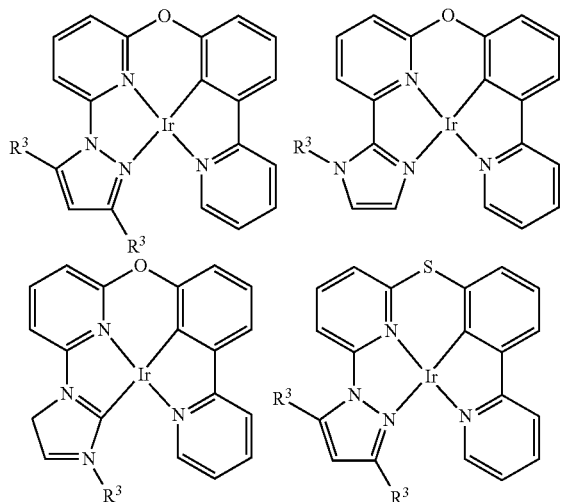
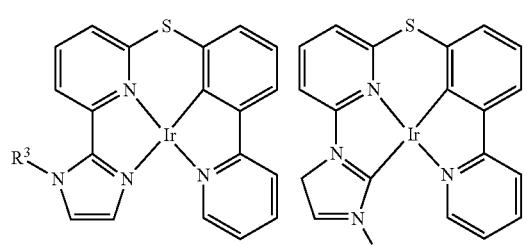
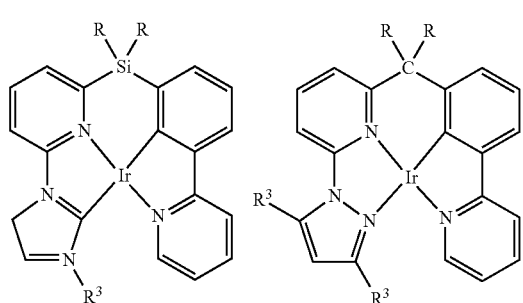
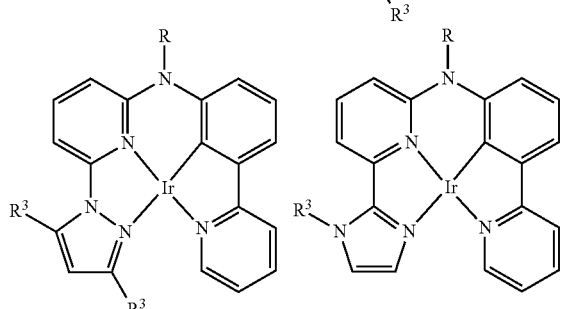
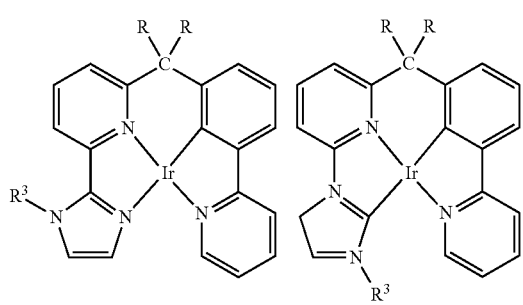
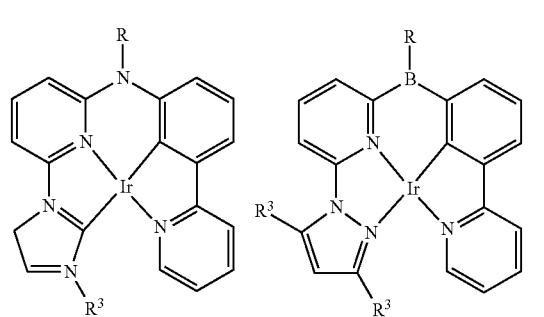
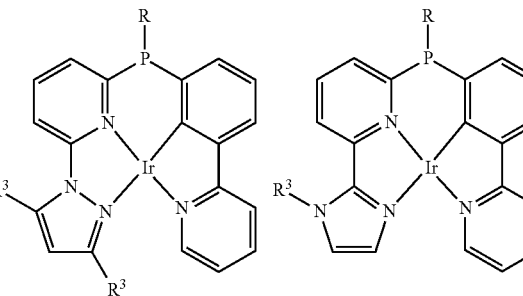

-continued
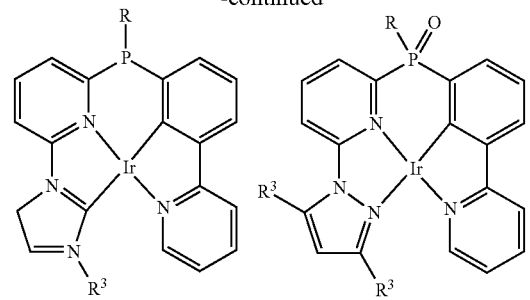
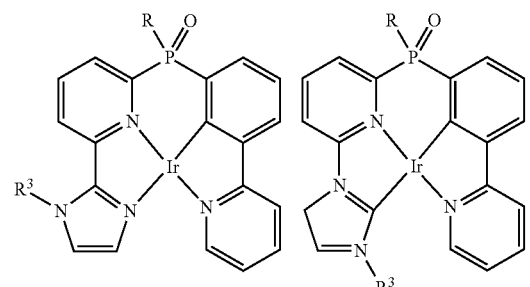
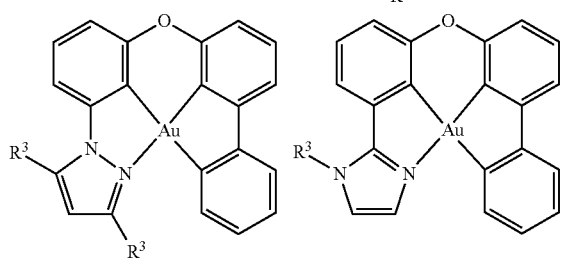
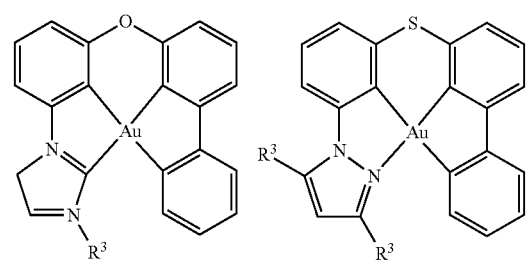
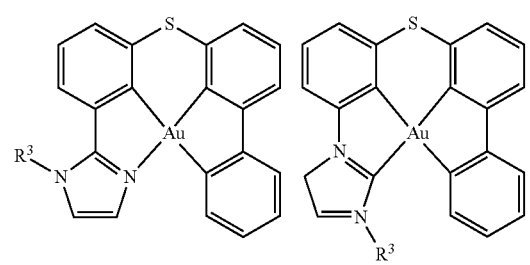
-continued
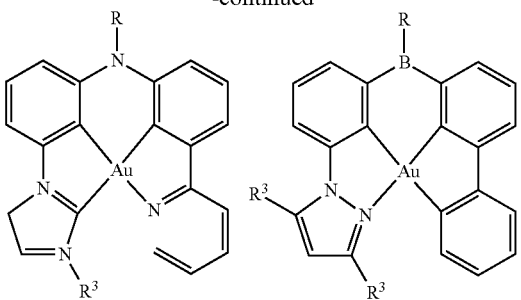
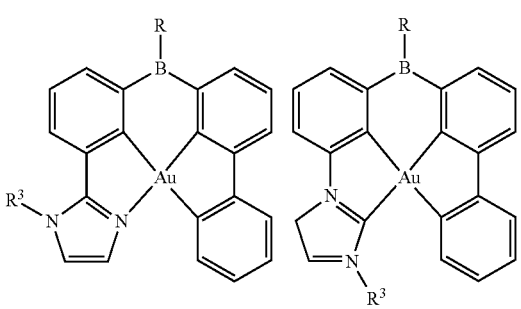
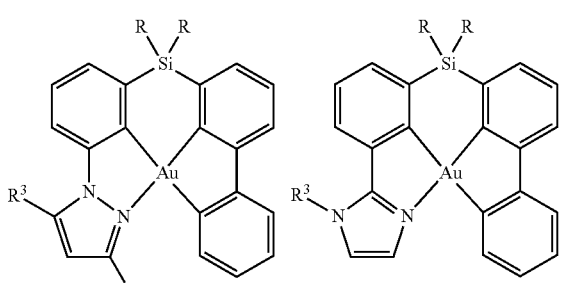
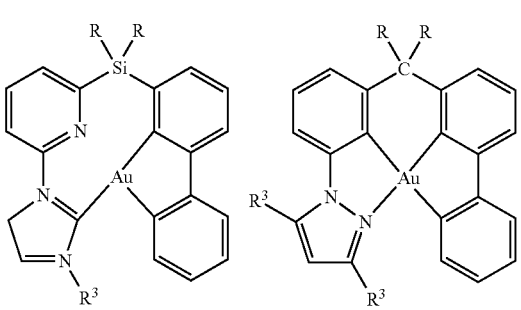
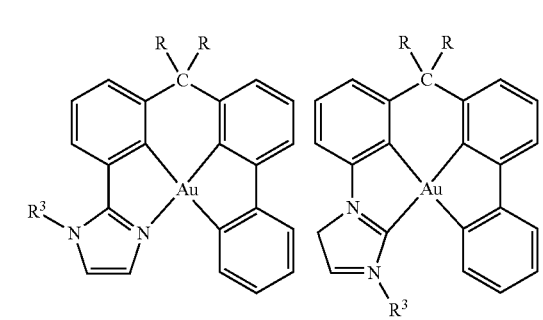

-continued
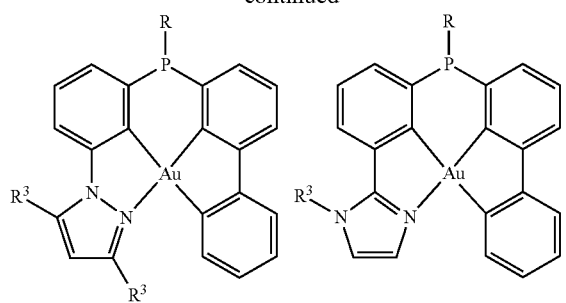
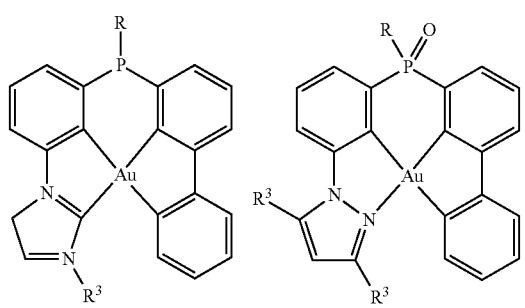
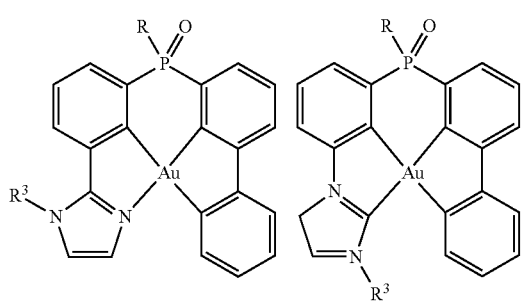
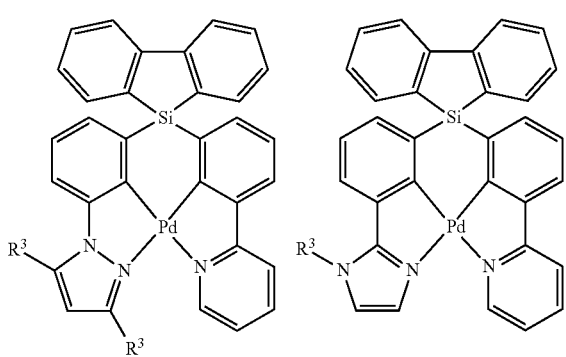
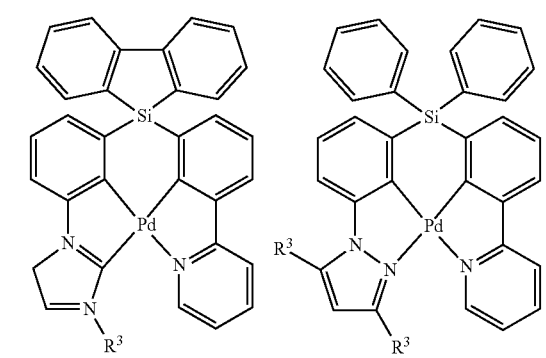
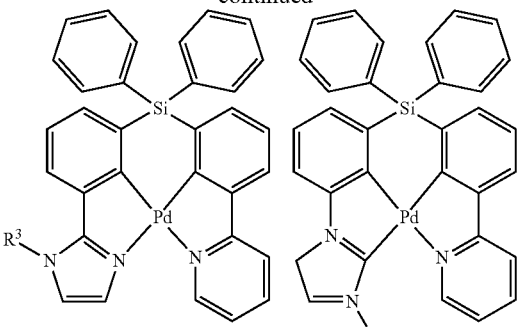
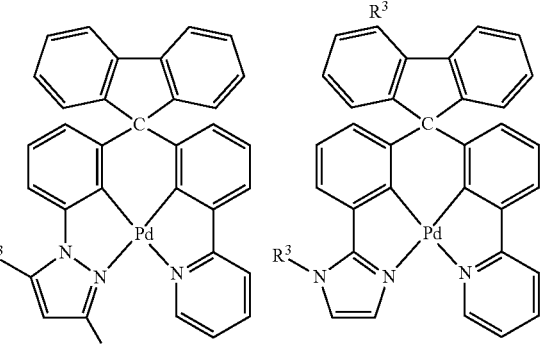
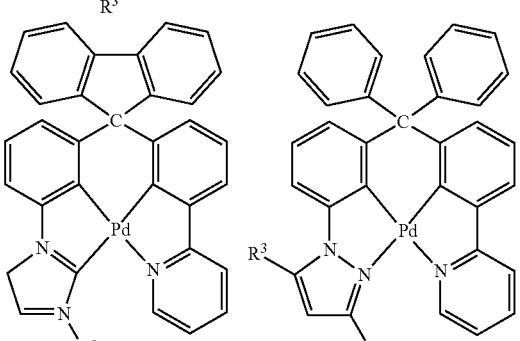
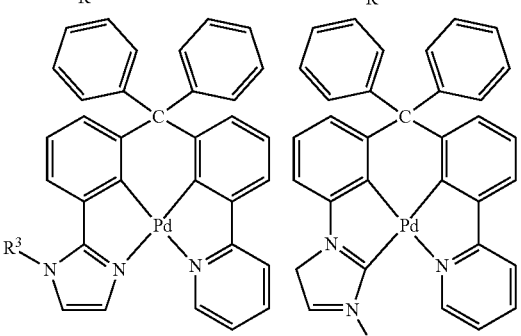
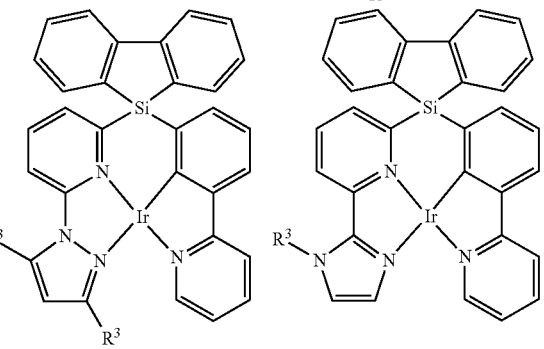

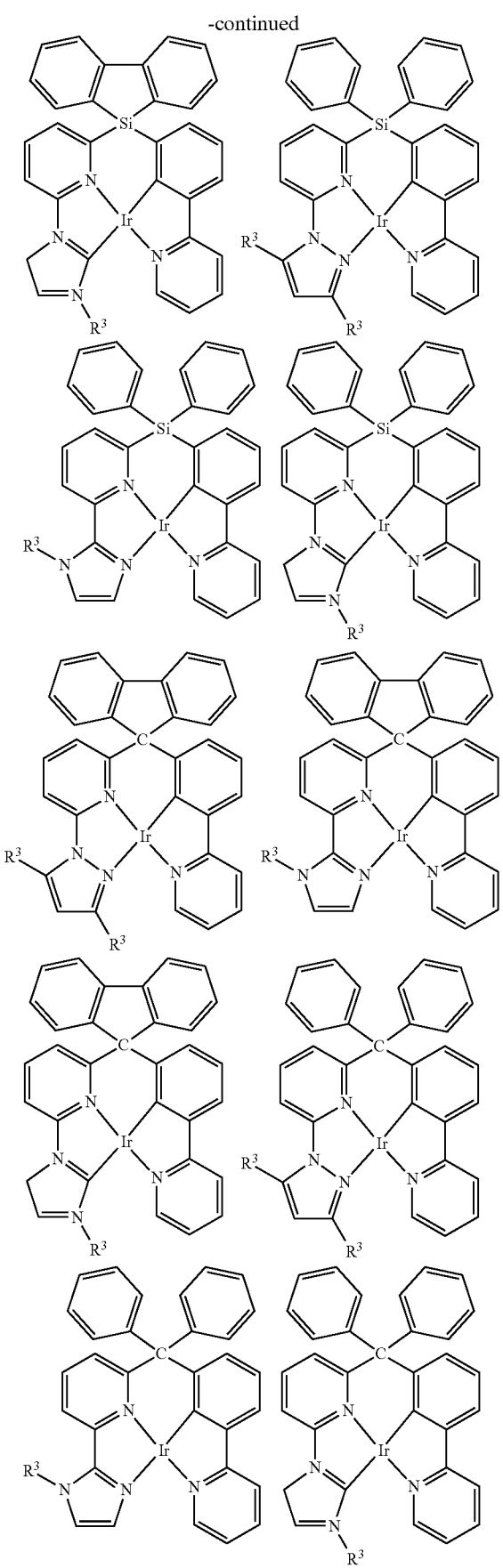
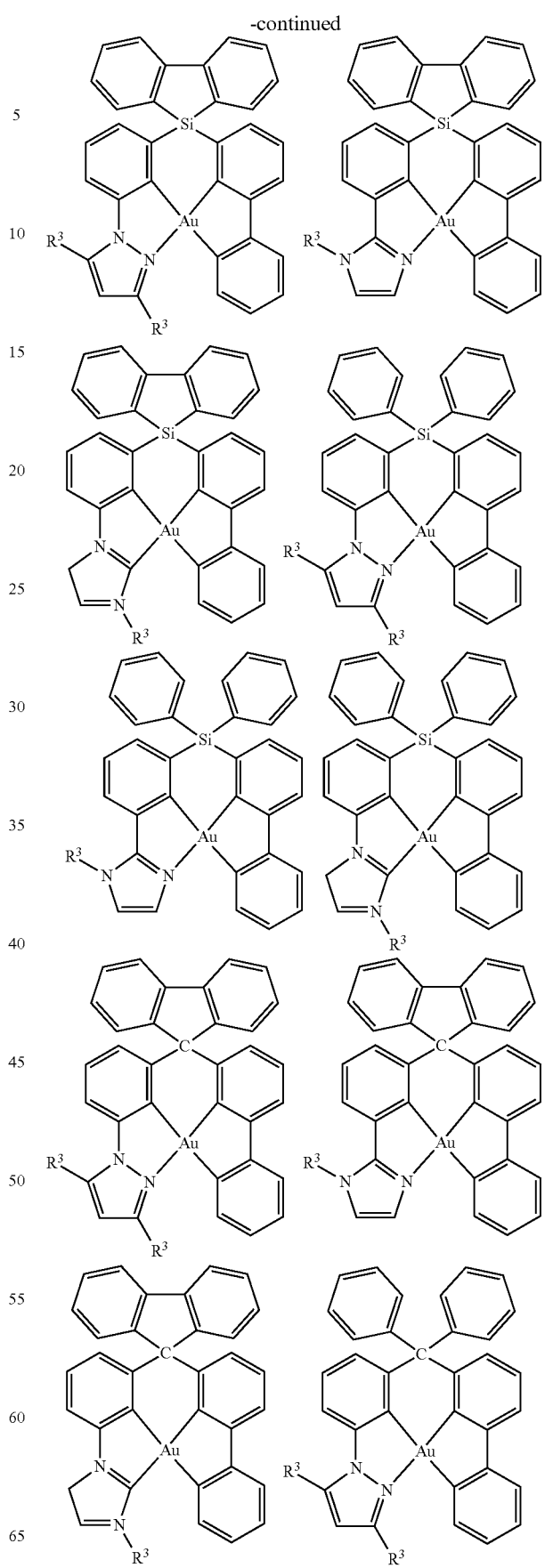

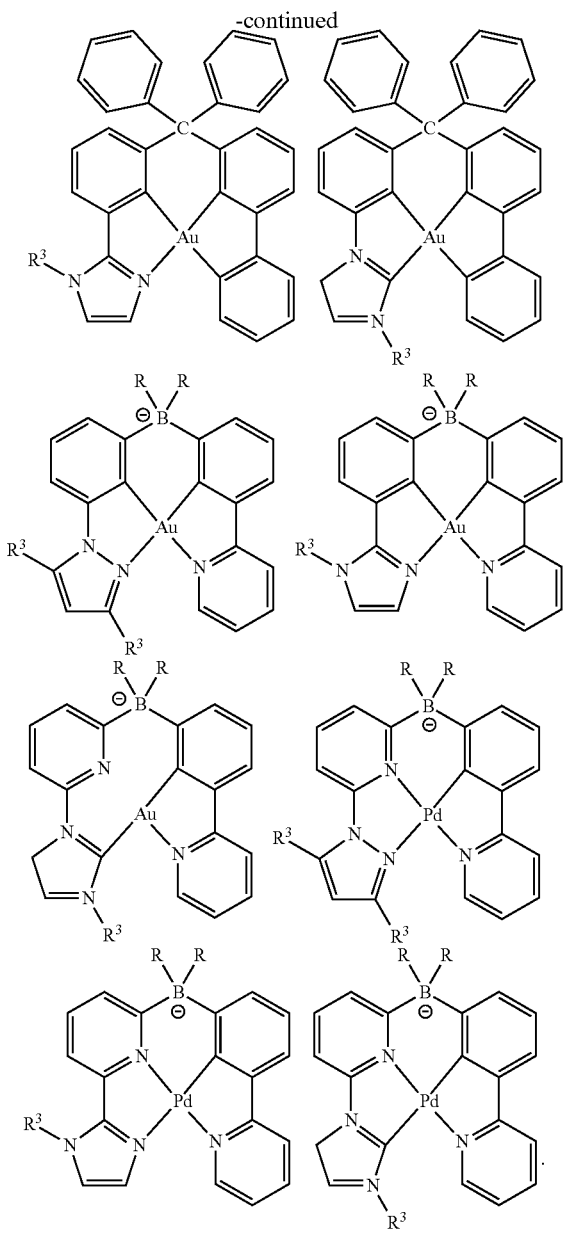

Compositions

As briefly described above, the present disclosure is directed to metal compounds. Also disclosed are compositions comprising one or more of the disclosed compounds.

Devices

As briefly described above, the present disclosure is directed to metal compounds. In one aspect, the compounds or compositions disclosed here can be used as emitters for OLED applications, such as solid state lighting.

The disclosed compounds of the present disclosure can be useful in a wide variety of applications, such as, for example, lighting devices. In a particular aspect, one or more of the compounds can be useful as host materials for an organic light emitting display device.

The disclosed compounds are useful in a variety of applications. As light emitting materials, the compounds can be useful in organic light emitting diodes (OLED)s, luminescent devices and displays, and other light emitting devices.

The energy profile of the compounds can be tuned by varying the structure of the ligand surrounding the metal center. For example, compounds having a ligand with electron withdrawing substituents will generally exhibit different properties, than compounds having a ligand with electron donating substituents. Generally, a chemical structural change affects the electronic structure of the compound, which thereby affects the electrical transport and transfer functions of the material. Thus, the compounds of the present invention can be tailored or tuned to a specific application that desires an energy or transport characteristic.

In another aspect, disclosed compound can provide improved efficiency and/or operational lifetimes in lighting devices, such as, for example, organic light emitting devices, as compared to conventional materials.

In other various aspects, the disclosed compounds can be useful as, for example, host materials for organic light emitting diodes, lighting applications, and combinations thereof.

The disclosed compounds can be made using a variety of methods, including, but not limited to those recited in the examples provided herein. In other aspects, one of skill in the art, in possession of this disclosure, could readily determine an appropriate method for the preparation of an iridium compound as recited herein.

Compounds described herein can be used in an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds and/or the host material. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A tetradentate Pd(II) complex, Pd3O3, which exhibits highly efficient excimer emission was synthesized and characterized as described below. Pd3O3 can achieve blue emission despite using phenyl-pyridine emissive ligands which have been a mainstay of stable green and red emitter designs, making Pd3O3 a good candidate for stable blue or white OLEDs. Pd3O3 utilizes a rigid and planar molecular design to achieve efficient blue and white emission while remaining aligned with stable molecular designs. Pd3O3 exhibits strong and efficient phosphorescent excimer emission expanding the excimer based white OLEDs beyond the sole class of Pt complexes. Devices of Pd3O3 demonstrate peak external quantum efficiencies as high as 24.2% and power efficiencies of 67.9 lm/W for white devices. Furthermore, Pd3O3 devices fabricated in a stable device structure achieved nearly 1000 h at 1000 cd/m$^2$ without any outcoupling enhancement while simultaneously achieving peak external quantum efficiencies of 19.9% and power efficiencies over 60 lm/W.

Synthesis

General Synthetic Procedure:

All commercial reagents were purchased and used as received without further purification. Pd(OAc)$_2$ was purchased from Pressure Chemical Co. n-Bu$_4$NBr, CuI, 2-(tributylstannyl)pyridine and 2-picolinic acid were purchased from Sigma Aldrich. Silica gel (40-60 μm) was purchased from Agela Technologies and BDH. DMSO, toluene (low water), and acetic acid were purchased from Alfa Aesar, J. T. Baker, Fluke and BDH respectively.

All reactions were carried out under an inert N$_2$ atmosphere in oven-dried glassware. External bath temperatures were used to record all reaction temperatures. Flash column chromatography was carried out with silica gel. Proton and carbon NMR spectra ($^1$H NMR and $^{13}$C NMR) were recorded in dimethyl sulfoxide-d$_6$ (DMSO-d$_6$) on a Varian 400 MHz NMR spectrometer. The solvent residual peak (DMSO-d$_6$) was calibrated to 2.50 ppm for $^1$H NMR and 39.52 ppm for $^{13}$C NMR. Multiplicities are abbreviated as follows: s=singlet, d=doublet, dd=doublet of doublets, t=triplet, br=broad, m=multiplet.

Synthesis of 2-(3-(3-(pyridin-2-yl)phenoxy)phenyl) pyridine

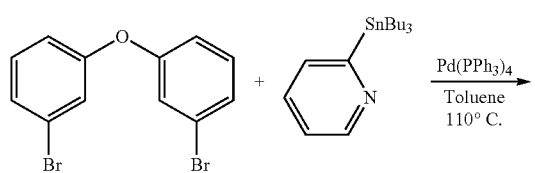

-continued

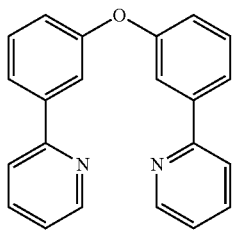

To a 100 mL three-neck round-bottom flask were added 1-bromo-3-(3-bromophenoxy)benzene (656 mg, 2 mmol) and 2-(tributylstannyl)pyridine (1.76 g, 4.8 mmol). The flask was evacuated and backfilled with nitrogen for three cycles. Tetrakis(triphenylphosphine)palladium(0) (115 mg, 0.1 mmol) and toluene (20 mL) were added under nitrogen, and the reaction mixture was stirred at 110° C. under nitrogen for 24 hours. After cooling to room temperature, the mixture was poured into 50 mL of water and extracted with ethyl acetate (3×100 mL), and the combined organic layers were dried with anhydrous Na$_2$SO$_4$ and concentrated under reduced pressure. Purification of the resulting residue by column chromatography (hexanes:ethyl acetate=5:1) afforded the desired product as a white solid (550 mg, 84%). $^1$H NMR (DMSO-d$_6$, 400 MHz): δ 7.16 (dd, J=8.0, 2.4 Hz, 2H), 7.33-7.38 (m, 2H), 7.54 (t, J=7.6 Hz, 2H), 7.79 (m, 2H), 7.85-7.91 (m, 4H), 7.98 (d, J=8 Hz, 2H), 8.63 (d, J=4.4 Hz, 2H).

Synthesis of Palladium (II) 2-(3-(3-(pyridin-2-yl) phenoxy)phenyl) pyridine

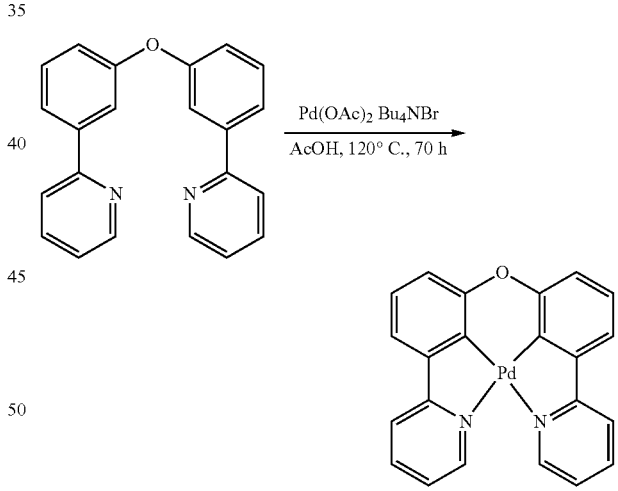

Figure 2:
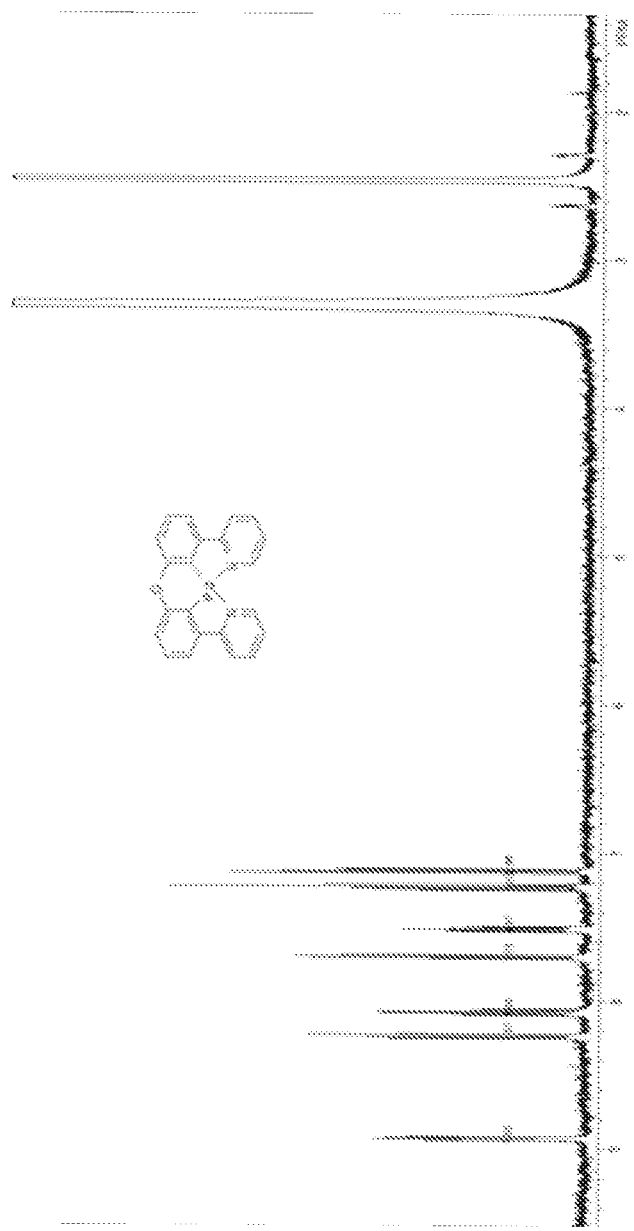
FIG. 2 shows a ¹H NMR spectrum of Pd3O3 in DMSO-d6 at 400 MHz.

2-(3-(3-(pyridin-2-yl)phenoxy)phenyl)pyridine (470 mg, 1.45 mmol), Pd(OAc)$_2$ (348 mg, 1.55 mmol), and n-Bu$_4$NBr (48 mg, 0.149 mmol) were added to a 100 mL three-neck round-bottom flask, then 30 mL acetic acid was added. The mixture was sparged with nitrogen for 30 minutes, then stirred at ambient temperature for 12 hours. The mixture was subsequently heated in an oil bath at a temperature of 110° C. for another 72 hours. 100 mL of water was added after the mixture was cooled down to room temperature. The resulting precipitate was collected through filtration, washed with water three times, then dried in air. The collected solid was purified through column chromatography on silica gel using dichloromethane as eluent to afford the desired Pd3O3 as a light yellow solid (390 mg, 63%). $^1$H NMR (DMSO-d$_6$, 400 MHz): δ 7.16 (d, J=7.6 Hz, 2H), 7.27 (dd, J=15.6, 8.0 Hz, 2H), 7.55 (dd, J=12.4, 6.4 Hz, 2H), 7.74 (d, J=7.2 Hz, 2H), 8.09-8.15 (m, 2H), 8.28 (d, J=8.4 Hz, 2H), 8.97 (d, J=5.2 Hz, 2H). MS (APCI+) m/z: [M]+ calcd for C$_{22}$H$_{15}$ON$_2$OPd 429.0219, found 429.0232. The $^1$H NMR spectrum of Pd3O3 (DMSO-d$_6$, 400 MHz) is shown in FIG. 2.

Devices

Materials:

TAPC (di-[4-(N,N-di-toylyl-amino)-phenyl]cyclohexane), TrisPCz (9,9',9"-triphenyl-9H,9'H,9"H-3,3':6'3"-tercarbazole), 26mCPy (2,6-bis(N-carbazolyl) pyridine), DPPS (diphenyl-bis[4-(pyridin-3-yl)phenyl]silane), BmPyPB (1,3-bis[3,5-di(pyridin-3-yl)phenyl]benzene), and BPyTP (2,7-di(2,2'-bipyridin-5-yl)triphenylene) were all synthesized by methods known in the art. HATCN (1,4,5,8,9,11-hexaazatriphenylene-hexacarbonitrile), NPD (N,N'-diphenyl-N,N'-bis(1-naphthyl)-1,1'-biphenyl-4,4"-diamine), BAlq bis(2-methyl-8-quinolinolato)(biphenyl-4-olato)aluminum, and mCBP 3,3-di(9H-carbazol-9-yl)biphenyl were all provided from commercial suppliers. All materials were sublimed 1 or more times in a 4-zone thermal gradient furnace at pressures of 10$^{-5}$ torr prior to use.

Device Fabrication and Characterization:

Devices were fabricated on pre-patterned substrates of ITO on glass. Prior to deposition substrates were cleaned by a gentle scrub followed by subsequent sonication in water, acetone, and isopropanol. Organic layers were deposited by vacuum thermal evaporation in a custom made chamber by Travato Man. Inc. Base pressures were kept between 10$^{-8}$-10$^{-7}$ torr and deposition rates were kept between 0.5-1.0 Å/s. A 1 nm LiF buffer layer was deposited at 0.2 Å/s. Al cathodes were deposited without breaking vacuum at 1-2 Å/s through a shadow mask defining a device area of 4 mm$^2$.

High efficiency devices were fabricated in the structure: ITO/HATCN (10 nm)/NPD (40 nm)/TAPC (10 nm)/x % Pt3O3: 26mCPy (25 nm)/DPPS (10 nm)/BmPyPB (40 nm)/LiF/Al where x=5% or 10%. For stable devices the following structure was used: ITO/HATCN (10 nm)/NPD (40 nm)/TrisPCz (0 or 10 nm)/x % Pd3O3:Host (25 nm)/BAlq (10 nm)/BPyTP (40 nm)/LiF/Al where x=2% or 10% and the host is either 2,6 mCPy or mCBP. Current-voltage-luminance characteristics were taken with a Keithley 2400 Source-Meter and a Newport 818 Si photodiode inside a nitrogen-filled glove-box with all devices assumed to be Lambertian emitters. Accelerated lifetime testing was performed at a constant current of 20 mA/cm$^2$. EL spectra were taken at 1 mA/cm$^2$ using a calibrated ocean optics HR4000 spectrometer.

Figure 3:
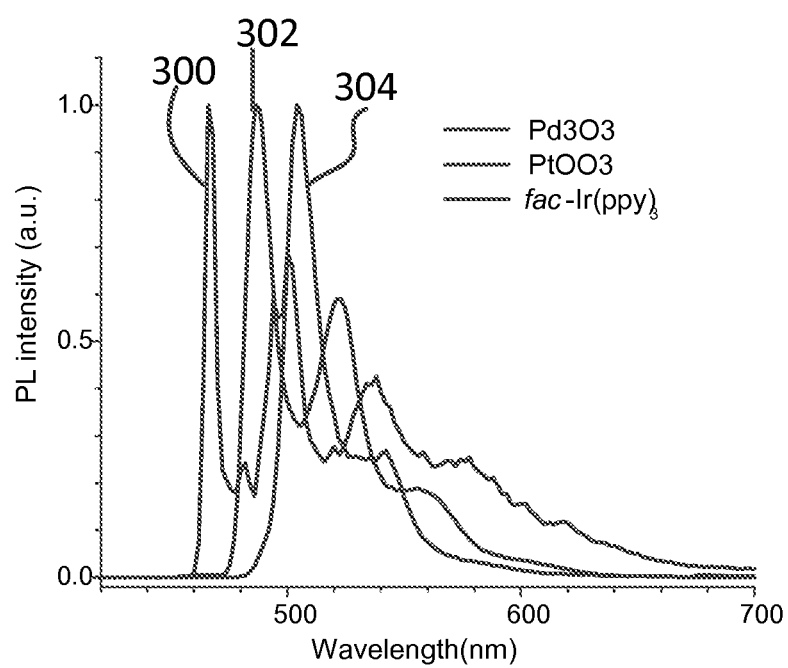
FIG. 3 shows photoluminescent spectra of Pd3O3, PtOO3, and fac-Ir(ppy)₃.

Low temperature emission spectra of Pd3O3 and its Pt and Ir analogs are shown in FIG. 3 as plots 300, 302, and 304, respectively. Although the three metal complexes employ the same cyclometalating ligand of phenyl pyridine, the incorporation of palladium has shifted the maximum emission wavelength of metal complexes from 504 nm for fac-Ir(ppy)$_3$ to 466 nm for Pd3O3, indicating the suitability of Pd3O3 as a phosphorescent emitter for blue and white OLED applications.

Figure 4:
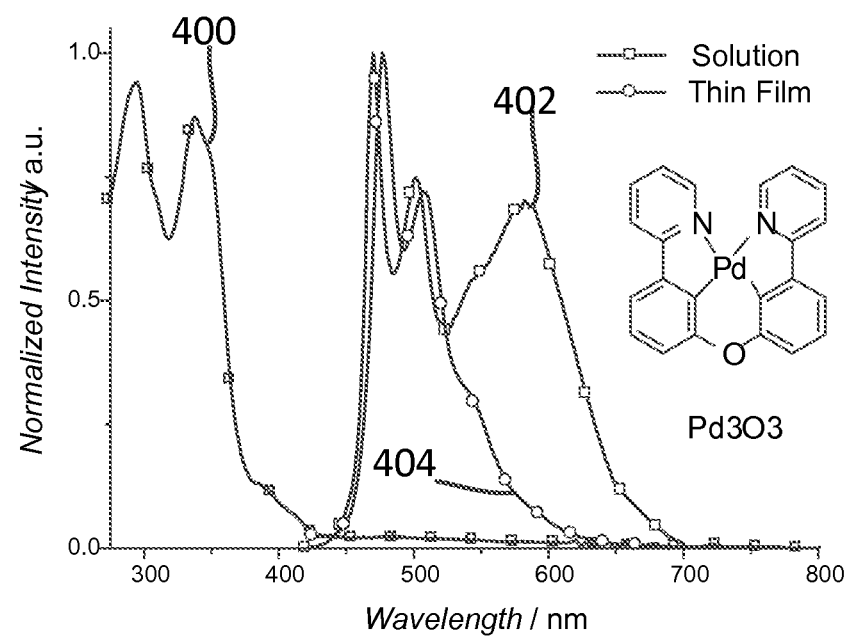
FIG. 4 shows absorption spectra of a solution of Pd3O3 in solution and in a dilute thin film.
Figure 5:
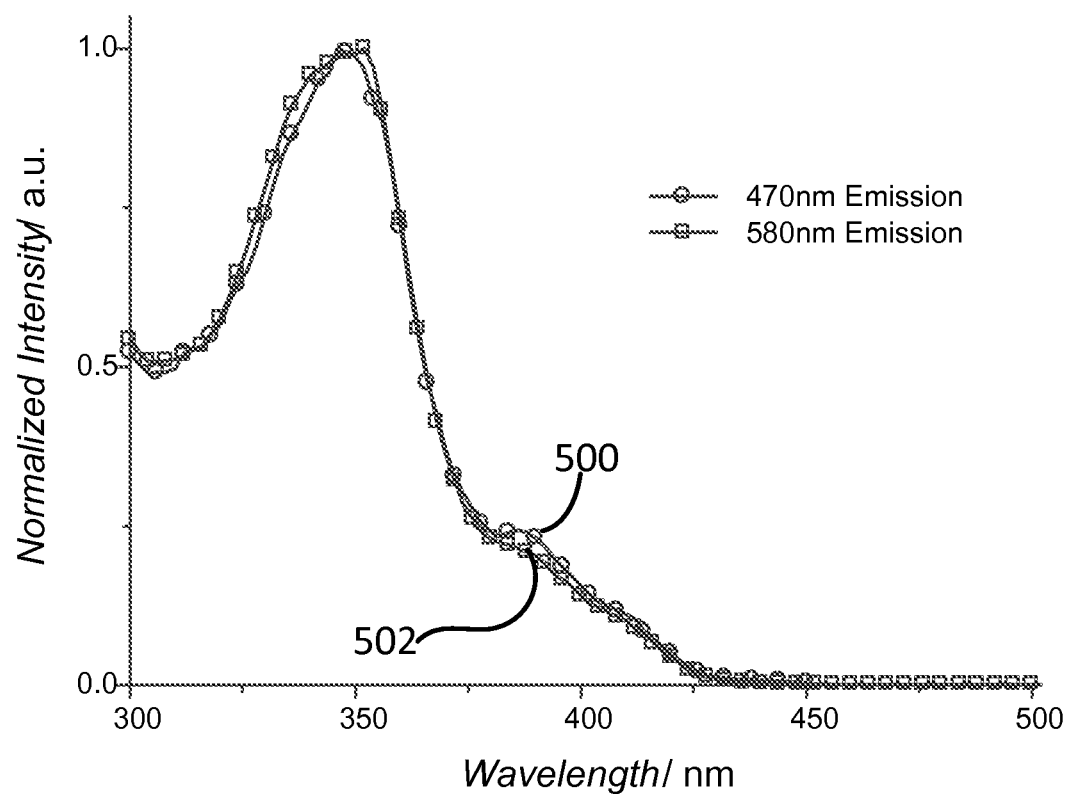
FIG. 5 shows excitation spectra of Pd3O3 in solution.

Both a dilute solution of Pd3O3 in dichloromethane (DCM) and a dilute thin film (1% by weight) of Pd3O3 in 2,6-bis(N-carbazolyl) pyridine (26mCPy) were prepared for spectral analysis. The normalized absorption and photoluminescent spectrum of the solution are shown in plots 400 and 402, respectively, and the photoluminescent spectrum of the thin film is shown in plot 404 of FIG. 4. The strong solution absorption peaks below ~360 nm are assigned to $^1$π-π* transitions, localized on the phenyl-pyridine ligands. The small shoulder in the 360-450 nm range is assigned to singlet metal to ligand charge transfer ($^1$MLCT) transitions. Both the solution and the thin film show molecular emission peaks in the 450-550 nm range. Plot 402 shows an emission onset near 450 nm with a primary emission peak at 477 nm and a second peak at 507 nm. Due to strong intermolecular interactions, all prepared solutions formed suspensions of small molecular aggregates. Consequently, plot 400 contained a large, broad aggregate emission which peaks at 582 nm. As shown in plots 500 and 502 of FIG. 5, this low energy emission band is attributed to excimer emission which is supported by the excitation spectra showing a shared origin for both the monomer and aggregate emission.

Figure 6:
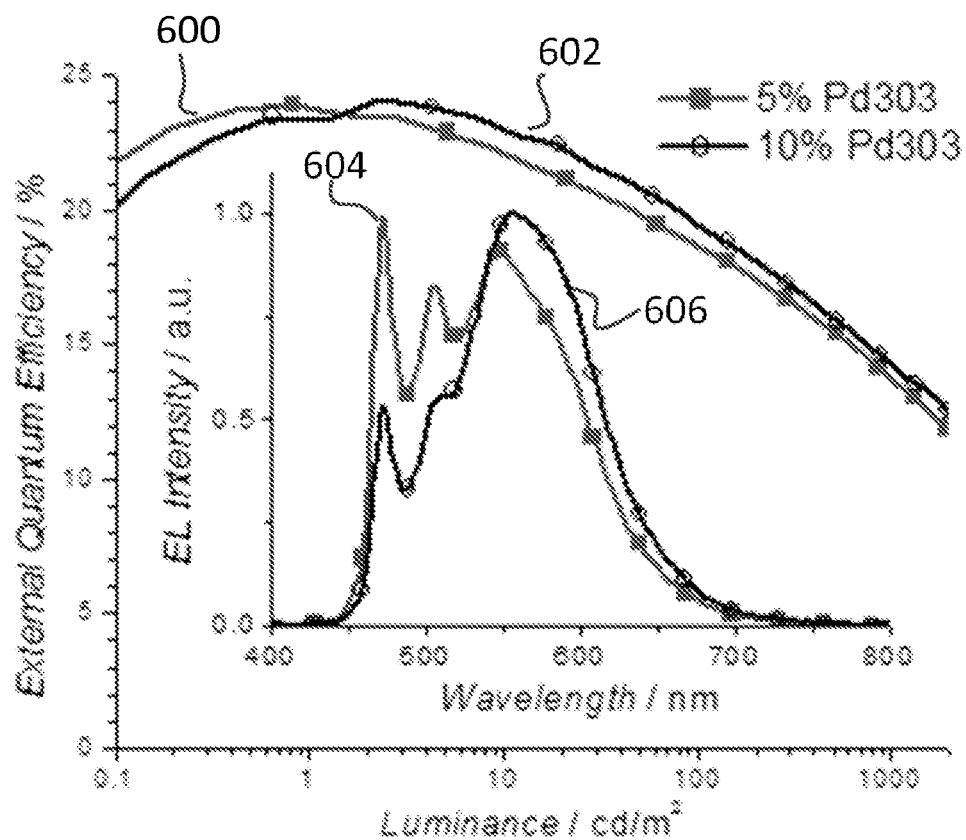
FIG. 6 shows external quantum efficiency versus luminance and electroluminescent spectra of devices with Pd3O3.

To evaluate the performance of Pd3O3 in a WOLED setting, devices were fabricated in a known efficient and charge confining structure: ITO/HATCN (10 nm)/NPD (40 nm)/TAPC (10 nm)/x % Pt3O3: 26mCPy (25 nm)/DPPS (10 nm)/BmPyPB (40 nm)/LiF/Al for dopant concentrations of 5% and 10% Pt3O3 by mass. HATCN is 1,4,5,8,9,11-hexaazatriphenylene-hexacarbonitrile, NPD is N,N'-diphenyl-N,N'-bis(1-naphthyl)-1,1'-biphenyl-4,4"-diamine, TAPC is di-[4-(N,N-di-toylyl-amino)-phenyl]cyclohexane, 26mCPy is 2,6-bis(N-carbazolyl) pyridine, DPPS is diphenyl-bis[4-(pyridin-3-yl)phenyl]silane, and BmPyPB is 1,3-bis[3,5-di(pyridin-3-yl)phenyl]benzene. Plots 600 and 602 in FIG. 6 show external quantum efficiency (EQE) versus luminance for devices with 5% Pd3O3 and 10% Pd3O3, respectively, with high peak EQEs of 23.9% and 24.2%. Plot 600 shows an efficiency of the 5% doped device of 18.5% at 100 cd/m$^2$ and 13.8% at 1000 cd/m$^2$. Plot 602 shows an efficiency of the 10% doped device of 19.3% at 100 cd/m$^2$ and 14.3% at 1000 cd/m$^2$. This roll off may be due at least in part to the combination of charge balance at the high current density and the long PL emission lifetimes of many palladium complexes (in the range of tens and hundreds of microseconds or even longer).

Plots 604 and 606 show electroluminescent spectra for devices with 5% Pd3O3 and 10% Pd3O3, respectively, with a monomer emission peak at 472 nm and a broad excimer peak at 550-600 nm. As shown in plot 604, the excimer peak and monomer peak are of approximately equal height, yielding warm white light with CIE coordinates of (0.34, 0.47) and CRI of 53. As shown in plot 606, when the concentration of Pd3O3 is increased to 10% dopant concentration, the excimer emission broadens and increases to approximately twice the height of the monomer emission. Consequently, the emission is orange with CIE coordinates of (0.39, 0.50) and a CRI of 52. It should also be noted that the monomer to excimer emission balance occurs at a much lower dopant concentration than many of the reported platinum complexes, yielding an emission spectrum with non-ideal CIE coordinates. This may be due to the preferential stacking of Pd3O3 molecules which was also reflected in the poor solubility of Pd3O3. Furthermore, the excimer emission drops off rapidly at 600 nm, missing a significant portion of the red spectrum leading in part to the low CRI. Modifying the planar geometry nature of Pd3O3 molecules by adding steric substituents or using bulky bridging ligands may allow stronger molecular interaction between emissive materials and the host molecules and allow tuning of the monomer and excimer emission colors to yield more ideal white color.

Figure 7A:
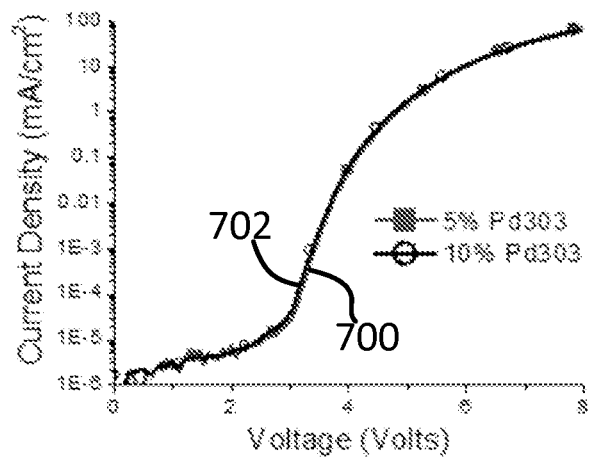
FIGS. 7A and 7B show current density-voltage characteristics and power efficiency, respectively, of devices with Pd3O3.
Figure 7B:
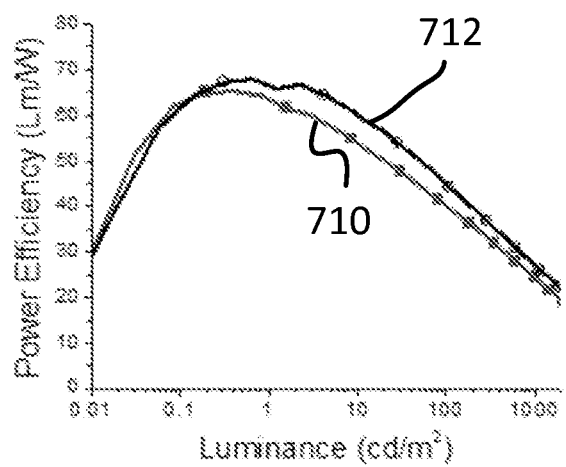

Plots 700 and 702 in FIG. 7A show current density versus voltage for Pd3O3 devices with 5% and 10% dopant concentration, respectively. Plots 710 and 712 in FIG. 7B show peak power efficiencies (PE) of 65.3 lm/W and 67.9 lm/W for Pd3O3 devices with 5% and 10% dopant concentration, respectively.

Figure 8A:
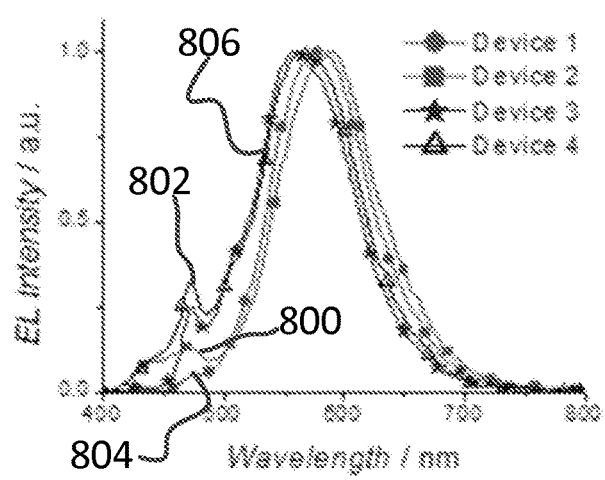
FIGS. 8A-8D show electroluminescent spectra, external quantum efficiency, power efficiency, and operational lifetimes, respectively, of devices with Pd3O3.
Figure 8B:
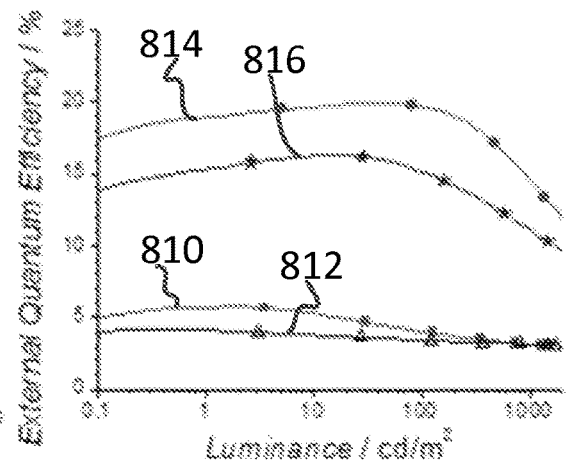
Figure 8C:
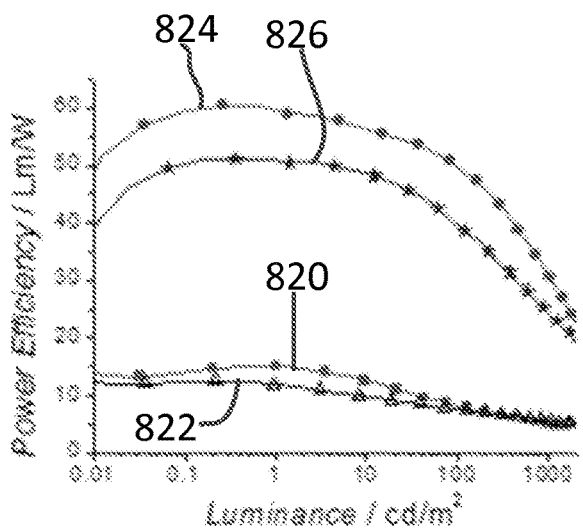

Due to the known instability of the TAPC and DPPS blocking materials, separate Pd3O3 devices were fabricated in four different stable device structures:
Device 1: ITO/HATCN/NPD/TrisPCz/10% Pd3O3:mCBP/BAlq/BPyTP/LiF/Al
Device 2: ITO/HATCN/NPD/10% Pd3O3:mCBP/BAlq/BPyTP/LiF/Al
Device 3: ITO/HATCN/NPD/TrisPCz/10% Pd3O3:26mCPy/BAlq/BPyTP/LiF/Al
Device 4: ITO/HATCN/NPD/10% Pd3O3:26mCBP/BAlq/BPyTP/LiF/Al, where TrisPCz is 9,9',9"-triphenyl-9H,9'H,9"H-3,3':6'3"-tercarbazole, mCBP is 3,3-di(9H-carbazol-9-yl)biphenyl, BAlq is bis(2-methyl-8-quinolinolato)(biphenyl-4-olato)aluminum, and BPyTP is 2,7-di(2,2'-bipyridin-5-yl)triphenylene The devices were fabricated with a fixed dopant concentration of 10% in order to study the stability of OLEDs with emission originating primarily from the Pd3O3 emitters. As seen in FIG. 8A, the resulting spectra are dominated by the broad excimer emission, due at least in part to excimer formation at a moderate dopant concentration to achieve a balanced spectrum. Devices 2 and 4 had no TrisPCz blocking layer, while Devices 1 and 3 had TrisPCz. As shown in plots 800 and 802, Device 2 and Device 4 had significant emission in the 400-450 nm range. This indicates a partial NPD emission due to possible electron leakage or exciton energy transfer to the hole-transporting NPD layer. Plots 810 and 812 in FIG. 8B show low peak EQEs in the range of 4-6% for Devices 2 and 4, respectively. However, Devices 1 and 3 were very efficient. As shown in plot 814 in FIG. 8B, Device 1 reached a peak EQE of 19.9%. As shown in plot 824 in FIG. 8C, Device 1 had a peak power efficiency of 60.5 lm/W. As shown in plot 816 in FIG. 8B, Device 3 reached a peak EQE of 16.2%. As shown in plot 826 in FIG. 8C, Device 3 reached a peak power efficiency of 51.2 lm/W. The roll-off for these devices was also less significant than for the previous efficient structures. Referring back to plots 814 and 816 in FIG. 8B, Device 1 and Device 3 had EQE values of 14.6% and 11.1% at 1000 cd/m$^2$, respectively.

Figure 8D:
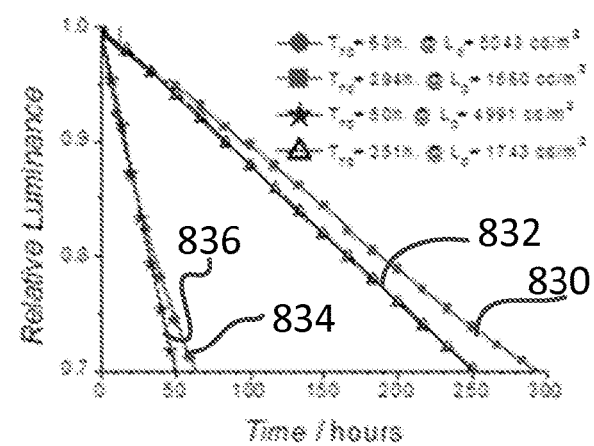

The device operational lifetimes of all four stable devices were measured at accelerated conditions by driving the devices at a constant current of 20 mA/cm$^2$. As shown in plot 830 in FIG. 8D, Device 2 demonstrated a long operational lifetime to 70% of initial luminance ($LT_{70}$) of 294 h at an initial luminance of 1560 cd/m$^2$. As shown in plot 832 in FIG. 8D, Device 4 demonstrated an operational lifetime to 70% of initial luminance ($LT_{70}$) of 251 h at an initial luminance of 1743 cd/m$^2$. When TrisPCz was used, the device operational lifetimes dropped due to possible charge build up at the interface of EML/EBL. Nevertheless, moderately high operational lifetimes were achieved. As shown in plots 834 and 836 in FIG. 8D, the operational lifetimes for Devices 1 and 3, respectively, were 63 h at 5043 cd/m$^2$ and 50 h at 4991 cd/m$^2$. Furthermore, approximating these accelerated testing results at practical luminance of 1000 cd/m$^2$ yields lifetimes of 986 h for Device 1 and 769 h for Device 3, respectively. These high lifetimes (close to 1000 h) and high power efficiency (close to 30 lm/W without any outcoupling enhancement) at practical luminance, approaches the minimum commercialization requirement with appropriate lamination quality. Furthermore, with incorporation of light outcoupling techniques, doubling the luminance at a given driving condition could be reasonably expected to yield lifetimes in the range of 2500-3500 h at 1000 cd/m$^2$.

Figure 9:
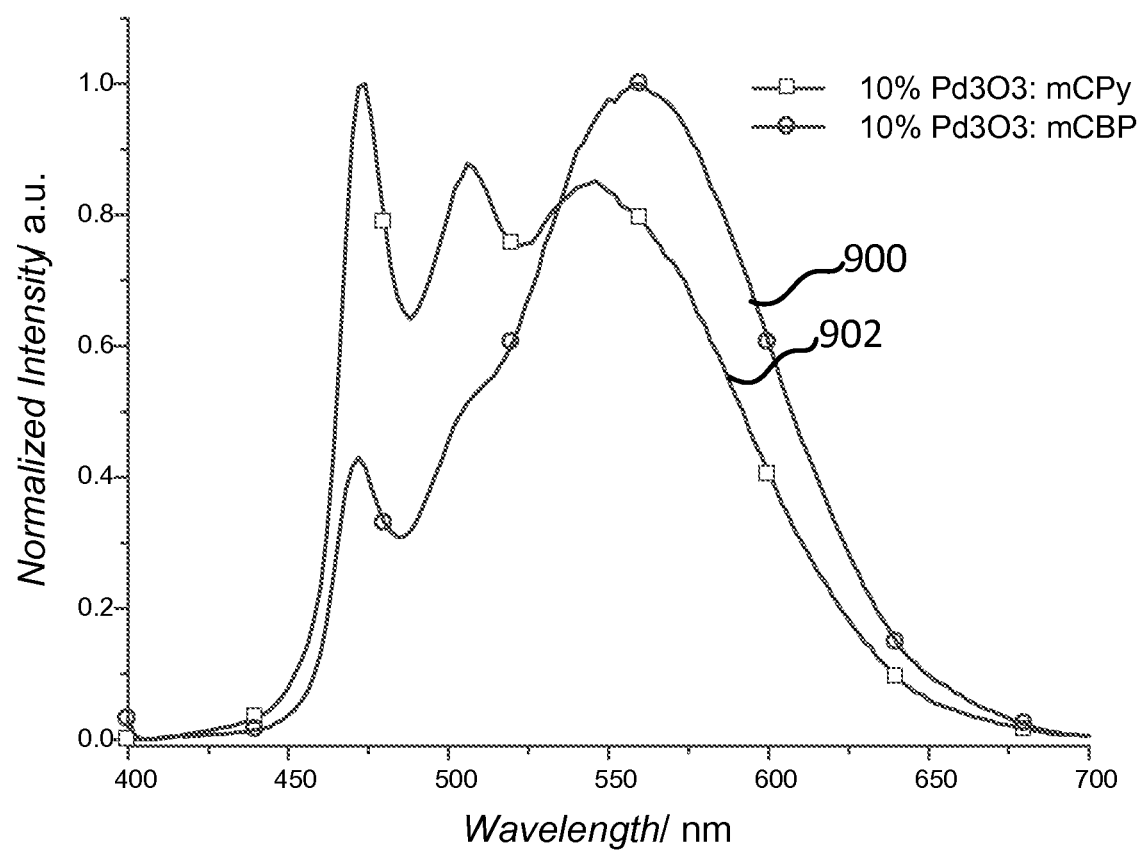
FIG. 9 shows photoluminescent spectra of doped thin films of Pd3O3.

Devices 5 and 6 were also fabricated:
Device 5: ITO/HATCN/NPD/TrisPCz/2% Pd3O3:mCBP/BAlq/BPyTP/LiF/Al
Device 6: ITO/HATCN/NPD/2% Pd3O3:mCBP/BAlq/BPyTP/LiF/Al.
Where mCBP was selected as a host for both higher efficiencies and longer operational lifetimes, excimers were found to form more readily in mCBP than mCPy. This is shown in plots 900 and 902 in FIG. 9, which normalized intensity for devices with 10% Pd3O3 in mCBP and 10% Pd3O3 in mCPy, respectively. This difference may be due to a solid solubility effect, requiring a low concentration of 2% to balance the emission.

Figure 10:
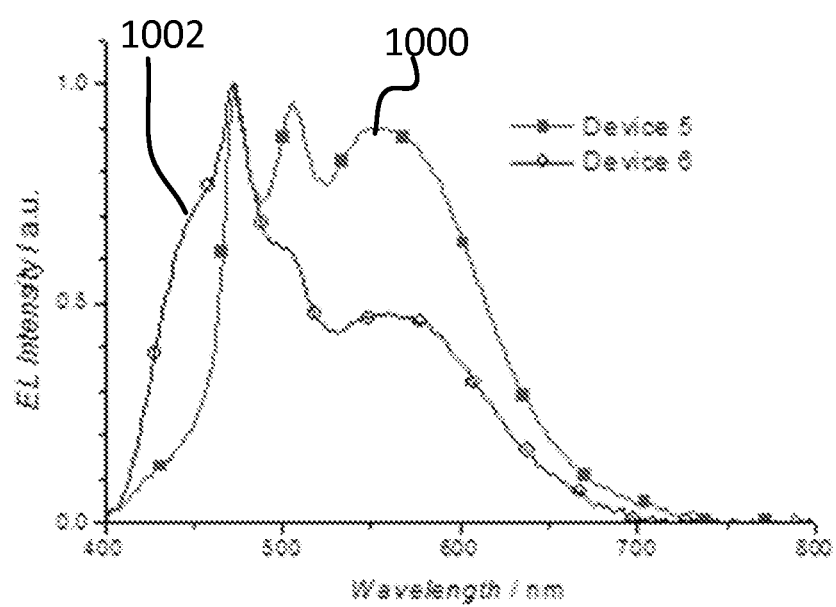
FIG. 10 shows electroluminescent spectra of Pd3O3 devices.

The resulting emission spectra are shown in FIG. 10. In plot 1000, Device 5, with a TrisPCz blocking layer, showed a nearly balanced emission spectrum resulting in color coordinates of (0.33, 0.44) and a CRI of 63. There is also emission in the 400-450 nm range that was not present in the 10% doped devices indicating some leakage processes in this device. As shown in plot 1130 in FIG. 11D, the consequence is a peak efficiency of only 5.4%. As shown in plot 1002 in FIG. 10, Device 6, which has no TrisPCz blocker, has an emission between 400-450 that increases substantially due at least in part to energy transfer into the NPD layer. As shown in plot 1132 in FIG. 11D, this drops the peak efficiency to 1.8%. However, the additional blue emission did improve the CRI to 80 and CIE coordinates of (0.27, 0.30).

Figure 11A:
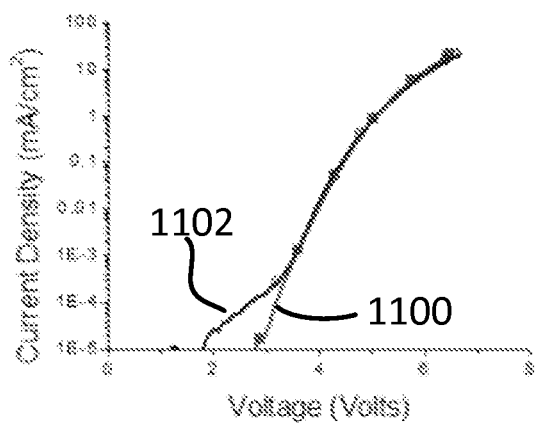
FIGS. 11A-11D show current density-voltage characteristics, operational lifetimes, power efficiency, and external quantum efficiency, respectively, of devices with Pd3O3.
Figure 11B:
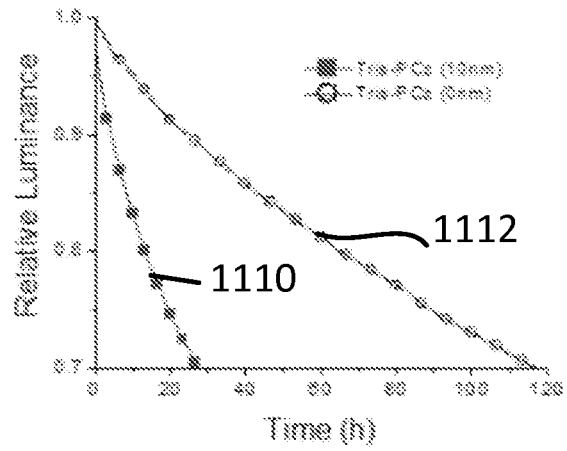
Figure 11C:
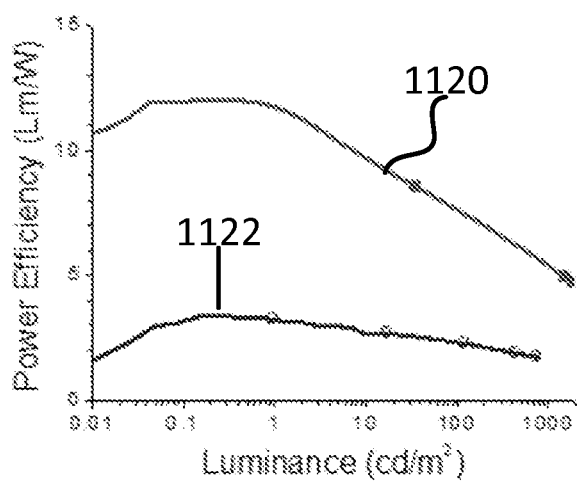
Figure 11D:
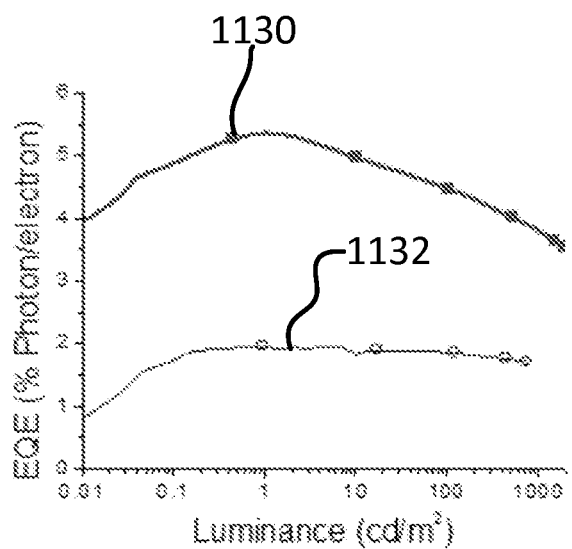

Plots 1100 and 1102 in FIG. 11A show current density versus voltage for Devices 5 and 6, respectively. Plots 1120 and 1122 in FIG. 11C show power efficiency versus luminance for Devices 5 and 6, respectively. As shown in FIG. 11C, the peak power efficiency of Device 5 is about 12.1 lm/W, and the peak power efficiency of Device 6 is about 3.3 lm/W.

The device operational lifetime at accelerated testing conditions of 20 mA/cm$^2$ were also collected for these 2% doped devices. Plot 1110 in FIG. 11B shows a resulting $LT_{70}$ for Device 5 of 28 h. Plot 1112 in FIG. 11B shows a $LT_{70}$ for Device 6 of 117 h. This is nearly a third of those with a 10% dopant concentration. Approximated lifetimes at 1000 cd/m$^2$ are only 86 h and 70 h for Devices 5 and 6, respectively. These results reflect the challenge in balancing color, efficiency, and operational stability when molecular aggregation is too favorable and the optimal emission color of white OLED is realized at a low dopant concentration.

Table 1 summarizes the device performance of Devices 1-6 as described herein.

TABLE 1

Summary of device performance for stable devices of Pd3O3

| Device | CRI | CIE | EQE (%) | | PE (lm/W) | | $L_0$ | $LT_{70}$ | |
| | | | peak | 1000 cd/m$^2$ | peak | 1000 cd/m$^2$ | (cd/m$^2$) | @$L_0$ | @1000 cd/m$^2$ |
|---|---|---|---|---|---|---|---|---|---|
| 1 | 48 | (0.48, 0.50) | 19.9 | 14.6 | 60.5 | 30.8 | 5043 | 63 | 986 |
| 2 | 57 | (0.47, 0.46) | 5.7 | 3.1 | 15.1 | 5 | 1560 | 294 | 626 |
| 3 | 48 | (0.42, 0.52) | 16.2 | 11.1 | 51.2 | 24.5 | 4991 | 50 | 769 |

TABLE 1-continued

Summary of device performance for stable devices of Pd3O3

| Device | CRI | CIE | EQE (%) peak | EQE (%) 1000 cd/m² | PE (lm/W) peak | PE (lm/W) 1000 cd/m² | $L_0$ (cd/m²) | $LT_{70}$ @$L_0$ | $LT_{70}$ @1000 cd/m² |
|---|---|---|---|---|---|---|---|---|---|
| 4 | 56 | (0.41, 0.48) | 4.1 | 3.1 | 12.5 | 5.7 | 1743 | 251 | 645 |
| 5 | 63 | (0.33, 0.44) | 5.4 | 3.8 | 12 | 5.4 | 1930 | 28 | 86 |
| 6 | 80 | (0.27, 0.30) | 1.9 | — | 3.4 | — | 740 | 117 | 70 |

Figure 12:
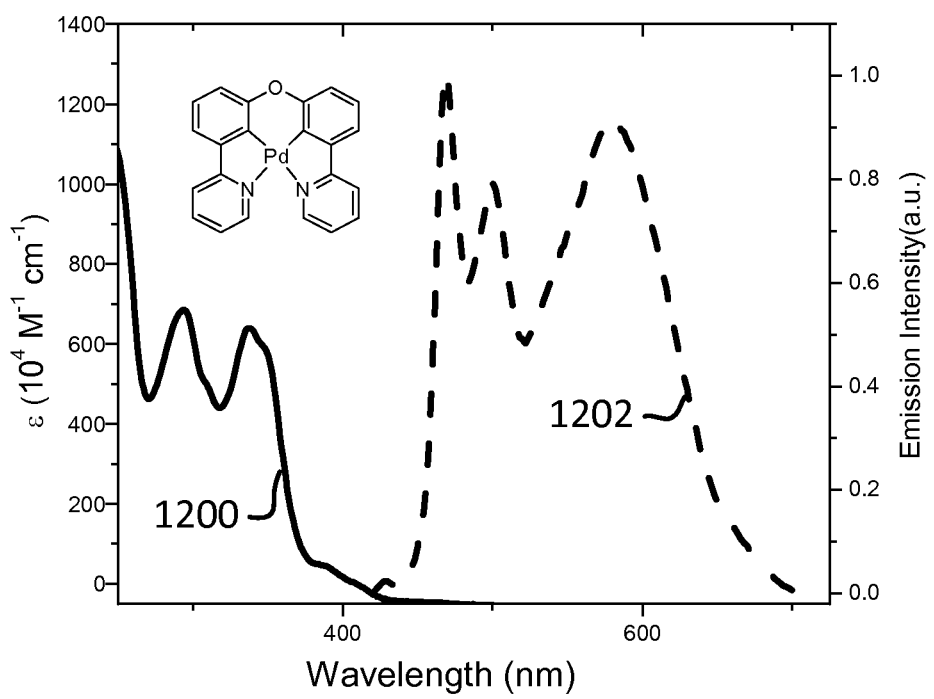
FIG. 12 shows an absorption spectrum and an emission spectrum of Pd(II) 2-(3-(3-pyridin-2-yl)phenoxy)phenyl) pyridine.

Pd3O3 was tested as an emitter in a device having the following structure: ITO/HATCN (10 nm)/NPD (40 nm)/TrisPCZ (10 nm)/Pd3O3:mCBP (25 nm)/mCBT (8 nm)/BPyTP (40 nm)/LiF/Al. Plots 1200 and 1202 in FIG. 12 show electroluminescence spectra of this device and a device using mCPy as a host material, respectively.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:
1. A compound of General Formula I:

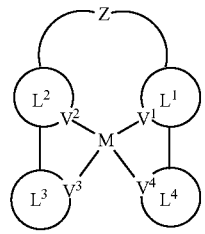

General Formula I wherein:
M is $Pd^{2+}$, $Ir^+$, or $Rh^+$;
each of $V^1$, $V^2$, $V^3$, and $V^4$ is coordinated to M and is independently N, C, P, B, or Si, wherein at least one of $V^1$ and $V^2$ is C;
each of $L^1$, $L^2$, $L^3$, and $L^4$ is a six-membered ring and is independently a substituted or unsubstituted aryl, cycloalkyl, cycloalkenyl, heterocyclyl, heteroaryl, carbene, or N-heterocyclic carbene; and
Z is O, S, NR, $CR_2$, $SiR_2$, BR, PR,

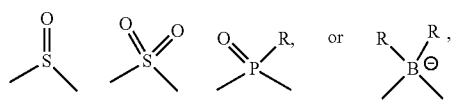

where each R is independently substituted or unsubstituted $C_1$-$C_4$ alkyl or substituted or unsubstituted aryl.
2. The compound of claim 1, wherein the compound has one of the following structures:

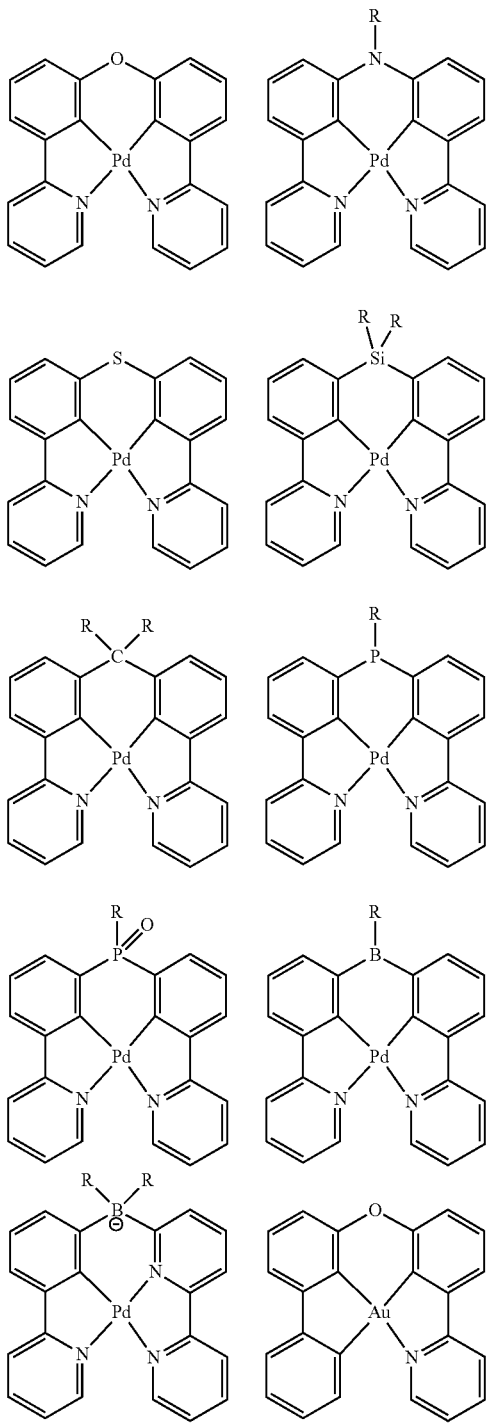

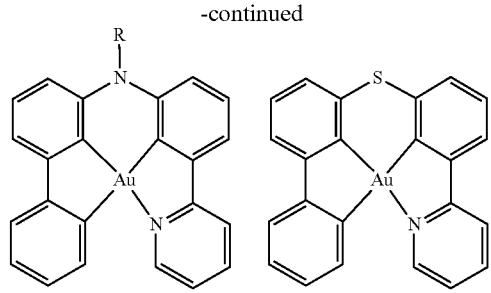
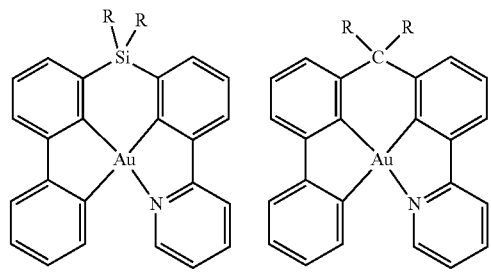
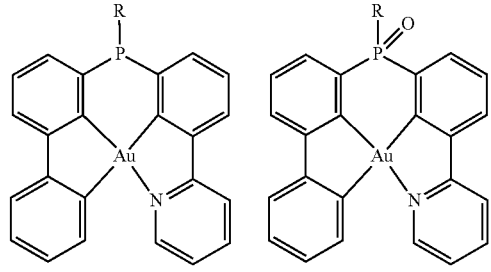
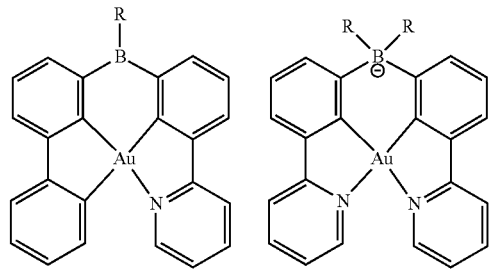
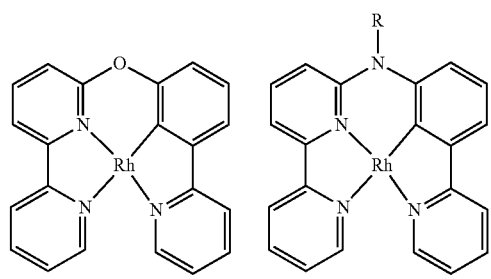
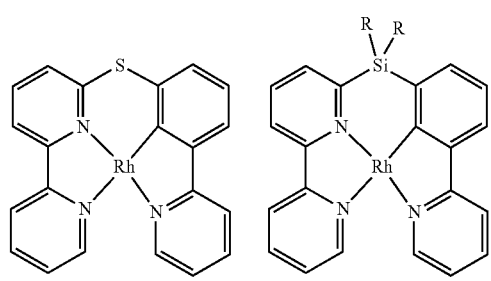
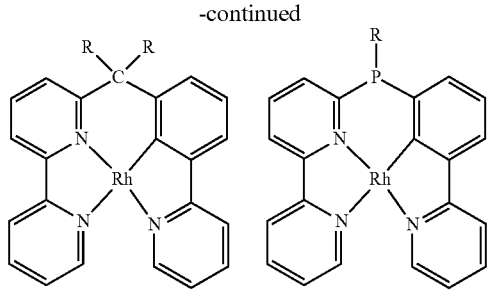
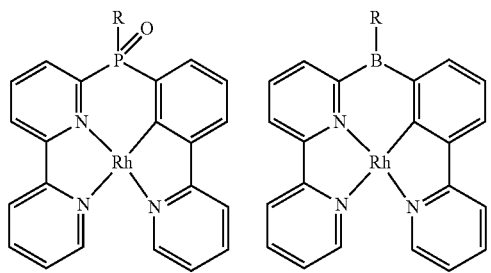
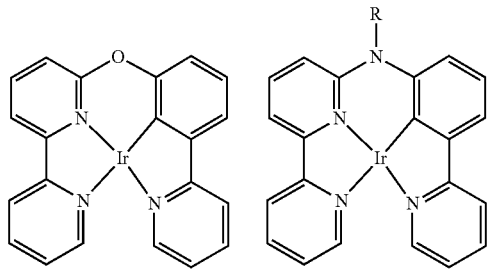
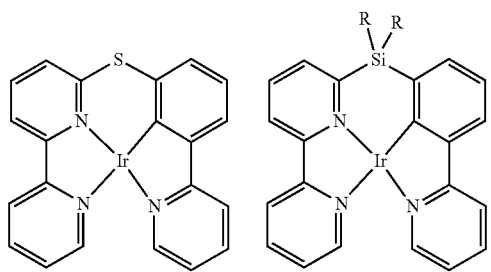
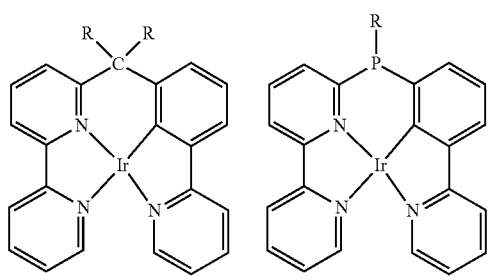
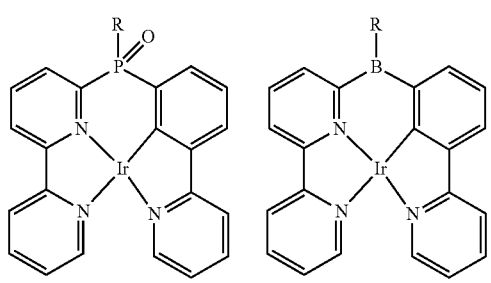

107
-continued
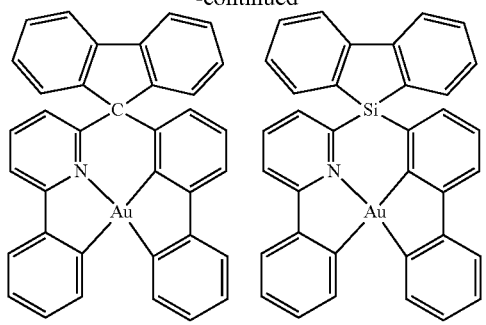
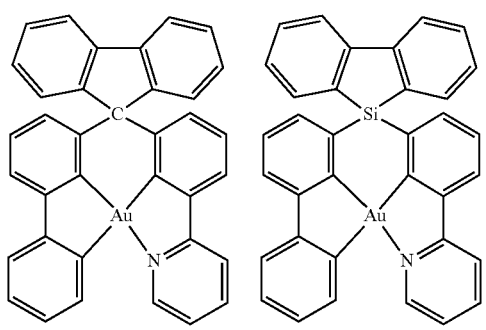
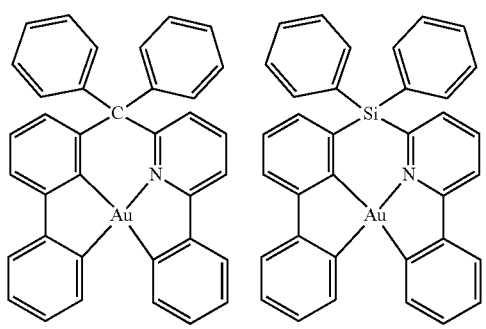
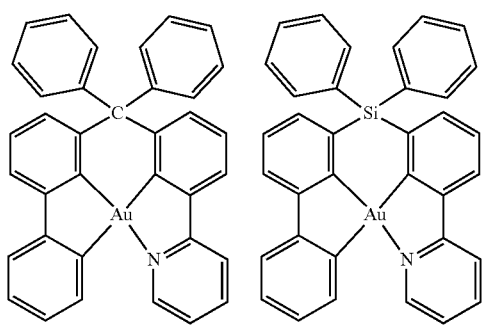
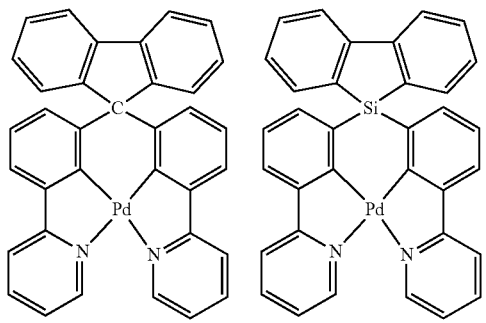
108
-continued
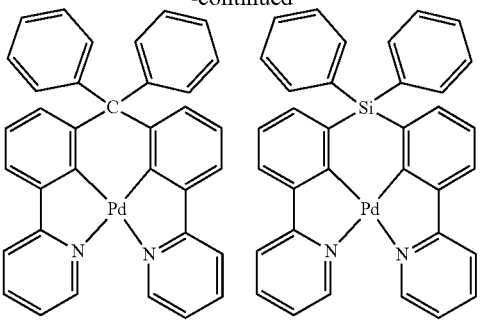
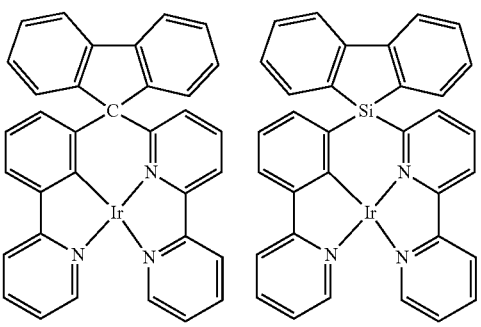
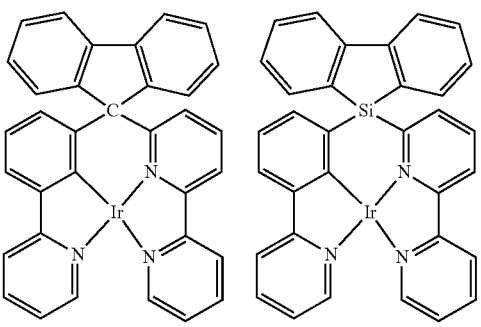
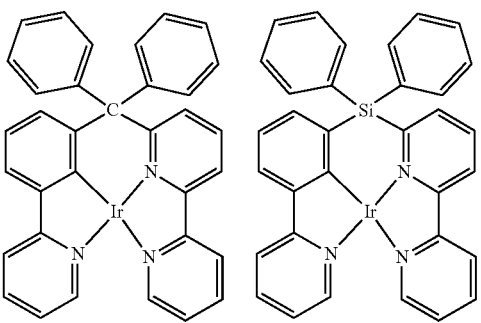
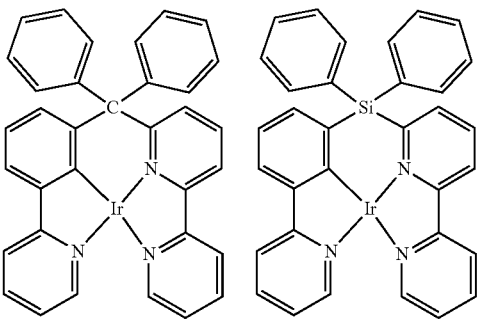

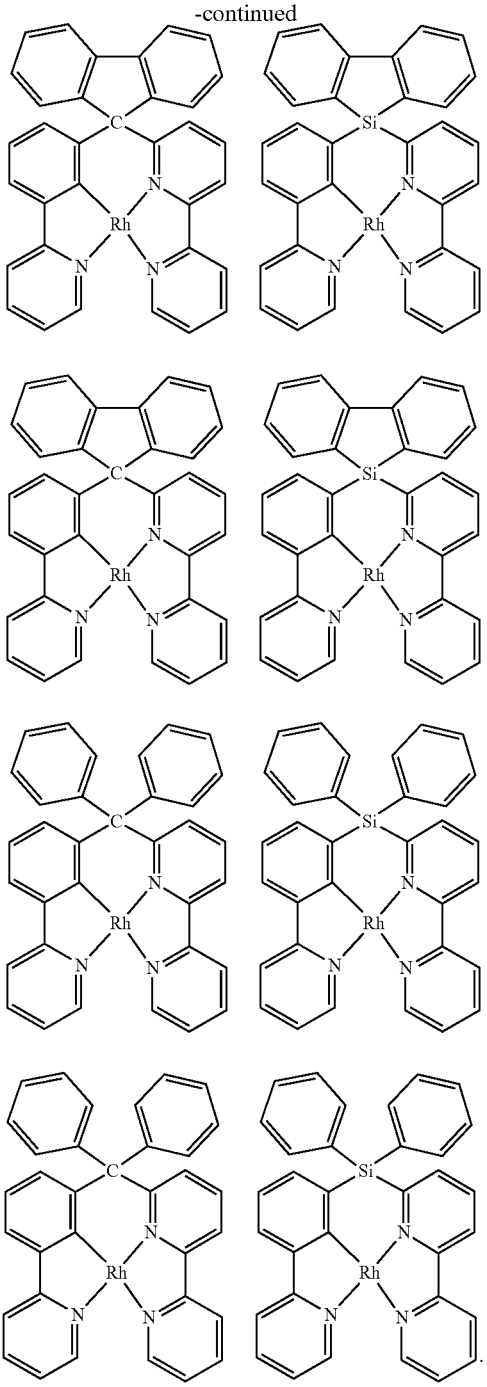

3. A light emitting device comprising the compound of claim 1.

4. An OLED device comprising the compound of claim 1.

5. The OLED device of claim 4, wherein the device is a phosphorescent OLED device.

6. A photovoltaic device comprising the compound of claim 1.

7. A luminescent display device comprising the compound claim 1.

8. The compound of claim 1, wherein at least one of $V^3$ and $V^4$ is C.

9. A compound of General Formula I:

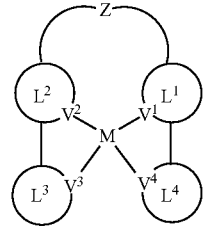

General Formula I wherein:
M is $Pd^{2+}$;
each of $V^1$ and $V^2$ is N;
each of $V^3$ and $V^4$ is C;
each of $L^1$, $L^2$, $L^3$, and $L^4$ is a six-membered ring and is independently a substituted or unsubstituted aryl, cycloalkyl, cycloalkenyl, heterocyclyl, heteroaryl, carbene, or N-heterocyclic carbene; and
Z is BR, PR,

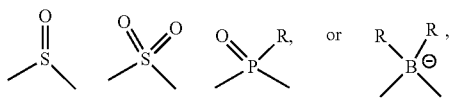

where each R is independently substituted or unsubstituted $C_1$-$C_4$ alkyl or substituted or unsubstituted aryl.

10. The compound of claim 9, wherein the compound has one of the following structures:

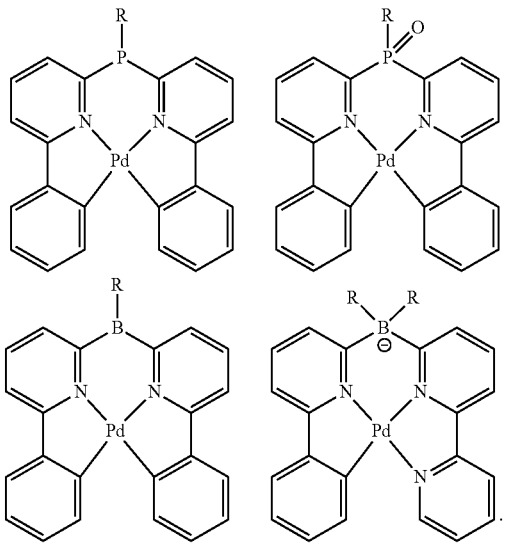

11. A compound of General Formula I:

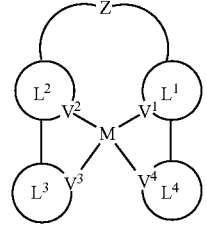

General Formula I wherein:
M is $Pd^{2+}$, $Ir^k$, $Rh^+$, or $Au^{3+}$;
each of $V^1$ and $V^2$ is N;

each of $V^3$ and $V^4$ is C;

each of $L^1$, $L^2$, $L^3$, and $L^4$ is a six-membered ring and is independently a substituted or unsubstituted aryl, cycloalkyl, cycloalkenyl, heterocyclyl, heteroaryl, carbene, or N-heterocyclic carbene; and Z is $CR_2$ or $SiR_2$, where $R_2$ represents a biphenyl group, and each of $CR_2$ and $SiR_2$ represents a fluorenyl group.

12. The compound of claim 11, wherein the compound has one of the following structures:

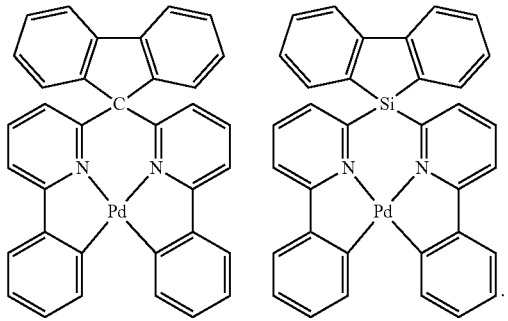

13. A compound of General Formula I:

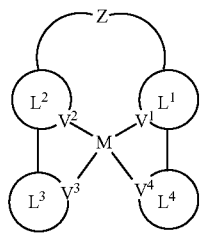

General Formula I wherein:

M is $Pd^{2+}$, $Ir^k$, $Rh^+$, or $Au^{3+}$;

$V^1$ and $V^2$ are coordinated to M and are each independently N, C, P, B, or Si, wherein at least one of $V^1$ and $V^2$ is C;

$V^3$ and $V^4$ are coordinated to M and are each N;

each of $L^1$, $L^2$, $L^3$, and $L^4$ is a six-membered ring and is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR,

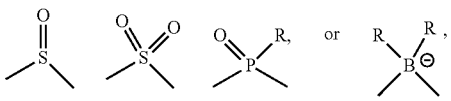

where each R is independently substituted or unsubstituted $C_1$-$C_4$ alkyl or substituted or unsubstituted aryl.

14. A light emitting device comprising the compound of claim 13.

15. An OLED device comprising the compound of claim 13.

16. The OLED device of claim 15, wherein the device is a phosphorescent OLED device.

17. A photovoltaic device comprising the compound of claim 13.

18. A luminescent display device comprising the compound claim 13.

* * * * *